(12) United States Patent
McCarthy et al.

(10) Patent No.: US 10,759,785 B2
(45) Date of Patent: Sep. 1, 2020

(54) COMPOUNDS

(71) Applicant: ENTERPRISE THERAPEUTICS LIMITED, Falmer, Brighton (GB)

(72) Inventors: Clive McCarthy, Brighton (GB); Jonathan David Hargrave, Abingdon (GB); Duncan Alexander Hay, Abingdon (GB); Thomas Beauregard Schofield, Abingdon (GB); Naomi Went, Abingdon (GB)

(73) Assignee: Enterprise Therapeutics Limited, Falmer, Brighton (GB)

( * ) Notice: Subject to any disclaimer, the term of this patent is extended or adjusted under 35 U.S.C. 154(b) by 0 days.

(21) Appl. No.: 16/312,158

(22) PCT Filed: Jun. 21, 2017

(86) PCT No.: PCT/GB2017/051815
§ 371 (c)(1),
(2) Date: Dec. 20, 2018

(87) PCT Pub. No.: WO2017/221008
PCT Pub. Date: Dec. 28, 2017

(65) Prior Publication Data
US 2019/0233402 A1    Aug. 1, 2019

(30) Foreign Application Priority Data
Jun. 21, 2016    (GB) .................... 1610854.0

(51) Int. Cl.
| C07D 403/12 | (2006.01) |
| C07D 403/14 | (2006.01) |
| C07D 401/14 | (2006.01) |
| C07D 405/14 | (2006.01) |

(52) U.S. Cl.
CPC ......... C07D 403/12 (2013.01); C07D 401/14 (2013.01); C07D 403/14 (2013.01); C07D 405/14 (2013.01)

(58) Field of Classification Search
CPC .. C07D 403/12; C07D 401/14; C07D 405/14; C07D 403/14
See application file for complete search history.

(56) References Cited

FOREIGN PATENT DOCUMENTS

| WO | WO 2003/070182 A2 | 8/2003 |
| WO | WO 2003/070184 A2 | 8/2003 |
| WO | WO 2004/073629 A2 | 9/2004 |
| WO | WO 2005/016879 A2 | 2/2005 |
| WO | WO 2005/018644 A1 | 3/2005 |
| WO | WO 2005/025496 A2 | 3/2005 |
| WO | WO 2005/034847 A2 | 4/2005 |
| WO | WO 2005/044180 A2 | 5/2005 |
| WO | WO 2006/022935 A1 | 3/2006 |
| WO | WO 2007/018640 A1 | 2/2007 |
| WO | WO 2007/071396 A2 | 6/2007 |
| WO | WO 2007/071400 A1 | 6/2007 |
| WO | WO 2008/013557 A1 | 1/2008 |
| WO | WO 2008/124491 A1 | 10/2008 |
| WO | WO 2008/135557 | 11/2008 |
| WO | WO 2009/074575 A2 | 6/2009 |
| WO | WO 2009/138378 A1 | 11/2009 |
| WO | WO 2009/139948 A1 | 11/2009 |
| WO | WO 2009/150137 A2 | 12/2009 |
| WO | WO 2011/028740 A1 | 3/2011 |
| WO | WO 2011/079087 A1 | 6/2011 |
| WO | WO 2011/113894 A1 | 9/2011 |
| WO | WO 2012/035158 A1 | 3/2012 |
| WO | WO 2013/003386 A1 | 1/2013 |
| WO | WO 2013/064450 A1 | 5/2013 |
| WO | WO 2013/092674 A1 | 6/2013 |
| WO | WO 2013/181232 A2 | 12/2013 |
| WO | WO 2014/044849 A1 | 3/2014 |
| WO | WO 2014/099673 A1 | 6/2014 |
| WO | WO 2014/099676 A1 | 6/2014 |
| WO | WO 2014/099705 A1 | 6/2014 |
| WO | WO 2014/177469 A1 | 11/2014 |
| WO | WO 2015/003083 A1 | 1/2015 |
| WO | WO 2015/003958 A1 | 1/2015 |
| WO | WO 2015/007516 A1 | 1/2015 |
| WO | WO 2015/007517 A1 | 1/2015 |
| WO | WO 2015/007519 A1 | 1/2015 |

(Continued)

OTHER PUBLICATIONS

App et al., "Acute and Long-Term Amiloride Inhalation in Cystic Fibrosis Lung Disease," *Am Rev Respir Dis.*, 141(3), pp. 605-612 (1990).

(Continued)

*Primary Examiner* — Bruck Kifle
(74) *Attorney, Agent, or Firm* — Bookoff McAndrews, PLLC

(57) ABSTRACT

The invention relates to compounds of general formula (I): wherein $R^1$, $R^2$, $R^3$, $R^{10}$ and $X^-$ are as defined herein. The compounds are inhibitors of the epithelial sodium channel (ENaC) and are useful for the treatment or prevention respiratory diseases and conditions.

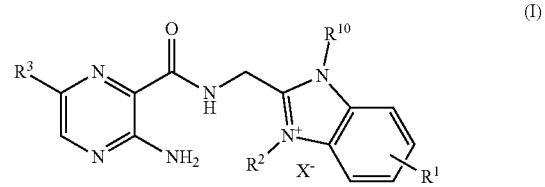

32 Claims, No Drawings

(56) References Cited

FOREIGN PATENT DOCUMENTS

| WO | WO 2015/018754 A1 | 2/2015 |
| WO | WO 2016/113167 A1 | 7/2016 |
| WO | WO 2017/028926 A1 | 2/2017 |
| WO | WO 2017/028927 A1 | 2/2017 |
| WO | WO 2018/096325 A1 | 5/2018 |

OTHER PUBLICATIONS

Botero-Valez et al., "Brief Report: Liddle's Syndrome Revisited—A Disorder of Sodium Reabsorption in the Distal Tubule," *The New England Journal of Medicine*, 330(3), pp. 178-181 (1994).

Boucher et al., "Evidence for Airway Surface Dehydration as the Initiating Event in CF Airway Disease," *Journal of Internal Medicine*, 261(1), pp. 5-16 (2007).

Bowler et al., "Nebulised Amiloride in Respiratory Exacerbations of Cystic Fibrosis: A Randomised Controlled Trial," *Archives of Disease in Childhood*, 73(5), pp. 427-430 (1995).

Chang et al., "Mutations in Subunits of the Epithelial Sodium Channel Cause Salt Wasting With Hyperkalaemic Acidosis, Pseudohypoaldosteronism Type 1," *Nature Publishing Group*, 12(3), pp. 248-253 (1996).

Coote et al., "Camostat Attenuates Airway Epithelial Sodium Channel Function In Vivo Through the Inhibition of a Channel-Activating Protease," *The Journal of Pharmacology and Experimental Therapeutics*, 329(2), pp. 764-774 (2009).

Coote et al., "The Guinea-Pig Tracheal Potential Difference as an In Vivo Model for the Study of Epithelial Sodium Channel Function in the Airways," *British Journal of Pharmacology*, 155(7), pp. 1025-1033 (2008).

Fajac et al., "Nasal Airway Ion Transport is Linked to the Cystic Fibrosis Phenotype in Adult Patients," *Thorax*, 59(11), pp. 971-976 (2004).

Frateschi et al., "The Epithelial Sodium Channel ENaC and its Regulators in the Epidermal Permeability Barrier Function," *The Open Dermatology Journal*, 4, pp. 27-35 (2010).

Graham et al., "No Added Benefit From Nebulized Amiloride in Patients With Cystic Fibrosis," *European Respiratory Journal*, 6(9), pp. 1243-1248 (1993).

Hirsh et al., "Pharmacological Properties of N-(3,5-Diamino-6-Chloropyrazine-2-Carbonyl)-N'-4-[4-(2,3-dihydroxypropoxy)phenyl]butyl-guanidine Methanesulfonate (552-02), a Novel Epithelial Sodium Channel Blocker with Potential Clinical Efficacy for Cystic Fibrosis Lung Disease," 325(1), pp. 77-88 (2008).

Kellenberger et al., "Epithelial Sodium Channel/Degenerin Family of Ion Channels: A Variety of Functions for a Shared Structure," *The American Physiological Society*, 82(3), pp. 735-767 (2002).

Kerem et al., "Pulmonary Epithelial Sodium-Channel Dysfunction and Excess Airway Liquid in Pseudohypoaldosteronism," *The New England Journal of Medicine*, 341(3), pp. 156-162 (1999).

Knowles et al., "A Pilot Study of Aerosolized Amiloride for the Treatment of Lung Disease in Cystic Fibrosis," *The New England Journal of Medicine*, 322 (17), pp. 1189-1194 (1990).

Knowles et al., "Abnormal Ion Permeation Through Cystic Fibrosis Respiratory Epithelium," *Science*, 221 (4615), pp. 1067-1070 (1983).

Leal et al., "Airway Ion Transport Impacts on Disease Presentation and Severity in Cystic Fibrosis," *Clinical Biochemistry*, 41(10-11), pp. 764-772 (2008).

Matsui et al., "Evidence for Periciliary Liquid Layer Depletion, Not Abnormal Ion Composition, in the Pathogenesis of Cystic Fibrosis Airways Disease," *Cell*, 95(7), pp. 1005-1015 (1998).

Middleton et al., "Effect of Amiloride and Saline on Nasal Mucociliary Clearance and Potential Difference in Cystic Fibrosis and Normal Subjects," *Thorax*, 48(8), pp. 812-816 (1993).

Noone et al., "Airway Deposition and Clearance and Systemic Pharmacokinetics of Amiloride Following Aerosolization With an Ultrasonic Nebulizer to Normal Airways," *Chest*, 112(5), pp. 1283-1290 (1997).

Perazella, "Drug-induced Hyperkalemia: Old Culprits and New Offenders," *The American Journal of Medicine*, 109(4), pp. 307-314 (2000).

Pons et al., "French Multicenter Randomized Double-Blind Placebo-Controlled Trial on Nebulized Amiloride in Cystic Fibrosis Patients," *Pediatric Pulmonology*, 30(1), pp. 25-31 (2000).

Thelin et al., "Effect of Topically Applied Epithelial Sodium Channel Inhibitors on Tear Production in Normal Mice and in Mice With Induced Aqueous Tear Deficiency," *Journal of Ocular Pharmacology and Therapeutics*, 28(4), pp. 433-438 (2012).

International Search Report for PCT/GB2017/051815 dated Aug. 11, 2017 (3 pages).

COMPOUNDS

This application is a U.S. National Stage filing under 35 U.S.C. § 371 of International Application No. PCT/GB2017/051815, filed on Jun. 21, 2017, which claims priority to United Kingdom Application No. GB 1610854.0, filed on Jun. 21, 2016.

The present invention relates to novel compounds which have activity as inhibitors of the epithelial sodium channel (ENaC). The invention also relates to the use of these compounds in treating diseases and conditions modulated by ENaC, particularly respiratory diseases and conditions, dry eye disease, atopic dermatitis and psoriasis. The invention also relates to methods of preparing the compounds and pharmaceutical compositions containing them.

Humans can inhale up to 12,000 L of air each day and with it comes the potential for airborne pathogens (bacteria, viruses, fungal spores). To protect against these airborne pathogens, the lung has evolved innate defense mechanisms to minimise the potential for infection and colonisation of the airways. One such mechanism is the mucus clearance system, whereby secreted mucus is propelled up and out of the airways by the coordinated beating of cilia together with cough clearance. This ongoing 'cleansing' of the lung constantly removes inhaled particles and microbes thereby reducing the risk of infection.

In recent years it has become clear that the hydration of the mucus gel is critical to enable mucus clearance (Boucher 2007; Matsui et al, 1998). In a normal, healthy airway, the mucus gel is typically 97% water and 3% solids under which conditions the mucus is cleared by mucociliary action. The hydration of the airway mucosa is regulated by the coordinated activity of a number of ion channels and transporters. The balance of anion ($Cl^-/HCO_3^-$) secretion mediated via the Cystic Fibrosis Transmembrane Conductance Regulator (CFTR) and the Calcium Activated Chloride Conductance (CaCC; TMEM16A) and $Na^+$ absorption through the epithelial $Na^+$ channel (ENaC) determine the hydration status of the airway mucosa. As ions are transported across the epithelium, water is osmotically obliged to follow and thus fluid is either secreted or absorbed.

In respiratory diseases such as chronic bronchitis and cystic fibrosis, the % solids of the mucus gel is increased as the hydration is reduced and mucus clearance is reduced (Boucher, 2007). In cystic fibrosis, where loss of function mutations in CFTR attenuates ability of the airway to secrete fluid, the % solids can be increased to 15% which is believed to contribute towards the plugging of small airways and failure of mucus clearance. Furthermore, in cystic fibrosis an increase in ENaC activity has been reported by several groups (Knowles et al, 1983; Middleton et al, 1993) and this increase in ENaC function has been shown to correlate with disease severity (Fajac et al, 2004; Leal et al, 2008). Strategies to increase the hydration of the airway mucus include either the stimulation of anion and thereby fluid secretion or the inhibition of $Na^+$ absorption. To this end, blocking the activity of ENaC will inhibit $Na^+$ absorption and therefore increase fluid accumulation in the airway mucosa, hydrate mucus and enhance mucus clearance mechanisms.

ENaC is expressed in renal, colonic, corneal, sweat duct and respiratory epithelia where it forms a low conductance channel (~4 pS) with a selectivity for $Na^+$ over $K^+$ of approximately 10-fold (Kellenberger 2002). Loss and gain of function mutations in the channel can cause human disease including pseudohypoaldosteronism type 1 (PHA1), a salt wasting disease (Chang et al, 1996), and Liddle's syndrome, a disease associated with salt retention and hypertension (Botero-Velez et al, 1994). Of particular note to lung physiology is the observation that patients with PHA1 loss-of-function mutations in ENaC have an enhanced rate of airway mucociliary clearance (MCC) compared with the normal healthy population, typically 3-4 fold faster (Kerem et al, 1999). Furthermore the upper airways of these patients appear to be 'wet' and have extra-hydration compared to normal. These observations further support the salient role that ENaC plays in the human airway in the regulation of hydration and the therapeutic benefit that blocking ENaC in the airway could deliver in terms of enhancing MCC and innate defense.

Amiloride, a small compound blocker of ENaC, has been demonstrated to increase MCC in both healthy controls and also patients with CF, further supporting the physiological significance of this mechanism (App et al, 1990). However the lack of a robust effect of inhaled amiloride on clinical endpoints (Bowler et al, 1995; Graham et al, 1993; Knowles et al, 1990; Pons et al, 2000) was ascribed to the short duration of action of this compound in the lungs (Noone et al., 1997). Novel ENaC blockers, specifically designed for a long duration of action in the airway are therefore predicted to acutely provide an extended enhancement of MCC with resulting clinical benefit in the longer term.

A challenge with the design of inhaled ENaC blockers for the treatment of respiratory diseases has been the potential for the renal-based side effect of hyperkalaemia (Perazela et al., 2000). ENaC is expressed in the cortical collecting duct of the kidney epithelium and blockade of the channel here can lead to a systemic accumulation of $K^+$. For this reason, it is desirable that an inhaled ENaC blocker avoids renal exposure following absorption from the lung. This could be achieved through either a high lung retention of ENaC blocker therefore enabling only a low dose to be administered or through the design of a compound that will be rapidly broken down before it reaches the kidney.

ENaC is also expressed by the ocular epithelium and is implicated in controlling the hydration status of the eye. Analogous to its function in the respiratory epithelium, ENaC is proposed as an absorptive pathway in the corneal/conjunctival epithelium. Thus, inhibition of ENaC is expected to produce an increase in tear volume and ocular hydration. Dry eye (keratoconjunctivitis sicca) is a common disorder, associated with numerous medical conditions includiung Sjögren's syndrome, lupus and allergic conjunctivitis, and is characterised by the production of an inadequate quantity or quality of tears. Studies in pre-clinical models suggest ENaC blockers represent a novel pharmacological approach to the treatment of chronic dry eye (Thelin et al, 2012).

ENaC has also been implicated in controlling the hydration and barrier function of skin, offering a novel approach to the treatment of diseases where these are compromised such as atopic dermatitis and psoriasis (Fratechi et al, 2010).

Several ENaC blockers are known. For example, WO 2011/079087 relates to compounds of the formula:

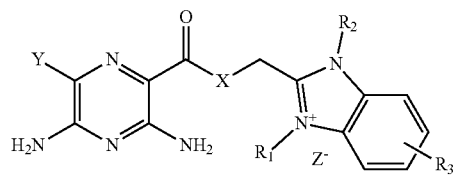

WO 2015/007516, WO 2015/007517 and WO 2015/007519 all relate to compounds of the formula:

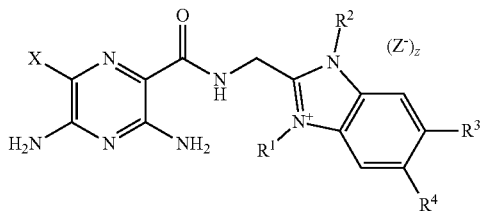

The compounds described in these documents all contain a 3,5-diaminopyrazine group and this group is also a structural feature of the ENaC inhibitors disclosed in numerous other documents including WO2013/0664450, WO2013/092674, WO2014/044849, WO 2014/177469, WO 2015/003958, WO2015/018754, WO 2011/028740, WO 2007/071396, WO 2007/071400, WO 2008/135557, WO 2009/074575, WO 2009/138378, WO 2009/150137 and WO 2012/035158. A number of other prior art documents mention the possibility of an alternative substituent at the 5-position of the pyrazine ring. These include WO 2015/003083, WO 2004/073629, WO 03/070184, WO 03/070182, WO 2006/022935, WO 2007/018640, WO 2008/124491, WO 2009/139948, WO 2005/044180, WO 2005/016879, WO 2005/018644, WO 2005/025496, WO 2005/034847 and WO 2013/181232. However, every compound exemplified in these documents contains a 3,5-diaminopyrazine group and it is therefore clear that a pyrazine ring with amino substituents at the 3- and 5-positions is considered essential for ENaC blocking activity.

WO 2011/113894 relates to compounds which are said to be of use for treating inflammatory or obstructive diseases of the airways or for promoting mucosal hydration. The compounds are of the formula:

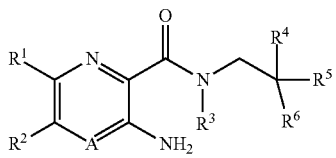

where A is N or $CR^{4a}$ and $R^2$ is haloalkyl. None of the compounds exemplified in this document contain a benzodiazole moiety.

WO 2017/028926 relates to ENaC inhibiting compounds of the formula:

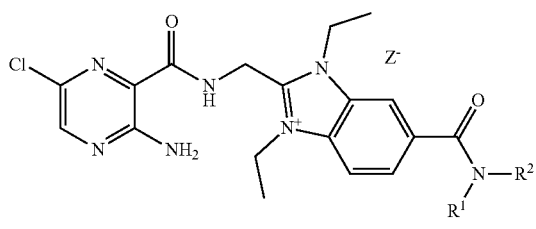

and WO 2017/028927 relates to ENaC inhibiting compounds of the formula:

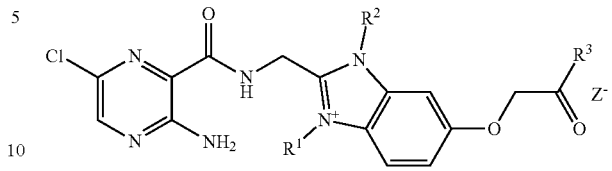

These compounds are said to shown ENaC inhibiting activity in spite of the lack of an amino substituent at the 5-position of the pyrazine moiety.

Surprisingly, the present inventors have further compounds which lack an amino substituent at the 5-position of the pyrazine ring but which retain ENaC blocking activity. Furthermore, some of these compounds have the advantage of more rapid metabolism than the equivalent 3,5-diaminopyrazine compounds, meaning that if they are administered directly to the airways and lungs, they may be substantially metabolised before they reach the kidneys or the colon, thus minimising side effects of the therapy.

In the present invention there is provided a compound of general formula (I) including all tautomeric forms, all enantiomers and isotopic variants thereof:

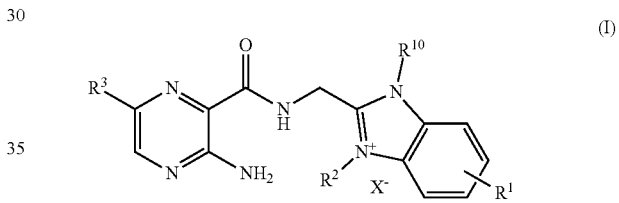

wherein:
$X^-$ is an anion;
$R^1$ is:
i. H, halo; or
ii. $C_{1-6}$ alkyl, $C_{2-6}$ alkenyl, $C_{2-6}$ alkynyl, —O($C_{1-6}$ alkyl), —O($C_{2-6}$ alkenyl) or —O($C_{2-6}$ alkynyl) any of which is optionally substituted by one or more halo substituents; or
iii -$L^1R^{11}$, —O-$L^1R^{11}$, —$OR^5$, —$SO_2R^5$, —$C(O)OR^5$, —$C(O)NR^5R^6$ or —$C(=NR^7)NR^5R^6$;
$L^1$ is $C_{1-6}$ alkylene, $C_{2-6}$ alkenylene or $C_{2-6}$ alkynylene;
$R^{11}$ is H, —$NR^7R^8$, —$NR^7$—$C(=NR^9)N(R^8)_2$, —$NR^7$—$C(O)O$—$R^8$, —$NR^7$—$C(O)$—$(C_{1-3}$ alkylene)—$N(R^8)_3$ or —$N^+(R^8)_3$;
each $R^7$, $R^8$ and $R^9$ is independently selected from H or $C_{1-4}$ alkyl;
each $R^5$ and $R^6$ is independently H, $C_{1-6}$ alkyl, $C_{2-6}$ alkenyl, $C_{2-6}$ alkynyl, $C_{3-8}$ cycloalkyl or $C_{3-8}$ heterocyclyl, any of which is optionally substituted by one or more substituents selected from halo, $OR^7$, $C(O)OR^7$, —$NR^7R^8$, $C(O)NR^7R^8$ or, in the case of cycloalkyl or heterocyclyl groups, oxo; or
iv. -$L^2$-$R^{12}$ wherein
$L^2$ is:
a bond;
—$Z_{12}$—, -aryl-, -heteroaryl-, -carbocyclyl-, -heterocyclyl-,
—$Z_6$-carbocyclyl-, —$Z_6$-heterocyclyl-, —$Z_6$-aryl-, —$Z_6$-heteroaryl-;

carbocyclyl-$Z_6$—, -heterocyclyl-$Z_6$—, -aryl-$Z_6$—, -heteroaryl-$Z_6$—;
—$Z_6$—$NR^7$—$Z_6$—;
—$OZ_{12}$—, —O-aryl-, —O-heteroaryl-, —O-carbocyclyl-, —O-heterocyclyl-,
—$OZ_6$-carbocyclyl-, —$OZ_6$-heterocyclyl-, —$OZ_6$-aryl-, —$OZ_6$-heteroaryl-;
—O-carbocyclyl-$Z_6$—, —O-heterocyclyl-$Z_6$—, —O-aryl-$Z_6$—, —O-heteroaryl-$Z_6$—;
—$OZ_6$—$NR^7$—$Z_6$—,
—$C(O)Z_{12}$—, —C(O)-carbocyclyl-, —C(O)-heterocyclyl-, —C(O)-carbocyclyl-$Z_6$—, —C(O)—heterocyclyl-$Z_6$—, —C(O)—$Z_6$-carbocyclyl-, C(O)—$Z_6$-heterocyclyl-, —C(O)—$Z_6$-carbocyclyl-$Z_6$—, C(O)—$Z_6$-heterocyclyl-$Z_6$—,
—$C(O)NR^7$—, —$C(O)NR^7$—$Z_{12}$—, —$C(O)NR^7$-carbocyclyl-, $C(O)NR^7$-heterocyclyl-, $C(O)NR^7$-aryl-, $C(O)NR^7$-heteroaryl-, —$C(O)NR^7$-carbocyclyl-$Z_6$—, —C(O)NH—heterocyclyl-$Z_6$—, —$C(O)NR^7$—$Z_6$-carbocyclyl-, —$C(O)NR^7$—$Z_6$-heterocyclyl-, —$C(O)NR^7$—$Z_6$-carbocyclyl-$Z_6$—, —C(O)NR—$Z_6$-heterocyclyl-$Z_6$—;
—$Z_6$—$C(O)NR^7$—$Z_6$—, —$Z_6$—$C(O)NR^7$-aryl-, —$Z_6$—$C(O)NR^7$-heteroaryl-, —$Z_6$—$C(O)NR^7$-carbocyclyl-, —$Z_6$—$C(O)NR^7$-heterocyclyl-, —$Z_6$—$C(O)NR^7$-aryl-$Z_6$—, —$Z_6$—$C(O)NR^7$-heteroaryl-$Z_6$—, —$Z_6$—$C(O)NR^7$-carbocyclyl-$Z_6$— or —$Z_6$—$C(O)NR^7$-heterocyclyl-$Z_6$—;
—$C(O)Z_{12}$—, —C(O)-carbocyclyl-, —C(O)-heterocyclyl-, —C(O)-carbocyclyl-$Z_6$—, —C(O)— heterocyclyl-$Z_6$—, —C(O)—$Z_6$-carbocyclyl-, C(O)—$Z_6$-heterocyclyl-, —C(O)—$Z_6$-carbocyclyl-$Z_6$—, C(O)—$Z_6$-heterocyclyl-$Z_6$—,
—$C(=N)NR^7$—$Z_{12}$—, —$C(=N)NR^7$-carbocyclyl-, $C(=N)NR^7$-heterocyclyl-, —$C(=N)NR^7$-carbocyclyl-$Z_6$—, —C(=N)N H-heterocyclyl-$Z_6$—, —$C(=N)NR^7$—$Z_6$-carbocyclyl-, —$C(=N)NR^7$—$Z_6$-heterocyclyl-, —$C(=N)NR^7$—$Z_6$-carbocyclyl-$Z_6$—, —$C(=N)NR^7$—$Z_6$-heterocyclyl-$Z_6$—;
wherein $Z_{12}$ is $O_{1-12}$ alkylene, $C_{2-12}$ alkenylene or $C_{2-12}$ alkynylene; $Z_6$ is $C_{1-6}$ alkylene, $C_{2-6}$ alkenylene or $C_{2-6}$ alkynylene and alkylene, alkenylene and alkynylene groups are optionally substituted with one or more substituents selected from $NR^8R^9$, $C(O)NR^8R^9$, OH or halo, wherein $R^7$, $R^8$ and $R^9$ are as defined above;

$R^{12}$ is —$NR^{14}R^{15}$ or -G-$R^{14}$
each of $R^{14}$ and $R^{15}$ is independently $C_{1-8}$ alkyl optionally substituted with one or more OH groups; and G is a 5- to 10-membered heterocyclic ring optionally substituted with one or more OH groups and containing at least one nitrogen atom which is connected by a covalent bond to the group $R^{14}$;

v. -$L^3$-$R^{13}$, wherein
$L^3$ comprises one or two cyclic groups directly linked to one another wherein each cyclic group is selected from aryl, heteroaryl, carbocyclyl and heterocyclyl, wherein cycloalkyl and heterocyclyl groups may have one or more oxo substituents; and
$R^{13}$ is H, —$OR^5$, —$SO_2R^5$, —$C(O)OR^5$, —$C(O)NR^5R^6$ or —$C(=NR^7)NR^5R^6$; wherein $R^5$, $R^6$ and $R^7$ are as defined above;
$R^2$ is $C_{1-10}$ alkyl, wherein one or more —$CH_2$— groups is optionally replaced by —O— and which is optionally substituted with one or more substituents selected from halo, aryl, heteroaryl, —$OR^7$ and —$NR^7R^8$, wherein $R^7$ and $R^8$ are as defined above;

$R^3$ is H, halo, cyano, $C_{1-3}$ alkyl, $C_{1-3}$ haloalkyl, or —$S(C_{1-3}$ alkyl);
$R^{10}$ is $C_{1-6}$ alkyl optionally substituted with one or more substituents selected from halo, —$OR^7$ and —$NR^7R^8$, wherein $R^7$ and $R^8$ are as defined above;
provided that
when $R^2$ is ethyl; $R^3$ is chloro and $R^{10}$ is ethyl:
$R^1$ is not $C(O)NR^5R^6$, wherein at least one of $R^5$ and $R^6$ is $C_{1-6}$ alkyl substituted with one or more substituents selected from OH and $NR^7R^8$, where $R^7$ and $R^8$ are each independently H or methyl; and
$R^1$ is not $L^2R^{12}$ where $L^2$ is C(O)heterocyclyl and $R^{12}$ is $N(CH_3)_2$.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

The anion $X^-$ can have any negative charge and will be balanced by the appropriate number of cations. Thus, for example, a compound of general formula (I) in which $X^-$ is an anion having a single negative charge will have a 1:1 ratio of cation:anion whereas if the anion $X^-$ has a charge of −2, the ratio of cation:anion in the compound of general formula (I) will be 2:1. The anion $X^-$ is suitably a pharmacologically acceptable anion, although other anions may also be useful, particularly in synthetic precursors to the compounds of general formula (I). Suitable anions, $X^-$ include halide, hydroxide, sulfate, nitrate, phosphate, formate, acetate, trifluoroacetate, fumarate, citrate, tartrate, oxalate, succinate, mandelate, methane sulfonate and p-toluene sulfonate.

In the present specification, the term "$C_{1-6}$" alkyl refers to a straight or branched fully saturated hydrocarbon group having from 1 to 6 carbon atoms. The term encompasses methyl, ethyl, n-propyl, isopropyl, n-butyl, isobutyl and t-butyl. Other alkyl groups, for example $C_{1-4}$ alkyl are as defined above but contain different numbers of carbon atoms.

The term "$C_{2-6}$ alkenyl" refers to a straight or branched hydrocarbon group having from 2 to 6 carbon atoms and at least one carbon-carbon double bond. Examples include ethenyl, prop-1-enyl, hex-2-enyl etc. Other alkylene groups, for example $C_{1-3}$ alkylene are as defined above except that they contain the specified number (e.g. 1 to 3) carbon atoms.

The term "$C_{2-6}$ alkynyl" refers to a straight or branched hydrocarbon group having from 2 to 6 carbon atoms and at least one carbon-carbon triple bond. Examples include ethynyl, prop-1-ynyl, hex-2-ynyl etc. Other alkylene groups, for example $C_{2-3}$ alkylene are as defined above except that they contain the specified number (e.g. 2 to 3) carbon atoms.

The term "$C_{1-6}$ alkylene" refers to a straight or branched fully saturated hydrocarbon chain having from 1 to 6 carbon atoms. Examples of alkylene groups include —$CH_2$—, —$CH_2CH_2$—, $CH(CH_3)$—$CH_2$—, $CH_2CH(CH_3)$—, —$CH_2CH_2CH_2$—, —$CH_2CH(CH_2CH_3)$— and —$CH_2CH(CH_2CH_3)CH_2$—. Other alkylene groups, for example $C_{1-3}$ alkylene are as defined above except that they contain the specified number (e.g. 1 to 3) carbon atoms.

The term "$C_{2-6}$ alkenylene" refers to a straight or branched hydrocarbon chain containing from 2 to 6 carbon atoms and at least one carbon-carbon double bond. Examples of alkenylene groups include —CH=CH—, —CH=$C(CH_3)$—, —$CH_2CH$=CH—, —CH=$CHCH_2$—, $CH_2CH_2CH$=CH—, $CH_2CH$=$C(CH_3)$— and —$CH_2CH$=$C(CH_2CH_3)$—. Other alkenylene groups, for example C$_{2-3}$ alkenylene, are as defined above except that they contain the specified number (e.g. 2 to 3) carbon atoms.

The term "C$_{2-6}$ alkynylene" refers to a straight or branched hydrocarbon chain containing from 2 to 6 carbon atoms and at least one carbon-carbon triple bond. Examples of alkenylene groups include —C≡C—, —CH$_2$C≡C—, —C≡C—CH$_2$—, CH$_2$CH$_2$C≡C—, CH$_2$C≡CCH$_2$— and —CH$_2$CH≡C—CH$_2$CH$_2$—)—. Other alkynylene groups, for example C$_{2-3}$ alkynylene, are as defined above except that they contain the specified number (e.g. 2 to 3) carbon atoms.

The terms "carbocyclic" and "carbocyclyl" refer to a non-aromatic hydrocarbon ring system containing from 3 to 10 ring carbon atoms, unless otherwise indicated, and optionally one or more double bond. The carbocyclic group may be a single ring or may contain two or three rings which may be fused or bridged. Examples include cyclopropyl, cyclobutyl, cyclopentyl, cyclohexyl, cyclopentenyl and cyclohexenyl.

In the context of the present specification, the terms "heterocyclic" and "heterocyclyl" refer to a non-aromatic ring system containing 3 to 10 ring atoms including at least one heteroatom selected from N, O and S. The heterocyclic group may be a single ring or may contain two or three rings which may be fused or bridged. Examples include tetrahydrofuranyl, tetrahydroypranyl, pyrrolidine, piperidinyl, morpholinyl, piperazinyl and thiomorpholinyl.

The terms "aryl" and "aromatic" in the context of the present specification refer to a ring system with aromatic character having from 5 to 14 ring carbon atoms and containing up to three rings. Where an aryl group contains more than one ring, not all rings must be fully aromatic in character. Examples of aromatic moieties are benzene, naphthalene, fluorene, indane and indene.

The terms "heteroaryl" and "heteroaromatic" in the context of the specification refer to a ring system with aromatic character having from 5 to 14 ring atoms, at least one of which is a heteroatom selected from N, O and S, and containing up to three rings. Where a heteroaryl group contains more than one ring, not all rings must be fully aromatic in character. Examples of heteroaryl groups include pyridine, pyrimidine, indole, benzofuran, benzimidazole and indolene.

The term "halogen" refers to fluorine, chlorine, bromine or iodine and the term "halo" to fluoro, chloro, bromo or iodo groups. Similarly, "halide" refers to fluoride, chloride, bromide or iodide.

The term "C$_{1-6}$ haloalkyl" as used herein refers to a C$_{1-6}$ alkyl group as defined above in which one or more of the hydrogen atoms is replaced by a halo group. Any number of hydrogen atoms may be replaced, up to perhalo substitution. Examples include trifluoromethyl, chloroethyl and 1,1-difluoroethyl.

The term "oxo" refers to a substituent =O where the double bond is to a carbon atom in the ring or chain substituted with the oxo substituent so as to form a carbonyl moiety.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as 2H (deuterium), 3H, 11C, 13C, 14C, 18F, 123I or 125I (e.g. 3H, 11C, 14C, 18F, 123I or 125I), which may be naturally occurring or non-naturally occurring isotopes.

The concept of canonical forms is well understood by the person of skill in the art. Thus, a compound of general formula (I) can be represented as the following canonical forms:

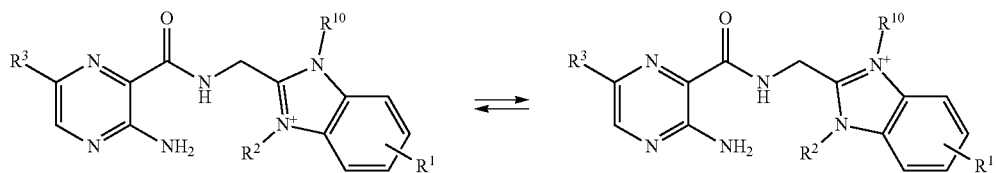

both of which are included within the scope of the invention.

In some suitable compounds of the present invention, when R$^2$ is ethyl, R$^3$ is chloro and R$^{10}$ is ethyl:

R$^1$ is not C(O)NR$^5$R$^6$ or L$^2$R$^{12}$ where L$^2$ is C(O)heterocyclyl and R$^{12}$ is N(CH$_3$)$_2$.

In the compounds of the present invention, the R$^1$ substituent is suitably at the 5- or the 6-position and thus the compound of general formula (I) can be a compound of general formula (IC):

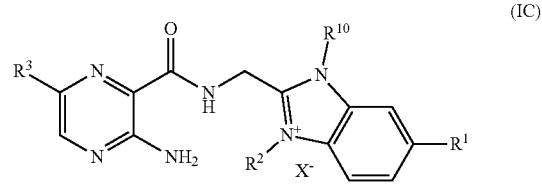

(IC)

wherein R$^1$, R$^2$, R$^3$, R$^{10}$ and X$^-$ are as defined for general formula (I);

or a compound of general formula (ID):

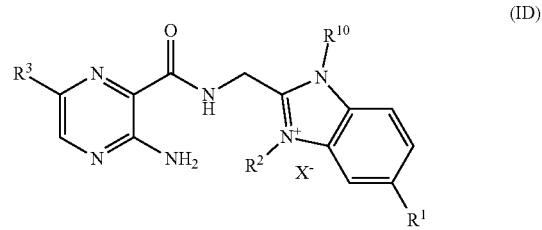

(ID)

wherein R$^1$, R$^2$, R$^3$, R$^{10}$ and X$^-$ are as defined for general formula (I).

Compounds of general formula (IC) are particularly suitable.

In some suitable compounds of general formula (I), $R^1$ is: H, halo; or $C_{1-6}$ alkyl, $C_{2-6}$ alkenyl, $C_{2-6}$ alkynyl, —O($C_{1-6}$ alkyl), —O($C_{2-6}$ alkenyl) or —O($C_{2-6}$ alkynyl), any of which is optionally substituted by one or more halo substituents.

More suitably in these compounds, $R^1$ is H, halo, $C_{1-6}$ alkyl, $C_{1-6}$ haloalkyl, $C_{1-6}$ alkoxy or $C_{1-6}$ haloalkoxy.

Examples of such $R^1$ groups include H, chloro, methyl, trifluoromethyl, methoxy and trifluoromethoxy.

In other suitable compounds of general formula (I), $R^1$ is -$L^1R^{11}$, —O-$L^1R^{11}$, —$OR^5$—$SO_2R^5$, —C(O)$OR^5$, —C(O)$NR^5R^6$ or —C(=$NR^7$)$NR^5R^6$; wherein $L^1$, $R^{11}$, $R^5$, $R^6$ and $R^7$ are as defined above.

Suitably, $L^1$ is $C_{1-6}$ alkylene, more suitably $C_{1-4}$ alkylene.

In some suitable compounds wherein $R^1$ is -$L^1R^{11}$, $L^1$ is —($CH_2$)$_n$— where n is 1 to 6.

In some suitable compounds where $R^1$ is —O-$L^1$-$R^{11}$, $L^1$ is —($CH_2$)$_m$—, where m is 1 to 5.

Still more suitably, n is 1 to 4 and m is 1 to 3. Examples of $L^1$ and $OL^1$ groups include —$CH_2$—$CH_2$—, —$CH_2$—$CH_2$—$CH_2$—, —$CH_2$—$CH_2$—$CH_2$—$CH_2$—, —O—$CH_2$—, —O—$CH_2$—$CH_2$— and —O—$CH_2$—$CH_2$—$CH_2$—.

Suitably, $R^{11}$ is H, —$NR^7R^8$, —$NR^7$—C(=$NR^9$)N($R^8$)$_2$, —$NR^7$—C(O)O—$R^8$, —$NR^7$—C(O)—($C_10.3$ alkylene)-$N^+$($R^8$)$_3$ or —$N^+$($R^8$)$_3$ where each $R^7$, $R^8$ and $R^9$ is selected from H and $C_{1-4}$ alkyl.

More suitably, $R^7$ is H, each $R^8$ is independently H or $C_{1-4}$ alkyl and $R^9$ is H.

When $R^{11}$ is —$NR^7$—C(O)—($C_{1-3}$ alkylene)-$N^+$($R^8$)$_3$, the $C_{1-3}$ alkylene group is suitably —$CH_2$— or —$CH_2$—$CH_2$—, particularly —$CH_2$—.

Examples of such $R^{11}$ groups include —$NH_2$, —NH—C(=NH)$NH_2$, —NH—C(O)O—C($CH_3$)$_3$, —NH—C(O)—$CH_2$—$N^+$($CH_3$)$_3$ and —$N^+$($CH_3$)$_3$.

When $R^1$ is —$OR^5$, —C(O)$OR^5$, —C(O)$NR^5R^6$ or —C(=$NR^7$)$NR^5R^6$, suitable $R^5$ and $R^6$ groups include H and $C_{1-6}$ alkyl.

When $R^1$ is —$SO_2R^5$, it is preferred that $R^5$ is not H as these compounds may be unstable. Therefore, when $R^1$ is —$SO_2R^5$, suitably $R^5$ is $C_{1-6}$ alkyl.

Alternatively, $R^6$ (when present) may be H and $R^5$ may be a cyclic group, for example a 5- or 6-membered carbocyclic or heterocyclic group optionally substituted with an oxo, for example a lactone such as gamma-butyrolactone, tetrahydrofuran, pyrrolidine, piperidine or piperazine group.

Examples of $R^1$ groups of this type include —$OCH_3$, —$OCF_3$, —C(O)$OCH_3$, —C(O)OH, —NH—C(O)O—C($CH_3$)$_3$, —C(=NH)$NH_2$, —$SO_2$—$CH_3$, —C(O)N($CH_3$)$_2$ and:

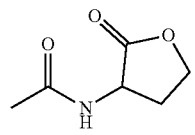

In other compounds of general formula (I), $R^1$ is -$L^2$-$R^{12}$ wherein $L^2$ and $R^{12}$ are as defined above. Suitably, in the linker group $L^2$, independently or in any combination:
$R^7$ is H;
carbocyclyl and heterocyclyl groups are 5- or 6-membered rings, suitably 6-membered rings;
the aryl group is phenyl;
heteroaryl groups are 5- or 6-membered nitrogen containing heteroaryl groups; $Z_{12}$ and $Z_6$ are alkylene groups optionally substituted as described above.

More suitably in the linker $L^2$, independently or in any combination:
$R^7$ is H;
heterocyclyl groups are piperidinyl groups;
the heteroaryl group is:

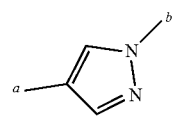

where a is the link to the remainder of the molecule and b is the link to $R^{12}$.

Where $Z_{12}$ and $Z_6$ groups are substituted as described above, more suitable substituents include —$NH_2$, —N($CH_3$)$_2$, —C(O)$NH_2$, —C(O)N($CH_3$)$_2$, OH and halo.

More suitable substituents include —$NH_2$, —C(O)$NH_2$, OH and halo.

The linker $L^2$ is suitably
a bond;
$Z_{12}$—, -aryl-, -heteroaryl-, -carbocyclyl-, -heterocyclyl-, —$Z_6$-carbocyclyl-, —$Z_6$-heterocyclyl-, —$Z_6$-aryl-, —$Z_6$-heteroaryl-;
carbocyclyl-$Z_6$—, -heterocyclyl-$Z_6$—, -aryl-$Z_6$—, -heteroaryl-$Z_6$—;
—$Z_6$—$NR^7$—$Z_6$—;
—$OZ_{12}$—, —O-aryl-, —O-heteroaryl-, —O-carbocyclyl-, —O-heterocyclyl-,
—$OZ_6$-carbocyclyl-, —$OZ_6$-heterocyclyl-, —$OZ_6$-aryl-, —$OZ_6$-heteroaryl-;
—O-carbocyclyl-$Z_6$—, —O-heterocyclyl-$Z_6$—, —O-aryl-$Z_6$—, —O-heteroaryl-$Z_6$—;
—$OZ_6$—$NR^7$—$Z_6$—,
—C(O)-heterocyclyl-, —C(O)-heterocyclyl-$Z_6$—,
—C(O)$NR^7$—, —C(O)$NR^7$—$Z_{12}$—, —C(O)$NR^7$—$Z_6$-heterocyclyl-, —C(O)$NR^7$—$Z_6$-carbocyclyl-$Z_6$—, —C(O)$NR^7$—$Z_6$-heterocyclyl-$Z_6$—;
—$Z_6$—C(O)$NR^7$—$Z_6$—, —$Z_6$—C(O)$NR^7$-aryl-, —$Z_6$—C(O)$NR^7$-heteroaryl-, —$Z_6$—C(O)$NR^7$—$Z_6$—C(O)$NR^7$-aryl-$Z_6$—, —$Z_6$—C(O)$NR^7$-heteroaryl-$Z_6$—;
wherein $Z_{12}$ and $Z_6$ groups are optionally substituted as described above.

More suitably, the linker $L^2$ is:
a bond;
—$Z_{12}$—, -aryl-, -heteroaryl-,
—$Z_6$—$NR^7$—$Z_6$—;
—$OZ_{12}$—,
—$OZ_6$—$NR^7$—$Z_6$—,
—C(O)-heterocyclyl-, —C(O)-heterocyclyl-$Z_6$—,
—C(O)$NR^7$—, —C(O)$NR^7$—$Z_{12}$—, —C(O)$NR^7$—$Z_6$-heterocyclyl-, —C(O)$NR^7$—Z-heterocyclyl-$Z_6$—;
—$Z_6$—C(O)$NR^7$—, —$Z_6$—C(O)$NR^7$-aryl-$Z_6$—, —$Z_6$—C(O)$NR^7$-heteroaryl-$Z_6$—;
wherein $Z_{12}$ and $Z_6$ groups are optionally substituted as described above.

In these $L^2$ groups, suitable $R^7$, $Z_{12}$, $Z_6$, carbocyclyl, heterocyclyl, aryl and heteroaryl groups are as defined above.

Examples of $L^2$ linkers include:
A bond
—$OCH_2CH_2$—
—$CH_2CH_2CH_2$—

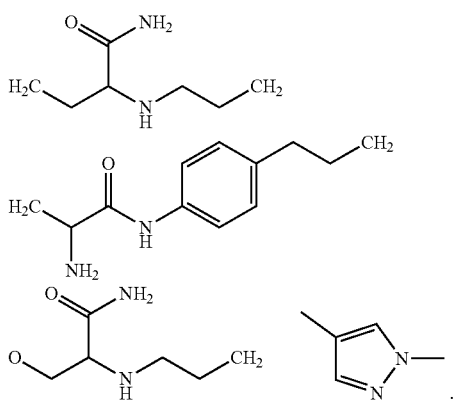

In the compounds of general formula (I), $R^{12}$ is —$NR^{14}R^{15}$ or -G-$R^{14}$ where G is a 5- to 10-membered heterocyclic ring optionally substituted with one or more OH groups and containing at least one nitrogen atom which is connected by a covalent bond to the group $R^{14}$.

Suitably, G is a 5- or 6-membered heterocyclic ring, more suitably piperidinyl, for example:

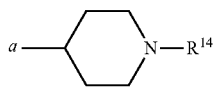

where the piperidinyl group is joined to $L^2$ at a.

Suitably, each of $R^{14}$ and $R^{15}$ is independently $C_{4-8}$ alkyl optionally substituted with one or more OH groups.

Suitably, $R^{14}$ and optionally $R^{15}$ comprises two or more OH groups or three or more OH groups. Typically, in this case, when $R^{14}$ and/or $R^{15}$ is $C_4$ alkyl it will have three OH substituents; when $R^{14}$ and/or $R^{15}$ is $C_5$ alkyl it will have four OH substituents; when $R^{14}$ and/or $R^{15}$ is $C_6$ alkyl it will have five OH substituents; when $R^{14}$ and/or $R^{15}$ is $C_7$ alkyl it will have six OH substituents; and when $R^{14}$ and/or $R^{15}$ is $C_8$ alkyl it will have seven OH substituents.

In some compounds, when $R^{12}$ is —$NR^{14}R^{15}$, both $R^{14}$ and $R^{15}$ comprise a plurality of OH groups as discussed above.

In some other compounds, when $R^{12}$ is —$NR^{14}R^{15}$, one of $R^{14}$ and $R^{15}$ has one or more OH substituents, suitably two or more OH groups, and the other of when $R^{14}$ and $R^{15}$ is unsubstituted. In other compounds both $R^{14}$ and $R^{15}$ contain one or more OH substituents.

In other compounds of general formula (I), $R^1$ is -$L^3$-$R^{13}$, wherein $L^3$ and $R^{13}$ are as defined above.

Suitably, $L^3$ comprises a carbocyclic or heterocyclic group optionally linked to an aryl or heteroaryl group. Typically, both the carbocyclic or heterocyclic group and the aryl or heteroaryl group will be 5- or 6-membered rings.

More suitably, $L^3$ comprises a heterocyclic group, especially a nitrogen-containing heterocyclic group optionally linked to an aryl or heteroaryl group.

Examples of suitable nitrogen containing heterocyclic groups include piperidine, piperazine and pyrrolidine, more suitably piperazine and piperidine and particularly piperidine.

When the nitrogen containing heterocyclic group is piperidine or piperazine, the $R^{13}$ group is suitably attached to the nitrogen at the 1-position and the piperidine or piperazine ring is linked via the 4-position to the remainder of the molecule or (when present) to the aryl group which comprises the remainder of the $L^3$ linker. When the heterocylic group is piperazine linked via the 4-position to a heteroaryl group, it will be linked to a carbon atom of the heteroaryl group. When the heterocyclic group is piperidine linked to a heteroaryl group, it can be linked to a carbon or a nitrogen atom of the heteroaryl group.

Suitably an aryl or heteroaryl group which forms a part of the $L^3$ linker is a heteroaryl group, typically a nitrogen-containing heteroaryl group for example pyrazole, imidazole, pyrrole, pyridine or pyrazine.

Examples of $L^3$ linkers include

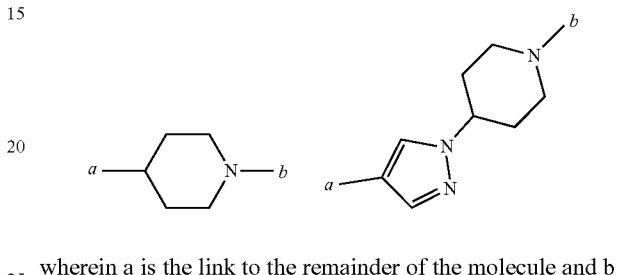

wherein a is the link to the remainder of the molecule and b is the link to $R^{13}$.

The group $R^{13}$ is H, —$OR^5$—$SO_2R^5$, —$C(O)OR^5$, —$C(O)NR^5R^6$ or —$C(=NR^7)NR^5R^6$; wherein $R^5$, $R^6$ and $R^7$ are as defined above;

In some suitable compounds $R^{13}$ is H.

In other compounds of this type, $R^{13}$ is —$OR^5$—$C(O)$ $OR^5$, —$C(O)NR^5R^6$ or —$C(=NR^7)NR^5R^6$, where suitably, each $R^5$, $R^6$ and $R^7$ group is independently selected from H and $C_{1-6}$ alkyl.

When $R^{13}$ is —$SO_2R^5$, it is preferred that $R^5$ is not H as these compounds may be unstable. Therefore, when $R^{13}$ is —$SO_2R^5$, suitably $R^5$ is $C_{1-6}$ alkyl.

Alternatively, $R^6$ (when present) may be H and $R^5$ may be a cyclic group, for example a 5- or 6-membered carbocyclic or heterocyclic group optionally substituted with an oxo, for example a lactone such as gamma-butyrolactone, tetrahydrofuran, pyrrolidine, piperidine or piperazine group.

Examples of $R^{13}$ groups of this type include —$OCH_3$, —$OCF_3$, —$C(O)OCH_3$, —$C(O)OH$, —$NH$—$C(O)O$—$C$ $(CH_3)_3$, —$C(=NH)NH_2$, —$SO_2$—$CH_3$, —$C(O)N(CH_3)_2$ and:

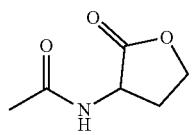

As mentioned above, $R^2$ is $C_{1-10}$ alkyl in which one or more —$CH_2$— groups is optionally replaced by —O— and which is optionally substituted as defined above.

Suitably, $R^2$ is —$(CH_2)_sCH_3$ or $(CH_2CH_2O)_t$—H, either of which is optionally substituted as defined above; and wherein s is 0-9, more suitably 0-6; and t is 1-3, especially 2 or 3.

More suitable substituents for $R^2$ include $OR^6$, halo, $NR^6R^7$, phenyl or pyridyl, where $R^6$ and $R^7$ are as defined above. Particularly suitable substituents for $R^2$ include OH, methoxy, ethoxy, halo, $NH_2$, phenyl or pyridyl, particularly OH, phenyl or pyridyl.

In some compounds of general formula (I), $R^2$ is —$(CH_2)_sCH_3$ and is optionally substituted with a single substituent as defined above.

In some such compounds of general formula (I) $R^2$ is methyl, ethyl, benzyl, pyridylmethyl, —$CH_2OH$, —$CH_2NH_2$, —$CH_2CH_2OH$ or $CH_2CH_2NH_2$.

In other particularly suitable compounds, $R^2$ is —$CH_2CH_2OCH_2CH_2OH$ or —$CH_2CH_2OCH_2CH_2OCH_2CH_2OH$ In some suitable compounds of general formula (I), $R^3$ is halo, cyano or methyl, ethyl, thiomethyl or thioethyl, any of which is optionally substituted with one or more halo substituents.

More suitably, $R^3$ is fluoro, chloro, bromo, cyano, methyl, trifluoromethyl or thiomethyl.

In particularly suitable compounds, $R^3$ is chloro, bromo, methyl or thiomethyl.

In the compounds of general formulae (I), $R^{10}$ is suitably H or $C_{1-6}$ alkyl optionally substituted with one or more substituents selected from halo, —$OR^6$ and —$NR^6R^7$, wherein $R^6$ and $R^7$ are as defined above.

More suitably, $R^{10}$ is H $C_{1-4}$ alkyl, or more suitably H, methyl or ethyl optionally substituted as defined above.

More suitably $R^{10}$ is optionally substituted with a single substituent selected from halo, —$OR^6$ and —$NR^6R^7$, wherein $R^6$ and $R^7$ are as defined above.

In particularly suitable compounds of general formula (I) $R^{10}$ is methyl, ethyl, —$CH_2OH$, —$CH_2NH_2$, —$CH_2CH_2OH$ or $CH_2CH_2NH_2$.

Some particularly suitable compounds of the present invention include those shown in Table 1 below, in which the numbers refer to the numbers of the Examples below.

TABLE 1

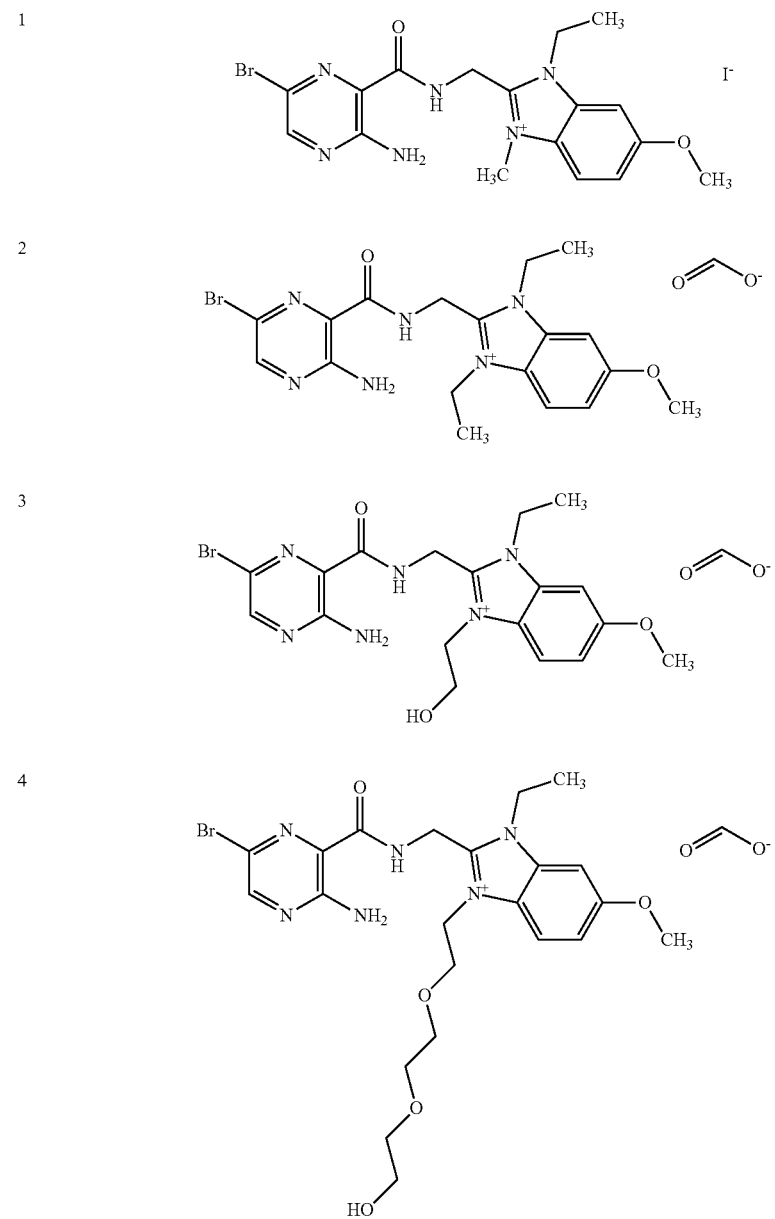

TABLE 1-continued
5 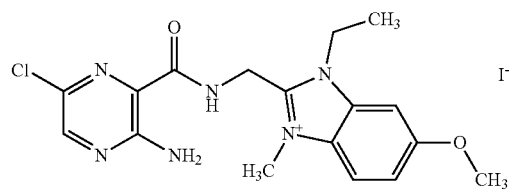 [SMILES: CCn1c(CNC(=O)c2nc(Cl)cnc2N)[n+](C)c2ccc(OC)cc21 ; [I-]]
6 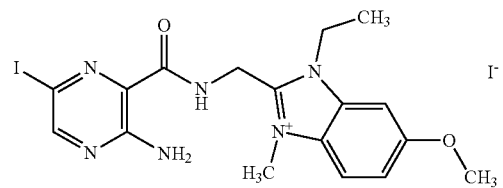 [SMILES: CCn1c(CNC(=O)c2nc(I)cnc2N)[n+](C)c2ccc(OC)cc21 ; [I-]]
7 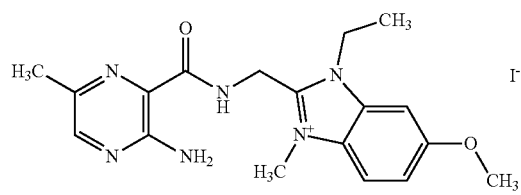
8 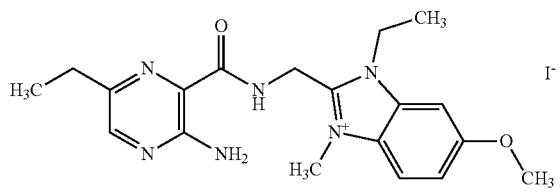 [SMILES: CCc1cnc(N)c(C(=O)NCc2n(CC)c3cc(OC)ccc3[n+]2C)n1 ; [I-]]
9 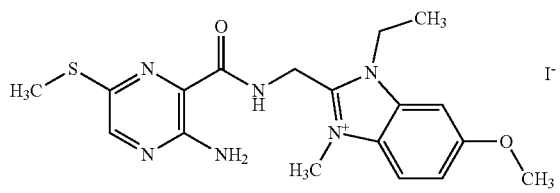
10 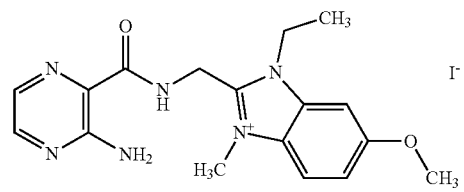 [SMILES: CCn1c(CNC(=O)c2nccnc2N)[n+](C)c2ccc(OC)cc21 ; [I-]]
11 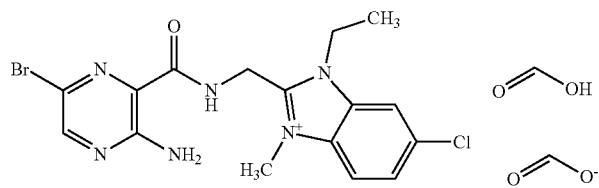
12 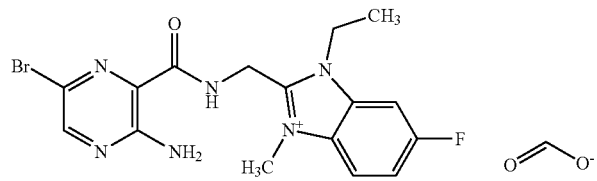

TABLE 1-continued
| 13 | 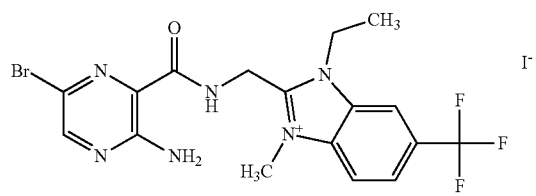 [SMILES: CCn1c(CNC(=O)c2nc(Br)cnc2N)[n+](C)c2ccc(C(F)(F)F)cc21 ; [I-]] |
| --- | --- |
| 14 | 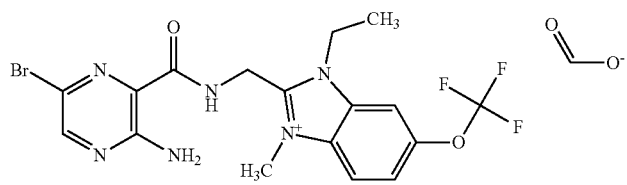  |
| 15 | 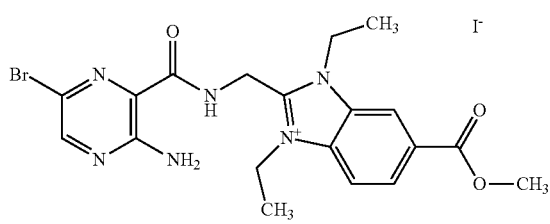 [SMILES: CCn1c(CNC(=O)c2nc(Br)cnc2N)[n+](CC)c2ccc(C(=O)OC)cc21 ; [I-]] |
| 16 | 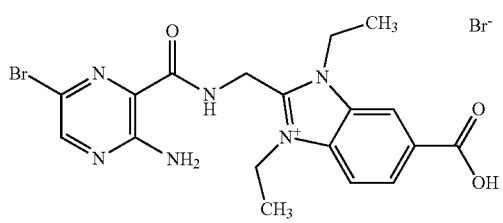 |
| 17 | 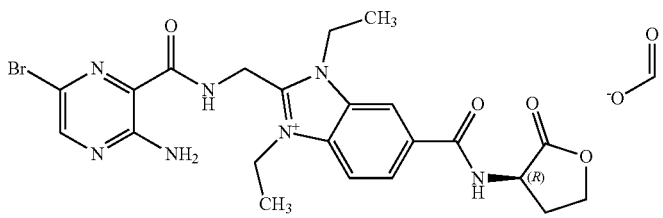 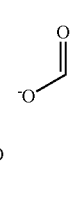 |
| 18 | 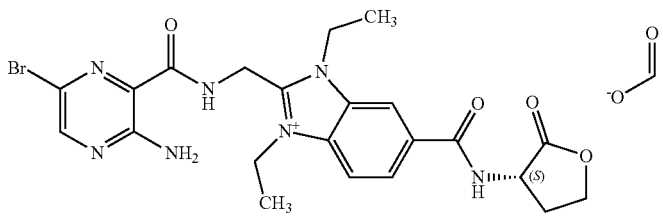 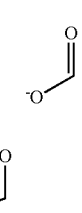 |
| 19 | 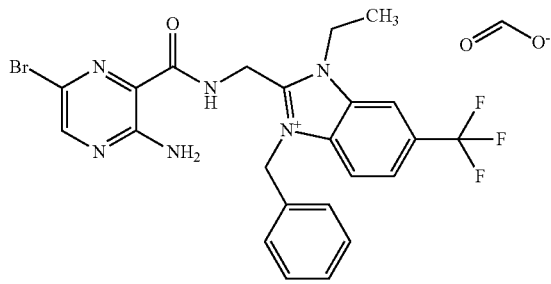 |

TABLE 1-continued
20
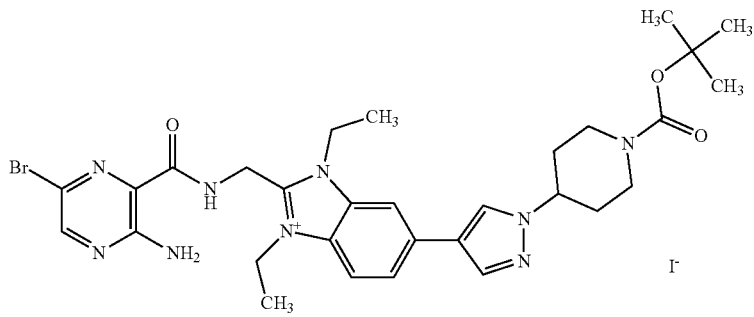 [SMILES: CCn1c(CNC(=O)c2nc(Br)cnc2N)[n+](CC)c2ccc(-c3cnn(C4CCN(C(=O)OC(C)(C)C)CC4)c3)cc21 ; [I-]]
21
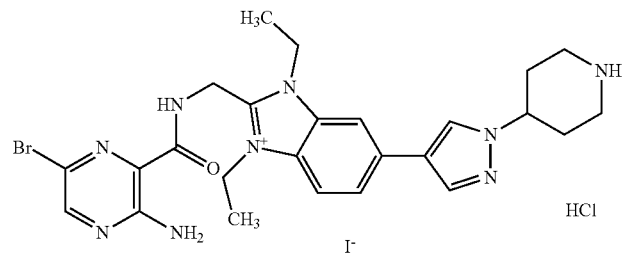 [SMILES: CCn1c(CNC(=O)c2nc(Br)cnc2N)[n+](CC)c2ccc(-c3cnn(C4CCNCC4)c3)cc21 ; Cl ; [I-]]
22
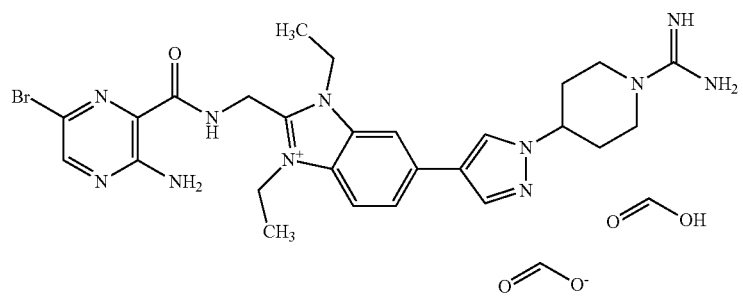
23
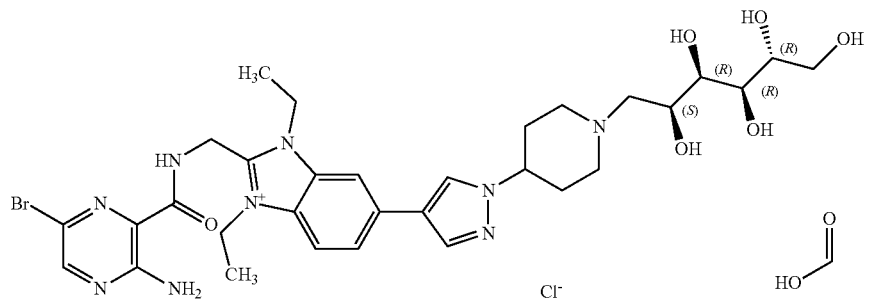
24
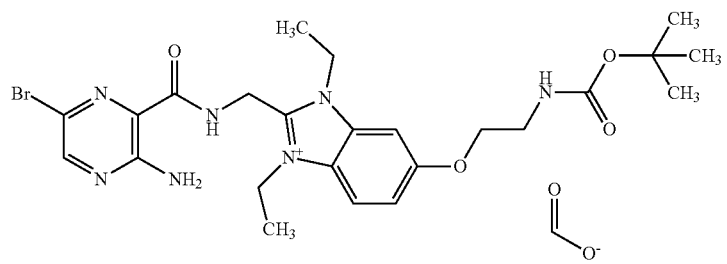

TABLE 1-continued

25
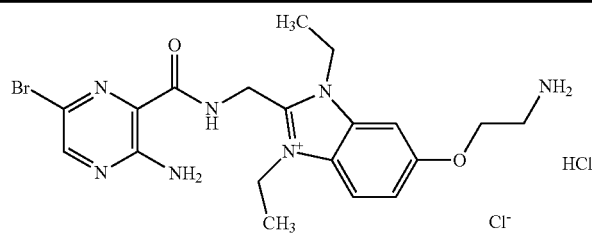

26
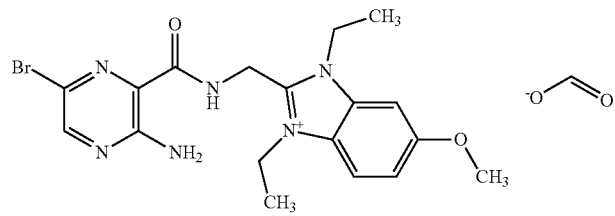

or alternative salts of the above compounds in which the anion is replaced by an alternative anion X⁻ as defined above.

Compounds of general formula (I) may be prepared by reacting a compound of general formula (II) or a salt thereof:

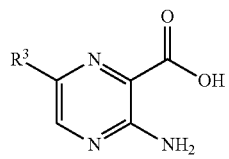

(II)

wherein $R^3$ is as defined for general formula (I); with a salt of general formula (III):

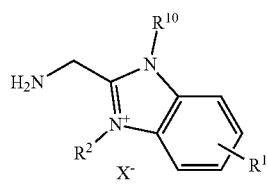

(III)

wherein $R^1$, $R^2$, $Q^1$, $Q^2$ and $X^-$ are as defined for general formula (I).

Suitably the reaction is carried out under basic conditions in the presence of a coupling reagent. The basic conditions may be supplied by a non-nucleophilic base such as N,N-diisopropylethylamine (DIPEA) or triethylamine. Suitable coupling reagents include O-(7-Azabenzotriazol-1-yl)-N,N,N',N'-tetramethyluronium hexafluorophosphate (HATU), O-(Benzotriazol-1-yl)-N,N,N',N'-tetramethyluronium tetrafluoroborate (TBTU), N,N,N'N'-tetramethyl-O-(1H-benzotriazol-1-yl)uronium hexafluorophosphate (HBTU) or a combination of 1-ethyl-3-(3-dimethylaminopropyl)carbodiimide (EDC) with 1-hydroxy-7-azabenzotriazole (HOAt) or hydroxybenzotriazole (HOBt).

The reaction may be conducted at a temperature of about 10 to 50° C., more usually at 15 to 30° C., or room temperature and in an organic solvent such as N,N-dimethylformamide.

Compounds of general formula (II) may be prepared by hydrolysis of a compound of general formula (V):

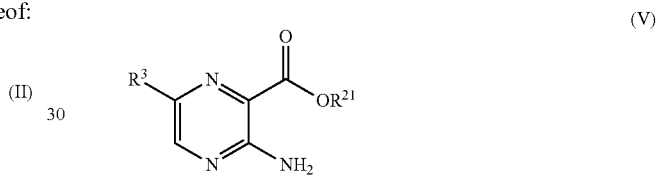

(V)

wherein $R^3$ is as defined for general formula (I) $R^{21}$ is $C_{1-6}$ alkyl or benzyl.

Suitably, the hydrolysis is base hydrolysis such that the compound of general formula (V) is reacted with a base, suitably a strong aqueous base such as lithium hydroxide, potassium hydroxide or sodium hydroxide.

Compounds of general formula (V) are known and are readily available. Alternatively a compound of general formula (V) may be prepared from another compound of general formula (V).

For example, a compound of general formula (V) in which $R^3$ is $C_{1-3}$ alkyl may be prepared from a compound of general formula (V) in which $R^3$ is halo, for example bromo, by reaction with a suitable alkyl borane derivative in the presence of a catalyst. Suitable alkyl borane derivatives include trimethyl boroxine when the required $R^3$ group is methyl, or ethylboronic acid or a propylboronic acid when the required $R^3$ group is ethyl or propyl.

Suitable catalysts include [1,1'-bis(diphenylphosphino) ferrocene] dichloropalladium(II). The reaction suitably takes place under an inert atmosphere, for example under nitrogen and at elevated temperature, for example from about 70 to 1100° C. and elevated pressure (e.g. in a pressure tube). Suitable solvents include ethers such as dimethylether.

Compounds of general formula (V) in which $R^3$ is —CN may be prepared from compounds of general formula (V) in which $R^3$ is halo, for example bromo, by reaction with a suitable cyanide salt. The reaction takes place in the presence of a copper (I) salt, for example copper (I) iodide and the cyanide salt is suitably copper(I) cyanide. The reaction may be catalysed with a palladium catalyst such as tetrakis (triphenylphosphine)palladium(0) and may take place at elevated pressure, for example in a pressure tube, and at a temperature of about 50 to 100° C., more usually 70 to 900° C., typically about 80° C.

In some cases, a compound of general formula (V) may be converted directly to a compound of general formula (II) with a different R³ group. For example, a compound of general formula (V) in which R³ is halo, for example bromo, may be converted to a compound of general formula (II) in which R³ is —S(C₁₋₃ alkyl) by reaction with a compound of general formula (VI):

wherein R²² is C₁₋₃ alkyl and Z⁺ is a suitable cation, for example Na⁺ or K⁺.

The reaction is suitably catalysed, for example with a palladium catalyst such as tetrakis(triphenylphosphine)palladium(0) and may take place at elevated pressure, for example in a pressure tube, and at a temperature of about 30 to 80° C., more usually 40 to 60° C., typically about 50° C.

Alternatively, a compound of general formula (I) may be prepared by reacting a salt of general formula (III) as defined above with a compound of general formula (IV):

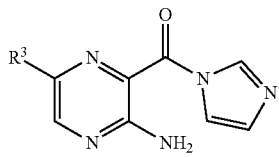

wherein R³ is as defined for general formula (I).

Suitably, the reaction is conducted at a temperature of about 10 to 50° C., more usually at 15 to 30° C., or room temperature and in an organic solvent such as N,N-dimethylformamide.

Compounds of general formula (IV) may be prepared by reacting a compound of general formula (V) as defined above with carbonyl diimidazole (CDI). Suitably the reaction takes place in an organic solvent such as N,N-dimethylformamide and at a temperature of from about 10 to 300° C., more usually 15 to 25° C. or room temperature.

Compounds of general formula (I) may also be synthesised from other compounds of general formula (I), for example using the methods described in Examples 7, 18, 21, 22 and 25 below.

Compounds of general formula (III) may be prepared from compounds of general formula (VII)

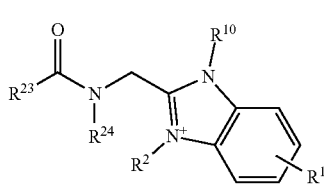

wherein R¹, R² and R¹⁰ are as defined for general formula (I);
R²³ is O(C₁₋₆) alkyl optionally substituted with aryl, or aryl, optionally substituted with C(O)OH; and R²⁴ is H; or
R²³ and R²⁴ together with the carbon and nitrogen atoms to which they are attached form a heterocyclic ring, optionally fused to an aryl or heteroaryl ring and optionally containing a further =O substituent.

When R²³ is O(C₁₋₆) alkyl optionally substituted with aryl, or aryl, optionally substituted with C(O)OH; and R²⁴ is H, the conversion to the compound of general formula (III) may be effected by reaction either with an acid, for example with hydrogen chloride solution, by an inorganic base such as sodium hydroxide or with an organic base such as piperidine or morpholine. The reaction is suitably carried out at about 10 to 30° C., more usually 15 to 25° C. or room temperature. The choice of acid or base will depend on the nature of the R²³ group.

Examples of individual R²³ groups include methoxy, ethoxy, ⁿpropyloxy, ⁱpropyloxy, ⁿbutyloxy, ˢbutyloxy, ᵗbutyloxy, benzyloxy and fluorenylmethoxy. When R²³ is alkoxy, the conversion to the compound of general formula (III) may be carried out under acidic conditions. For other R²³ groups, particularly fluorenylmethoxy, basic conditions are more appropriate.

An example of cyclic N(R²⁴)C(O)R²³ groups is 1,3-dioxo-2,3-dihydro-1H-isoindol-2-yl (phthalimidyl).

When R²³ and R²⁴ together with the carbon and nitrogen atoms to which they are attached form a heterocyclic ring of this type, the compound of general formula (III) may be synthesised by reacting the compound of general formula (VII) with hydrazine hydrate. Suitably, this reaction is carried out in an alcoholic solvent such as methanol and at elevated temperature, for example about 60-90° C., typically about 75° C.

Compounds of general formula (VII) may be prepared from compounds of general formula (VIII):

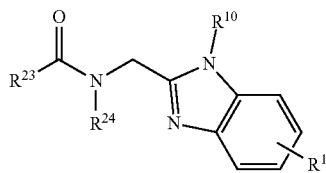

wherein R¹ and R¹⁰ are as defined for general formula (I) and R²³ and R²⁴ are as defined for general formula (VII);
by reaction with a compound of general formula (IX):

wherein R² is as defined for general formula (I) and X¹ is a leaving group such as halo; or with a compound of general formula (IXA):

wherein X¹ is as defined above for general formula (IX) and R²ᵃ is a protected R² group. For example, when the desired R² group contains one or more OH moieties, these may be protected using standard protecting groups, for example silyl protecting groups such as trimethylsilyl (TMS), ᵗbutyldimethylsilyl(TBDMS) etc.

When the route via the compound of general formula (IXA) is used, the compound of general formula (VIII) is suitably one in which R²³ is O(C₁₋₆) alkyl optionally substituted with aryl, or aryl, optionally substituted with C(O)OH; and R²⁴ is H; because, in this case, the silyl and carbonyloxy protecting groups can be removed using an acid such as hydrogen chloride solution.

In some cases, when a compound of general formula (IX) is reacted with a compound of general formula (VIII) in which N(R²⁴)C(O)R²³ is a cyclic group such as 1,3-dioxo-2,3-dihydro-1H-isoindol-2-yl, the reaction may be accompanied by ring opening. Thus a compound of general formula (VIII) in which $N(R^{24})C(O)R^{23}$ is 1,3-dioxo-2,3-dihydro-1H-isoindol-2-yl may give rise to a product of general formula (VII) in which $N(R^{24})C(O)R^{23}$ is:

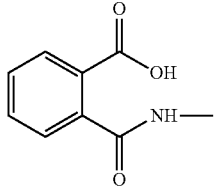

Some compounds of general formula (VIII) are known. For example, Intermediate 2 (see examples below) may be synthesised by the route set out in US 2015/0018314 A1.

Some compounds of general formula (VIII) may be synthesised from other compounds of general formula (VIII). For example, a compound of general formula (VIII) in which $R^1$ is $C(O)OR^5$, where $R^5$ is other than H may be converted to a compound of general formula (VIII) in which $R^1$ is $C(O)OH$ by hydrolysis, for example with a base, suitably an alkali metal hydroxide such as lithium hydroxide. The compound in which $R^1$ is $C(O)OH$ may then be converted to a compound in which $R^1$ is $C(O)OR^5$, where $R^5$ is other than H by reaction with a compound of general formula (X):

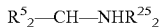 X wherein $R^5$ is as defined for general formula (I) except that it is not H and $R^{25}$ is $C_{1-4}$ alkyl.

Compounds of general formula (VIII) can also be converted to other compounds of general formula (VIII) with a different $R^{23}$ and/or $R^{24}$ groups. For example when $R^{23}$ is $O(C_{1-6})$ alkyl optionally substituted with aryl, or aryl, optionally substituted with $C(O)OH$; and $R^{24}$ is H, the compound of general formula (VIII) may be hydrolysed, for example by reaction with HCl in a solvent such as dioxane, to give a compound of general formula (XI):

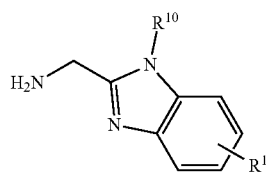

wherein $R^1$ and $R^{10}$ are as defined in general formula (I).

The compound of general formula (X) may be re-protected to obtain a new compound of general formula (VIII), for example by reaction with a compound of general formula (XII):

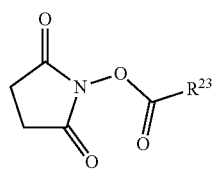

wherein $R^{23}$ is as defined above for general formula (VII). The reaction may be conducted in the presence of a base such as trimethylamine in a polar organic solvent, for example dichloromethane and at a temperature of from 10 to 30° C., more usually 15 to 25° C., typically at room temperature.

Compounds of general formula (VIII) in which $R^{23}$ is $O(C_{1-6})$ alkyl optionally substituted with aryl, or aryl, optionally substituted with $C(O)OH$; and $R^{24}$ is H may also be prepared from compounds of general formula (XIII):

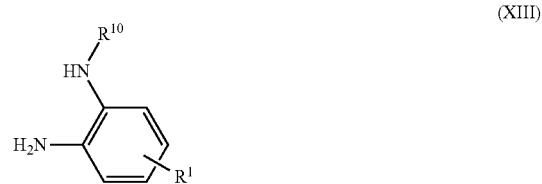

wherein $R^1$ and $R^{10}$ are as defined for general formula (I); by reaction with a compound of general formula (XIV):

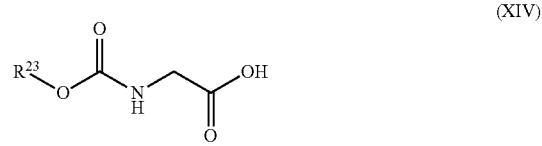

wherein $R^{23}$ is as defined above for general formula (VII).

The reaction suitably takes place in the presence of a base, typically a non-nucleophilic base, for example an amine such as N,N-diisopropylethylamine (DIPEA) or triethylamine and a peptide coupling agent, for example HATU, TBTU, HBTU or a combination EDC with HOAt or HOBt. The reaction is suitably conducted at a temperature of about 10 to 30° C., usually 15 to 25° C., for example at room temperature. Suitable reaction solvents include organic solvents such as N,N-dimethylformamide (DMF).

Compounds of general formulae (XIII) and (XIV) are known and are readily available or may be prepared by methods known to those of skill in the art.

Alternatively, Compounds of general formula (XIII) may be prepared from compounds of general formula (XV):

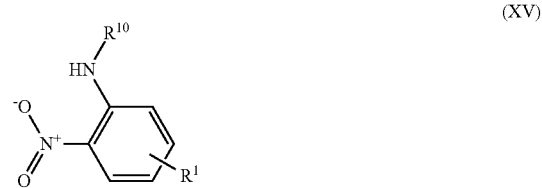

wherein $R^1$ and $R^{10}$ are as defined for general formula (I); by catalytic hydrogenation, suitably using a palladium catalyst.

The hydrogenation is suitably carried out at 1 atmosphere pressure and at a temperature of about 10 to 30° C., usually 15 to 25° C., for example at room temperature.

The product of general formula (XIII) can be reacted directly with a compound of general formula (XIV) as described above without further isolation or purification steps.

Compounds of general formula (XV) may be prepared from compounds of general formula (XVI):

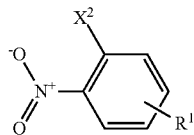

(XVI)

wherein $R^1$ is as defined for general formula (I) and $X^2$ is a leaving group, particularly a halo group such as chloro; by reaction with a compound of general formula (XVII):

wherein $R^{10}$ is as defined for general formula (I).

The reaction is suitably carried out under pressure, at a temperature of about 30-70° C., more usually about 40-60° C., typically about 50° C. and in an organic solvent such as tetrahydrofuran.

Compounds of general formulae (XVI) and (XVII) are known and are readily available or may be prepared by methods known to those of skill in the art.

The compounds of general formula (I) are ENaC blockers and are therefore useful in the treatment or prevention of respiratory diseases and conditions.

Therefore in a further aspect of the invention there is provided a compound of general formula (I) for use in medicine.

Suitably, the compound of general formula (I) is for use in the treatment or prophylaxis of a disease or condition mediated by ENaC.

There is also provided:
A compound of general formula (I) for use in the treatment or prophylaxis of respiratory diseases and conditions.
A compound of general formula (I) for use in the treatment or prophylaxis of skin conditions or ocular conditions.

The invention further provides:
The use of a compound of general formula (I) in the preparation of an agent for the treatment or prophylaxis of respiratory diseases and conditions.
The use of a compound of general formula (I) in the preparation of an agent for the treatment or prophylaxis of skin conditions or ocular conditions There is also provided:
A method for the treatment or prophylaxis of respiratory diseases and conditions, the method comprising administering to a patient in need of such treatment an effective amount of a compound of general formula (I).
A method for the treatment or prophylaxis of skin conditions and ocular conditions, the method comprising administering to a patient in need of such treatment an effective amount of a compound of general formula (I).

Respiratory diseases and conditions which may be treated by the compounds of general formula (I) include cystic fibrosis, chronic obstructive pulmonary disease (COPD), chronic bronchitis, emphysema, bronchiectasis, including non-cystic fibrosis bronchiectasis, and asthma.

Skin conditions which may be treated by the compounds of the present invention include psoriasis, atopic dermatitis and ichthyosis.

Ocular conditions which may be treated by the compounds of the present invention included dry eye disease (keratoconjunctivitus sicca).

The patient to be treated is suitably a mammal and more suitably a human.

The compounds of general formula (I) may be administered in a pharmaceutical composition and therefore in a further aspect of the invention there is provided a pharmaceutical composition comprising a compound of general formula (I) and a pharmaceutically acceptable excipient. Other pharmacologically active materials may also be present, as considered appropriate or advisable for the disease or condition being treated or prevented.

The carrier, or, if more than one be present, each of the carriers, must be acceptable in the sense of being compatible with the other ingredients of the formulation and not deleterious to the recipient.

The formulations include those suitable for oral, rectal, nasal, bronchial (inhaled), topical (including dermal, transdermal, eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, nasal, bronchial (inhaled) or topical administration.

Compositions for bronchial administration by inhalation are preferred as they particularly suitable for the treatment of respiratory conditions.

Topical formulations for administration as eye drops are also preferred and are particularly suitable for the treatment of dry eye disease.

Topical formulations for application to the skin are also preferred and are particularly suitable for the treatment of skin conditions such as psoriasis, atopic dermatitis and ichthyosis.

The composition may be prepared by bringing into association the above defined active agent with the excipient. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Compounds of general formula (I) may be used for the treatment of the respiratory tract by nasal, bronchial or buccal administration of, for example, aerosols or sprays which can disperse the pharmacological active ingredient in the form of a powder or in the form of drops of a solution or suspension. Pharmaceutical compositions with powder-dispersing properties usually contain, in addition to the active ingredient, a liquid propellant with a boiling point below room temperature and, if desired, adjuncts, such as liquid or solid non-ionic or anionic surfactants and/or diluents. Pharmaceutical compositions in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Parenteral formulations will generally be sterile.

Compounds of general formula (I) may be used in combination with one or more other active agents which are useful in the treatment or prophylaxis of respiratory diseases and conditions.

An additional active agent of this type may be included in the pharmaceutical composition described above but alternatively it may be administered separately, either at the same time as the compound of general formula (I) or at an earlier or later time.

Therefore in a further aspect of the present invention there is provided a product comprising a compound of general formula (I) and an additional agent useful in the treatment or prevention of respiratory conditions as a combined preparation for simultaneous, sequential or separate use in the treatment of a disease or condition mediated by ENaC and especially a respiratory disease or condition, for example one of the diseases and conditions mentioned above.

Suitable additional active agents which may be included in a pharmaceutical composition or a combined preparation with the compounds of general formula (I) include:
β2 adrenoreceptor agonists such as metaproterenol, isoproterenol, isoprenaline, albuterol, salbutamol, formoterol, salmeterol, indacaterol, terbutaline, orciprenaline, bitolterol mesylate and pirbuterol;
antihistamines, for example histamine $H_1$ receptor antagonists such as loratadine, cetirizine, desloratadine, levocetirizine, fexofenadine, astemizole, azelastine and chlorpheniramine or $H_4$ receptor antagonists;
dornase alpha;
corticosteroids such as prednisone, prednisolone, flunisolide, triamcinolone acetonide, beclomethasone dipropionate, budesonide, fluticasone propionate mometasone furoate and fluticasone furoate;
Leukotriene antagonists such as montelukast and zafirlukast;
Antibiotics.

EXAMPLES

A. Synthesis of Intermediates

All reactions involving moisture-sensitive reagents were carried out under a nitrogen atmosphere using standard vacuum line techniques and oven-dried glassware. Commercial anhydrous solvents were used in reactions and HPLC grade solvents were employed for work-up and chromatography. Water was purified using an Elix UV-5 system.

All other reagents were used as supplied without prior purification. Microwave experiments were carried out using a Biotage Initiator+. Flash column chromatography was carried out using a Biotage Isolera 4 using Biotage SNAP columns. NMR spectra were recorded on a Bruker Avance III HD 500 MHz or a Bruker Avance III HD 250 MHz using the solvent as internal deuterium lock. Spectra were recorded at room temperature unless otherwise stated. Analytical LCMS were carried out on the following systems: System A: stationary phase: Kinetex Core-Shell C18 2.1×50 mm, 5 μm, 40° C.; detection UV 215 nm-ELS-MS; mobile phase: A, water+0.1% formic acid; B, MeCN+0.1% formic acid; gradient (A:B ratio, time): 95:5-0:100, 1.20 min; 100:0, 0.10 min; 100:0-5:95, 0.01 min; System B: stationary phase: Phenomenex Gemini-NX C18 2.0×50 mm, 3 μm, 40° C.; detection UV 215 nm-ELS-MS; mobile phase: A, 2 mM $NH_4HCO_3$ pH 10; B, MeCN; gradient (A:B ratio, time): 99:1-0:100, 1.80 min; 100:0, 0.30 min; 100:0-1:99, 0.20 min; 1:99, 1.20 min; System C: stationary phase: Phenomenex Kinetix-XB C18 2.1×100 mm, 1.7 μm, 40° C.; detection UV 215 nm-ELS-MS; mobile phase: A, water+0.1% formic acid; B, MeCN+0.1% formic acid; gradient (A:B ratio, time): 95:5-0:100, 5.30 min; 100:0, 0.50 min; 100:0-5:95, 0.02 min; 5:95, 1.18 min. Preparative HPLC purification was carried out using the following conditions: stationary phase: Waters Sunfire 30×100 mm, 10 μm; detection UV 215 and 254 nm; mobile phase A: water+0.1% formic acid; B: MeCN+0.1% formic acid; gradient: 5-95% solvent B over 14 min; flowrate: 40 ml/min.

The following abbreviations and terms have the indicated meanings throughout:
AcOH glacial acetic acid
atm atmosphere
br broad
CDI 1,1'-carbonyldiimidazole
CV column volumes
dd doublet of doublets
DIPEA N,N-diisopropylethylamine
DMF N,N-dimethylformamide
DMSO dimethyl sulfoxide
dppf 1,1'-bis(diphenylphosphino)ferrocene
EDC.HCl N-(3-dimethylaminopropyl)-N'-ethylcarbodiimide hydrochloride
ELS evaporative light scattering
ESI electrospray ionisation EtOAc ethyl acetate
HATU 1-[bis(dimethylamino)methylene]-1H-1,2,3-triazolo[4,5-b]pyridinium 3-oxide hexafluorophosphate
HBTU 3-[bis(dimethylamino)methyliumyl]-3H-benzotriazol-1-oxide hexafluorophosphate
HOAt 1-hydroxy-7-azabenzotriazole
HPLC high-performance liquid chromatography
LC/MS liquid chromatography-mass spectrometry
m multiplet
MeCN acetonitrile
MeOH methanol
NMR nuclear magnetic resonance
q quartet
RT room temperature
$R_t$ retention time
s singlet
t triplet
TBTU O-(Benzotriazol-1-yl)-N,N,N',N'-tetramethyluronium tetrafluoroborate
TFA trifluoroacetic acid
THF tetrahydrofuran
XPhos-Pd-G2 chloro(2-dicyclohexylphosphino-2',4',6'-triisopropyl-1,1'-biphenyl)[2-(2'-amino-1,1'-biphenyl)]palladium(II)

Synthesis of lithium 3-amino-6-bromopyrazine-2-carboxylate: Intermediate 1

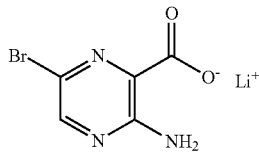

2 M aq. LiOH solution (65 ml, 130 mmol) was added over 5 min to a suspension of methyl 3-amino-6-bromopyrazine-2-carboxylate (15.0 g, 64.7 mmol) in MeOH (75 ml) at RT. The reaction was heated at 50° C. for 3 h. The reaction solution was concentrated in vacuo to remove most of the MeOH. The resulting aqueous suspension was filtered under vacuum, then the resulting brown solid was washed with the minimum of water, followed by the minimum of MeCN, and then dried until constant weight under vacuum at 40° C. to afford the product as a brown solid (10.3 g). The filtrate was evaporated to dryness and then suspended in the minimum of water (~30 ml). The precipitated solid was filtered under vacuum, then washed with the minimum of water and MeCN and then the resulting brown solid was dried until constant weight under vacuum to afford an additional batch of product as a brown solid (2.00 g). The two batches were combined as a MeCN suspension then evaporated and dried under vacuum to afford the product as a brown solid (12.3 g, 85%).

$^1$H NMR (500 MHz, DMSO-d$_6$) δ 9.12-6.65 (m, 3H).

LC/MS (System A): m/z (ESI$^+$)=218 [M($^{79}$Br)H$^+$], 220 [M($^{81}$Br)H$^+$]), $R_t$=0.69 min, UV purity=100%.

Synthesis of 5-bromo-3-(1H-imidazole-1-carbonyl)pyrazin-2-amine: Intermediate 2

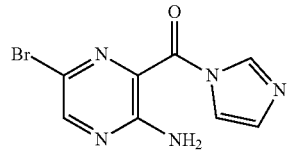 [SMILES: Nc1ncc(Br)nc1C(=O)n1ccnc1]

CDI (2.23 g, 13.8 mmol) was added to a suspension of commercial 3-amino-6-bromopyrazine-2-carboxylic acid (2.00 g, 9.17 mmol) in DMF (20 ml). The reaction was stirred at RT for 16 h. The reaction mixture was cooled (0° C.) then diluted with water (20 ml). The solid was collected by filtration then washed with the minimum volume of water and cooled (0° C.) MeCN then dried under vacuum to afford the product as a yellow solid (2.23 g, 86%).

$^1$H NMR (250 MHz, DMSO-d$_6$) δ 8.55 (s, 2H), 7.96-7.82 (m, 3H), 7.15-7.07 (dm, 1H).

LC/MS (System A, MeOH quench): m/z (ESI$^+$)=232 [Methyl ester M($^{79}$Br)H$^+$], 234 [Methyl ester M($^{81}$Br)H$^+$]), $R_t$=0.87 min, UV purity=95%.

Synthesis of lithium 3-amino-6-iodopyrazine-2-carboxylate: Intermediate 3

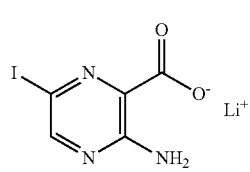

Aqueous LiOH solution (2.0 M, 0.72 ml, 1.4 mmol) was added dropwise to a suspension of methyl 3-amino-6-iodopyrazine-2-carboxylate (200 mg, 0.72 mmol) in MeOH (3.5 ml) at RT. The reaction was heated at 50° C. for 1.5 h then allowed to cool to RT. The reaction mixture was concentrated in vacuo to remove most of the MeOH. The resulting suspension was filtered and the solid thus obtained was washed with the minimum volume of water (0.5 ml) and dried under vacuum to afford the product as a brown solid (40 mg, 20%).

$^1$H NMR (250 MHz, DMSO-d$_6$) δ 8.09 (s, 1H), 7.73 (s, 2H).

LC/MS (System A): m/z (ESI$^+$)=265 [MH$^+$], $R_t$=0.78 min, UV purity=97%

Synthesis of methyl 3-amino-6-methylpyrazine-2-carboxylate: Intermediate 4

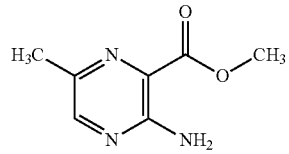

K₂CO₃ (0.89 g, 6.46 mmol) was added to a solution of methyl 3-amino-6-bromopyrazine-2-carboxylate (0.75 g, 3.23 mmol) in anhydrous DME (15 ml) in a pressure tube. Trimethylboroxine (0.99 ml, 3.56 mmol) was added then the resulting brown suspension was de-gassed by bubbling a stream of nitrogen through the reaction mixture for 5 min. Pd(dppf)₂Cl₂ (0.13 g, 0.16 mmol) was added then the pressure tube was flushed with nitrogen and sealed. The reaction was stirred at 100° C. for 16 h then allowed to cool to RT. The resulting suspension was filtered then the solid thus obtained was washed with EtOAc (20 ml). The combined filtrate was concentrated in vacuo. The crude material was purified by flash column chromatography on a silica column (50 g). The column was eluted with EtOAc:heptane, increasing the gradient linearly from 0:100 to 50:50 over 10 column volumes. The desired fractions were combined and evaporated to yield the product as a light yellow solid (470 mg, 87%).

¹H NMR (250 MHz, DMSO-d₆) δ 8.18 (s, 1H), 7.11 (s, 2H), 3.83 (s, 3H), 2.33 (s, 3H).

LC/MS (System A): m/z (ESI⁺)=168 [MH⁺], $R_t$=0.68 min, UV purity=100%.

(1.00 g, 4.31 mmol), ethylboronic acid (0.637 g, 8.62 mmol) and K₂CO₃ (1.79 g, 12.9 mmol) in DME (20 ml). The resultant suspension was de-gassed by bubbling a stream of nitrogen through the reaction mixture for 1 min. The reaction mixture was heated at 90° C. for 17 h then allowed to cool to RT. The reaction was recharged with ethylboronic acid (318 mg, 4.31 mmol) and Pd(dppf)Cl₂ (79 mg, 0.11 mmol) then heated at 90° C. for 2 h. The reaction mixture was allowed to cool to RT then added to saturated aq. NaHCO₃ solution (40 ml). The resultant mixture was extracted with EtOAc (2×40 ml) then the combined organic extracts were washed with brine (40 ml), dried over MgSO₄, filtered and concentrated in vacuo. The crude material was purified by flash column chromatography on a silica column (50 g). The column was eluted with EtOAc:heptane, increasing the gradient linearly from 6:94 to 50:50 over 10 column volumes. The desired fractions were combined and evaporated to yield the product as a yellow solid (322 mg, 41%).

¹H NMR (250 MHz, CDCl₃) δ 8.14 (s, 1H), 6.27 (s, 2H), 3.98 (s, 3H), 2.79 (q, J=7.6 Hz, 2H), 1.29 (t, J=7.6 Hz, 3H).

LC/MS (System A): m/z (ESI⁺)=182 [MH⁺], $R_t$=0.81 min, UV purity=100%.

Synthesis of lithium 3-amino-6-methylpyrazine-2-carboxylate: Intermediate 5

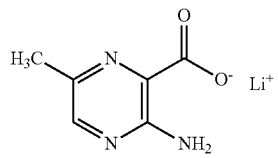

Synthesis of lithium 3-amino-6-ethylpyrazine-2-carboxylate: Intermediate 7

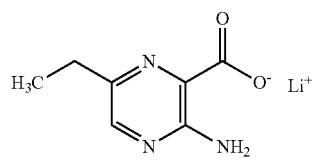

Aqueous LiOH solution (2.0 M, 4.3 ml, 8.6 mmol) was added dropwise to a suspension of methyl 3-amino-6-methylpyrazine-2-carboxylate, Intermediate 4 (464 mg, 2.78 mmol) in MeOH (5 ml) at RT. The reaction was heated at 50° C. for 1 h then allowed to cool to RT.

The reaction mixture was concentrated in vacuo to remove most of the MeOH. The resulting suspension was filtered and the solid thus obtained was washed with the minimum volume of water (1 ml) and dried under vacuum to afford the product as a yellow solid (395 mg, 89%).

¹H NMR (250 MHz, DMSO-d₆) δ 7.91 (s, 1H), 7.48 (s, 2H), 2.21 (s, 3H).

LC/MS (System A): m/z (ESI⁺)=154 [MH⁺], $R_t$=0.33 min.

Synthesis of methyl 3-amino-6-ethylpyrazine-2-carboxylate: Intermediate 6

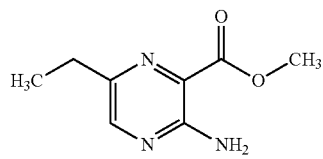

Pd(dppf)Cl₂ (158 mg, 0.215 mmol) was added to a suspension of methyl 3-amino-6-bromopyrazine-2-carboxylate Aqueous LiOH solution (2.0 M, 1.8 ml, 3.6 mmol) was added dropwise to a suspension of methyl 3-amino-6-ethylpyrazine-2-carboxylate, Intermediate 6 (322 mg, 1.78 mmol) in MeOH (5 ml) at RT. The reaction was heated at 50° C. for 2 h then allowed to cool to RT. The reaction mixture was concentrated in vacuo to remove most of the MeOH. The resulting suspension was filtered and the solid thus obtained was washed with the minimum volume of water (0.5 ml) and dried under vacuum to afford the product as a yellow solid (306 mg, 99%).

¹H NMR (250 MHz, DMSO-d₆) δ 7.94 (s, 1H), 7.50 (s, 2H), 2.59-2.51 (m, 2H), 1.11 (t, J=7.6 Hz, 3H).

LC/MS (System A): m/z (ESI⁺)=168 [MH⁺], $R_t$=0.68 min, UV purity=100%.

Synthesis of 3-amino-6-(methylsulfanyl)pyrazine-2-carboxylic acid: Intermediate 8

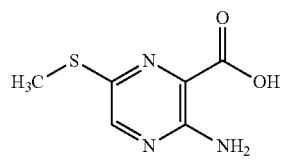

A solution of methyl 3-amino-6-bromopyrazine-2-carboxylate (500 mg, 2.16 mmol), tetrakis(triphenylphosphine)

palladium(0) (124 mg, 0.108 mmol) and sodium methanethiolate (306 mg, 4.31 mmol) in DMF (10 ml) was sealed in a nitrogen flushed pressure tube. The pressure tube was heated at 50° C. for 2 h then allowed to cool to RT. The reaction mixture was diluted with EtOAc (30 ml) then washed with hydrochloric acid (1 M, 2×25 ml). A precipitate formed, which was removed by filtration. The filtrate was dried over MgSO$_4$ and evaporated. The crude material thus obtained was purified by flash column chromatography on C18 (60 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and evaporated to yield the product as a dark yellow solid (77 mg, 19%).

$^1$H NMR (250 MHz, DMSO-d$_6$) δ 12.89 (s, 1H), 8.24 (s, 1H), 7.25 (s, 2H), 3.30 (s, 3H).

LC/MS (System A): m/z (ESI$^+$)=186 [MH$^+$], R$_t$=0.72 min, UV purity=98%.

Synthesis of methyl 3-amino-6-cyanopyrazine-2-carboxylate: Intermediate 9

Tetrakis(triphenylphosphine)palladium(0) (176 mg, 0.152 mmol) was added to a solution of methyl 3-amino-6-iodopyrazine-2-carboxylate (350 mg, 1.25 mmol) and CuI (167 mg, 0.878 mmol) in DMF (8 ml) in a pressure tube. The reaction tube was flushed with nitrogen then CuCN (225 mg, 2.51 mmol) was added. The tube was sealed then heated at 80° C. for 4 h. The reaction mixture was allowed to cool to RT, then added onto saturated aq. NaHCO$_3$ solution (25 ml) and extracted with EtOAc (3×25 ml). The combined organic extracts were washed with brine (25 ml) then dried over MgSO$_4$, filtered, then concentrated in vacuo to a pale yellow oil. The crude material was transferred onto a C18 Samplet®, dried under vacuum, and then purified by flash column chromatography on silica (25 g). The column was eluted with EtOAc:heptane, increasing the gradient linearly from 12:88 to 100:0 over 10 column volumes. The desired fractions were combined and evaporated to afford the product as a white solid (23 mg, 10%).

$^1$H NMR (250 MHz, CDCl$_3$) δ 8.48 (s, 1H), 8.11 (s, 1H), 5.85 (s, 1H), 4.02 (s, 3H).

LC/MS (System A): m/z (ESI$^+$)=179 [MH$^+$], R$_t$=0.75 min, UV purity=100%.

Synthesis of 3-amino-6-cyanopyrazine-2-carboxylic acid: Intermediate 10

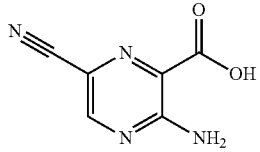

Aq. LiOH solution (2.0 M, 0.13 ml, 0.16 mmol) was added to a solution of methyl 3-amino-6-cyanopyrazine-2-carboxylate, Intermediate 9 (25 mg, 0.14 mmol) in THF (1 ml). The reaction mixture was stirred at RT for 1 h then added onto aq. HCl solution (2 M, 5 ml).

The resulting mixture was extracted with EtOAc (2×10 ml) then the combined organic phases were dried over MgSO$_4$ and concentrated in vacuo to afford the product as a pale yellow solid (21 mg, 91%).

$^1$H NMR (250 MHz, DMSO-d$_6$) δ 8.68 (s, 1H), 8.42 (s, 1H), 8.09 (s, 1H).

LC/MS (System A): m/z (ESI$^-$)=163 [(M−H)$^-$], R$_t$=0.29 min.

Synthesis of 2-[(1-ethyl-6-methoxy-1H-1,3-benzodiazol-2-yl)methyl]-2,3-dihydro-1H-isoindole-1,3-dione: Intermediate 11

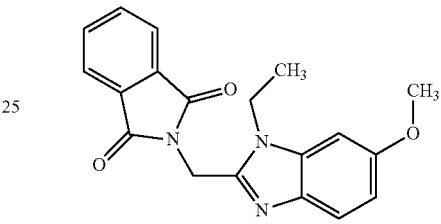

Intermediate 11 was synthesised according to literature procedures (US 2015/0018314 A1).

Synthesis of 2-[(1,3-dioxo-2,3-dihydro-1H-isoindol-2-yl)methyl]-1-ethyl-6-methoxy-3-methyl-1H-1,3-benzodiazol-3-ium iodide: Intermediate 12

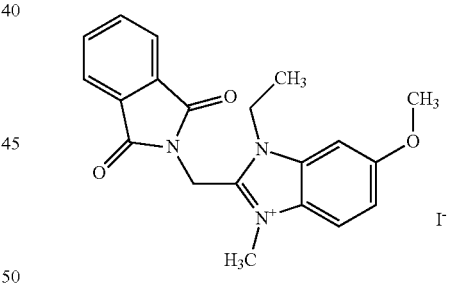

Iodomethane (590 μl, 9.47 mmol) was added to a suspension of 2-[(1-ethyl-6-methoxy-1H-1,3-benzodiazol-2-yl)methyl]-2,3-dihydro-1H-isoindole-1,3-dione, Intermediate 11 (1.59 g, 4.74 mmol) in MeCN (13 ml) in a pressure tube. The mixture was heated at 80° C. for 4 h then allowed to cool to RT. The resulting suspension was reduced to approximately half of the original volume under a stream of nitrogen. The solid was collected by filtration then washed with further MeCN (3 ml) to yield the product as a white solid (1.99 g, 87%).

$^1$H NMR (500 MHz, DMSO-d$_6$) δ 8.01-7.84 (m, 5H), 7.62 (d, J=2.2 Hz, 1H), 7.32 (dd, J=9.2, 2.3 Hz, 1H), 5.37 (s, 2H), 4.71 (q, J=7.1 Hz, 2H), 4.11 (s, 3H), 3.92 (s, 3H), 1.42 (t, J=7.2 Hz, 3H).

LC/MS (System A): m/z (ESI$^+$)=350 [M$^+$], R$_t$=0.87 min, UV purity=99%.

Synthesis of 2-(aminomethyl)-1-ethyl-6-methoxy-3-methyl-1H-1,3-benzodiazol-3-ium iodide: Intermediate 13

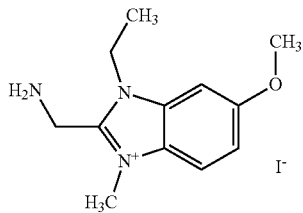 [SMILES: CCn1c(CN)[n+](C)c2ccc(OC)cc21 ; [I-]]

Hydrazine hydrate (1.17 ml, 24.0 mmol) was added to a suspension of 2-[(1,3-dioxo-2,3-dihydro-1H-isoindol-2-yl)methyl]-1-ethyl-6-methoxy-3-methyl-1H-1,3-benzodiazol-3-ium iodide, Intermediate 12 (2.29 g, 4.80 mmol) in MeOH (25 ml). The mixture was heated at 75° C. for 1 h. The reaction was concentrated to dryness and the resulting solid was suspended in $CH_2Cl_2$:MeOH (10:1). The solid was collected by filtration and washed with $CH_2Cl_2$. The filtrate was concentrated to dryness to afford the product as a pale brown solid (1.60 g, 96%).

$^1$H NMR (500 MHz, DMSO-$d_6$) δ 7.91 (d, J=9.1 Hz, 1H), 7.57 (d, J=2.3 Hz, 1H), 7.26 (dd, J=9.1, 2.3 Hz, 1H), 4.58 (q, J=7.2 Hz, 2H), 4.23 (s, 2H), 4.03 (s, 3H), 3.91 (s, 3H), 1.42 (t, J=7.2 Hz, 3H).

LC/MS (System A): m/z (ESI$^+$)=220 [M$^+$], $R_t$=0.14 min, ELS purity=100%.

Synthesis of 2-[(1,3-dioxo-2,3-dihydro-1H-isoindol-2-yl)methyl]-1,3-diethyl-6-methoxy-1H-1,3-benzodiazol-3-ium iodide: Intermediate 14

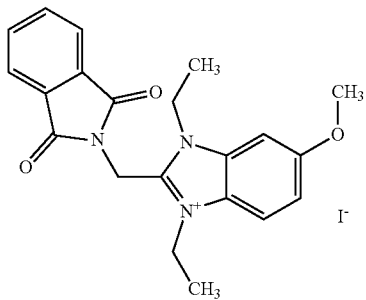 [SMILES: CCn1c(CN2C(=O)c3ccccc3C2=O)[n+](CC)c2ccc(OC)cc21 ; [I-]]

Iodoethane (715 μl, 8.95 mmol) was added to a suspension of 2-[(1-ethyl-6-methoxy-1H-1,3-benzodiazol-2-yl)methyl]-2,3-dihydro-1H-isoindole-1,3-dione, Intermediate 11 (3.00 g, 8.95 mmol) in MeCN (20 ml). The mixture was heated at 80° C. for 4 h. Iodoethane (715 μl, 8.95 mmol) was added and mixture was stirred at 80° C. for 16 h. Iodoethane (715 μl, 8.95 mmol) was added and mixture was stirred at 80° C. for a further 24 h the allowed to cool to RT. The mixture was concentrated in vacuo to approximately one third of the original volume. The precipitate was collected by filtration then washed with MeCN to afford a grey solid (2.6 g). The filtrate was concentrated to afford a dark grey solid. The two batches of solid thus obtained were combined and suspended in MeCN (20 ml). Iodoethane (715 μl, 8.95 mmol) was added then the reaction mixture was stirred at 80° C. for 18 h then at 100° C. for 4 h. The reaction mixture was split into two equal portions in pressure tubes. Iodoethane (300 μl, 3.75 mmol) was added to both reaction mixtures then the pressure tubes were sealed and left to heat at 100° C. for 16 h. The reaction mixtures were allowed to cool to RT then combined. The resultant mixture was concentrated in vacuo to ~5 ml then filtered. The collected solid was washed with the minimum of MeCN (0.5 ml) to yield the product as a grey solid (2.37 g). The filtrate was concentrated under reduced pressure to afford a dark brown solid, which was triturated with EtOAc (~10 ml) and filtered. The filtrate was left to stand overnight then it was filtered again. The solids obtained from the EtOAc filtrations were combined and dried to yield an additional batch of the product as a grey solid (1.24 g). The two batches of product obtained were combined as an EtOAc suspension then evaporated and dried under vacuum to afford the product as a grey solid (3.61 g, 81%).

$^1$H NMR (250 MHz, DMSO-$d_6$) δ 8.02 (d, J=9.2 Hz, 1H), 7.98-7.86 (m, 4H), 7.63 (d, J=2.2 Hz, 1H), 7.31 (dd, J=9.1, 2.3 Hz, 1H), 5.40 (s, 2H), 4.67 (m, 4H), 3.92 (s, 3H), 1.49-1.33 (m, 6H).

LC/MS (System A): m/z (ESI$^+$)=365 [M$^+$], $R_t$=0.93 min, UV purity=99%.

Synthesis of 2-(aminomethyl)-1,3-diethyl-6-methoxy-1H-1,3-benzodiazol-3-ium iodide: Intermediate 15

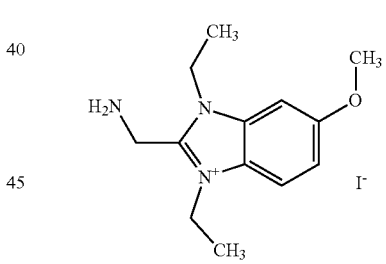

Hydrazine hydrate (1.18 ml, 24.1 mmol) was added to a suspension of 2-[(1,3-dioxo-2,3-dihydro-1H-isoindol-2-yl)methyl]-1,3-diethyl-6-methoxy-1H-1,3-benzodiazol-3-ium iodide, Intermediate 14 (2.37 g, 4.82 mmol) in MeOH (25 ml). The mixture was then heated at 75° C. for 2.5 h then left to cool to RT over 16 h. The reaction mixture was concentrated to dryness and the resulting solid was suspended in $CH_2Cl_2$:MeOH (10:1) then filtered. The collected solid was washed with $CH_2Cl_2$. The filtrate was concentrated to dryness to afford the product as a grey solid (1.89 g, >99%).

$^1$H NMR (250 MHz, DMSO-$d_6$) δ 7.95 (d, J=9.1 Hz, 1H), 7.58 (d, J=2.3 Hz, 1H), 7.25 (dd, J=9.1, 2.3 Hz, 1H), 4.57 (m, 4H), 4.25 (s, 2H), 3.91 (s, 3H), 1.43 (m, 6H).

LC/MS (System A): m/z (ESI$^+$)=234 [M$^+$], $R_t$=0.16 min, ELS purity=92%.

Synthesis of tert-butyl N-[(1-ethyl-6-methoxy-1H-1,3-benzodiazol-2-yl)methyl]carbamate: Intermediate 16

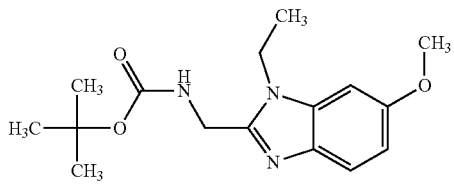 [SMILES: CCn1c(CNC(=O)OC(C)(C)C)nc2ccc(OC)cc21]

HATU (8.53 g, 22.3 mmol) and DIPEA (7.1 ml, 41 mmol) were added to a solution of N-(tert-butoxycarbonyl)glycine (3.93 g, 22.4 mmol) in DMF (40 ml). The resulting solution was stirred at RT for 0.5 h then a solution of 1-N-ethyl-5-methoxybenzene-1,2-diamine (3.39 g, 20.4 mmol) in THF (20 ml) was added. The reaction was left to stir at RT for 80 min then the reaction mixture was diluted with EtOAc (200 ml) and water (150 ml). The phases were separated then the organic phase was washed with water (3×150 ml) and brine (150 ml). The combined organic phases were dried over $Na_2SO_4$ then concentrated in vacuo to afford the crude intermediate as a dark red viscous oil. The intermediate was taken up in AcOH (40 ml) and the resulting solution was stirred at 60° C. for 18 h. The reaction mixture was allowed to cool then concentrated in vacuo. The residue was then dissolved in EtOAc (200 ml) then the pH was adjusted to 9 by the addition of saturated aq. $NaHCO_3$ solution. The phases were separated and the organic phase was washed with water (2×150 ml) and brine (150 ml), then dried over $Na_2SO_4$ and concentrated in vacuo to afford the crude product as a dark red oil. The crude material was purified by flash column chromatography on a silica column (340 g). The column was eluted with $CH_2Cl_2$:MeOH, increasing the gradient linearly from 100:0 to 92:8 over 10 column volumes. The desired fractions were combined and evaporated to a viscous dark red oil which solidified on standing to yield the product as a dark red solid (5.02 g, 77%).

$^1$H NMR (500 MHz, DMSO-$d_6$) δ 7.47-7.39 (m, 2H), 7.06 (d, J=2.4 Hz, 1H), 6.78 (dd, J=8.7, 2.4 Hz, 1H), 4.39 (d, J=5.9 Hz, 2H), 4.22 (q, J=7.1 Hz, 2H), 3.81 (s, 3H), 1.39 (s, 9H), 1.28 (t, J=7.2 Hz, 3H). NMR purity=85%

LC/MS (System A): m/z (ESI$^+$)=306 [MH$^+$], R$_t$=0.88 min, UV purity=96%.

Synthesis of 2-({[(tert-butoxy)carbonyl]amino}methyl)-1-ethyl-3-(2-hydroxyethyl)-6-methoxy-1H-1,3-benzodiazol-3-ium bromide: Intermediate 17

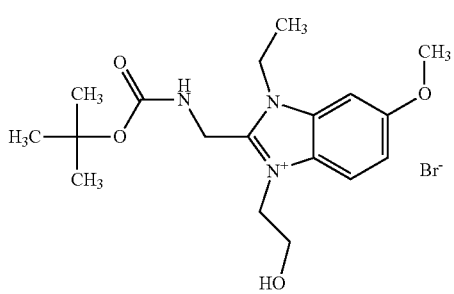 [SMILES: CCn1c(CNC(=O)OC(C)(C)C)[n+](CCO)c2ccc(OC)cc21 ; [Br-]]

(2-Bromoethoxy)(tert-butyl)dimethylsilane (1.66 g, 6.96 mmol) was added to a suspension of tert-butyl N-[(1-ethyl-6-methoxy-1H-1,3-benzodiazol-2-yl)methyl]carbamate, Intermediate 16 (85%, 500 mg, 1.39 mmol) in MeCN (5 ml) in a pressure tube. The tube was sealed then the reaction mixture was stirred at 80° C. for 0.5 h then at 100° C. for 16 h. The reaction was allowed to cool to RT then additional (2-bromoethoxy)(tert-butyl)dimethylsilane (1.00 g, 4.18 mmol) was added. The tube was sealed then the reaction was left to stir at 100° C. for a further 24 h. The reaction mixture was allowed to cool then concentrated in vacuo to a red oil. The crude material was purified by flash column chromatography on a silica column (25 g). The column was eluted with $CH_2Cl_2$:MeOH, increasing the gradient linearly from 100:0 to 90:10 over 10 column volumes. The desired fractions were combined and evaporated to yield a viscous dark red oil (615 mg). The material was further purified by flash column chromatography on C18 (30 g). The column was eluted with MeCN:$H_2O$+0.1% formic acid using the following gradient (% MeCN, column volumes): 10%, 2 CV; 10-36%; 36%, 2 CV; 36-50%, 4 CV; 50-100%, 3 CV; 100%, 3 CV. The desired fractions were combined and evaporated to yield the product as a viscous dark red oil (278 mg, 43%).

$^1$H NMR (500 MHz, DMSO-$d_6$) δ 8.28 (s, 1H), 7.99-7.84 (m, 2H), 7.57 (d, J=2.2 Hz, 1H), 7.28 (dd, J=9.1, 2.3 Hz, 1H), 4.76 (d, J=5.5 Hz, 2H), 4.71-4.65 (m, 2H), 4.59 (q, J=7.1 Hz, 2H), 3.92 (s, 3H), 3.77 (t, J=4.7 Hz, 2H), 3.17 (s, 2H), 1.41 (t, J=7.2 Hz, 3H), 1.38 (d, J=2.8 Hz, 9H).

LC/MS (System A): m/z (ESI$^+$)=350 [M$^+$], R$_t$=0.88 min, UV purity=92%.

Synthesis of 2-(aminomethyl)-1-ethyl-3-(2-hydroxyethyl)-6-methoxy-1H-1,3-benzodiazol-3-ium hydrochloride chloride: Intermediate 18

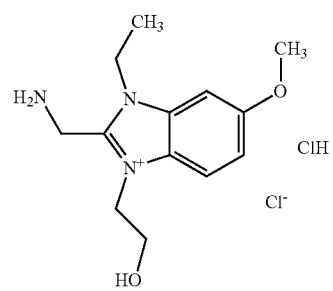 [SMILES: CCn1c(CN)[n+](CCO)c2ccc(OC)cc21 ; [Cl-] ; Cl]

Hydrogen chloride solution in dioxane (4.0 M, 1.2 ml, 4.8 mmol) was added to a solution of 2-({[(tert-butoxy)carbonyl]amino}methyl)-1-ethyl-3-(2-hydroxyethyl)-6-methoxy-1H-1,3-benzodiazol-3-ium bromide, Intermediate 17 (90%, 227 mg, 0.47 mmol) in MeCN (3 ml). The resulting mixture was stirred at RT for 1 h. The reaction mixture was concentrated in vacuo to afford the product as a dark purple solid (153 mg, 99%).

$^1$H NMR (500 MHz, DMSO-$d_6$) δ 8.89 (s, 3H), 8.03 (d, J=9.2 Hz, 1H), 7.66 (d, J=2.3 Hz, 1H), 7.35 (dd, J=9.2, 2.3 Hz, 1H), 4.82-4.73 (m, 4H), 4.69 (q, J=7.2 Hz, 2H), 3.94 (s, 3H), 3.80 (t, J=4.6 Hz, 2H), 1.45 (t, J=7.2 Hz, 3H).

LC/MS (System B): m/z (ESI$^+$)=250 [M$^+$], R$_t$=1.58 min, UV purity=99%.

Synthesis of 2-{[(2-carboxyphenyl)formamido]methyl}-1-ethyl-3-{2-[2-(2-hydroxyethoxy)ethoxy]ethyl}-6-methoxy-1H-1,3-benzodiazol-3-ium iodide: Intermediate 19

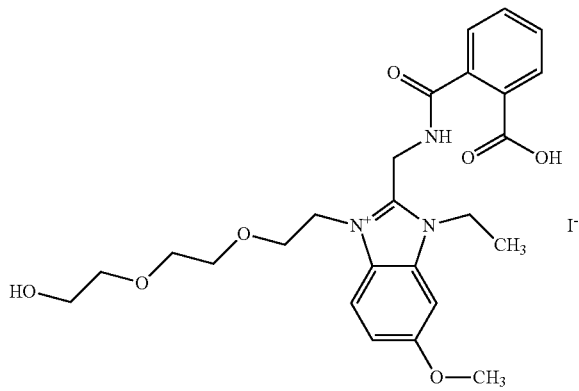 [SMILES: CCn1c(CNC(=O)c2ccccc2C(=O)O)[n+](CCOCCOCCO)c2ccc(OC)cc21 ; [I-]]

A mixture of 2-[(1-ethyl-6-methoxy-1H-1,3-benzodiazol-2-yl)methyl]-2,3-dihydro-1H-isoindole-1,3-dione, Intermediate 11 (2.00 g, 5.96 mmol) and 2-[2-(2-iodoethoxy)ethoxy]ethan-1-ol (90%, 8.62 g, 29.8 mmol) in MeCN (15 ml) was heated at 130° C. in a sealed tube for 16 h then allowed to cool to RT. The reaction mixture was concentrated in vacuo then the crude material was purified by flash column chromatography on C18 (12 g). The column was eluted with MeCN:H₂O+0.1% formic acid using the following gradient (% MeCN, column volumes): 10%, 2 CV; 10-14%, 2 CV; 14-18%, 1 CV; 18-27%, 2 CV; 27-31 CV, 0.5 CV; 31-60%, 0.5 CV; 60-100%, 1 CV; 100%, 1 CV. The desired fractions were combined and evaporated to yield the product as a yellow amorphous solid (1.72 g, 47%).

¹H NMR (500 MHz, DMSO-d₆) δ 12.97-12.91 (m, 1H), 7.96 (d, J=9.2 Hz, 1H), 7.72 (dd, J=7.8, 1.2 Hz, 1H), 7.60 (dd, J=7.7, 1.3 Hz, 1H), 7.57 (d, J=2.3 Hz, 1H), 7.37 (td, J=7.5, 1.4 Hz, 1H), 7.30-7.24 (m, 2H), 5.04 (d, J=5.0 Hz, 2H), 4.91 (t, J=4.8 Hz, 2H), 4.77-4.62 (m, 3H), 3.91 (s, 3H), 3.83 (t, J=4.9 Hz, 2H), 3.51-3.46 (m, 2H), 3.43-3.39 (m, 4H), 3.36-3.28 (m, 2H+HDO), 1.41 (t, J=7.2 Hz, 3H). NMR purity=92% LC/MS (System A): m/z (ESI⁺)=486 [M⁺], $R_t$=0.80 min, UV purity=100%.

Synthesis of 2-(aminomethyl)-1-ethyl-3-{2-[2-(2-hydroxyethoxy)ethoxy]ethyl}-6-methoxy-1H-1,3-benzodiazol-3-ium iodide: Intermediate 20

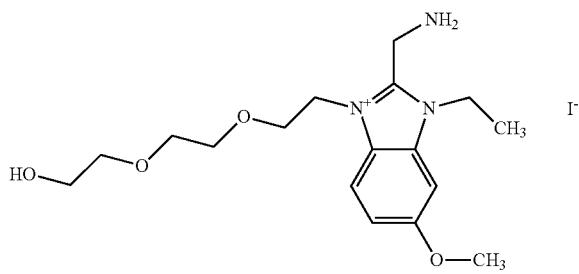 [SMILES: CCn1c(CN)[n+](CCOCCOCCO)c2ccc(OC)cc21 ; [I-]]

Hydrazine hydrate (639 μl, 13.2 mmol) was added to a solution of 2-{[(2-carboxyphenyl)formamido]methyl}-1-ethyl-3-{2-[2-(2-hydroxyethoxy)ethoxy]ethyl}-6-methoxy-1H-1,3-benzodiazol-3-ium iodide, Intermediate 19 (92%, 1.52 g, 2.28 mmol) in MeOH (12 ml) in a pressure tube. The tube was sealed and the reaction solution was heated at 75° C. for 3.5 h. The reaction was allowed to cool to RT then stirred at RT for 64 h. Additional hydrazine hydrate (639 μl, 13.2 mmol) was added and the reaction was heated at 75° C. for a further 18 h, then at 80° C. for a further 24 h. The reaction mixture was allowed to cool to RT then concentrated in vacuo to an orange solid. The solid thus obtained was suspended in CH₂Cl₂:MeOH (9:1, 30 ml) then filtered. The filtrate was concentrated in vacuo to afford the product as a viscous orange oil (1.21 g, 83%).

LC/MS (System B): m/z (ESI⁺)=338 [M⁺], $R_t$=1.41 min, UV purity=84%

Synthesis of 2-[(6-chloro-1-ethyl-1H-1,3-benzodiazol-2-yl)methyl]-2,3-dihydro-1H-isoindole-1,3-dione: Intermediate 21

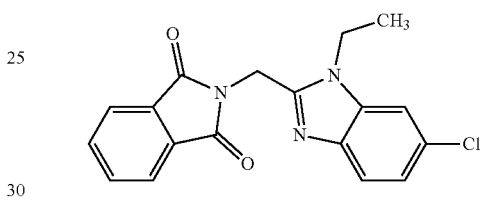

A mixture of N-phthaloylglycine (2.15 g, 10.5 mmol), TBTU (3.52 g, 11.0 mmol) and NEt₃ (2.31 ml, 13.0 mmol) in anhydrous DMF (30 ml) was stirred at RT for 45 min. A solution of 5-chloro-1-N-ethylbenzene-1,2-diamine (1.70 g, 9.96 mmol) in anhydrous THF (20 ml) was added and the resulting mixture was stirred at RT for 18 h. The reaction mixture was added to saturated aq. NaHCO₃ solution (100 ml) which caused a pale brown solid to precipitate from solution. The solid was filtered, washed with water and dried under vacuum. The solid thus obtained was triturated in MeCN then filtered and dried under vacuum to afford the intermediate as a pale pink solid (5.4 g). The solid thus obtained was added portion-wise to acetic acid (30 ml). The resulting suspension was heated at 100° C. for 45 min then allowed to cool to RT over 16 h. The resulting suspension was filtered and washed with EtOAc then dried under vacuum to afford the product as a pale pink solid (585 mg). The solid was suspended in MeCN (5 ml) then MeCN:water (1:1, 1 ml) was added. The resulting suspension was filtered then the solid was dried under vacuum to afford the product as a pale pink solid (430 mg, 13%). The filtrate was again filtered, then the solid was washed with EtOAc and dried under vacuum to afford a second batch of product as a pale pink solid (2.00 g). The solid was suspended in MeCN (20 ml) then MeCN:water (1:1, 5 ml) was added. The resulting suspension was filtered then the solid was dried under vacuum to afford second batch of the product as a pale pink solid (1.33 g, 38%). The two batches of product were combined as a suspension in MeCN then concentrated and dried under vacuum to afford the product as a pale pink solid (1.76 g, 51%).

¹H NMR (250 MHz, DMSO-d₆) δ 8.02-7.85 (m, 4H), 7.76 (d, J=1.9 Hz, 1H), 7.49 (d, J=8.6 Hz, 1H), 7.15 (dd, J=8.6, 2.0 Hz, 1H), 5.13 (s, 2H), 4.39 (q, J=7.1 Hz, 2H), 1.37 (t, J=7.2 Hz, 3H).

LC/MS (System A): m/z (ESI$^+$)=340 [M($^{35}$Cl)H$^+$], 342 [M($^{37}$Cl)H$^+$], R$_t$=1.12 min, UV purity=99%.

Synthesis of 6-chloro-2-[(1,3-dioxo-2,3-dihydro-1H-isoindol-2-yl)methyl]-1-ethyl-3-methyl-1H-1,3-benzodiazol-3-ium iodide: Intermediate 22

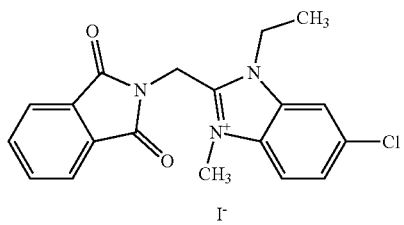 [SMILES: CCn1c(CN2C(=O)c3ccccc3C2=O)[n+](C)c2ccc(Cl)cc21 ; [I-]]

A mixture of 2-[(6-chloro-1-ethyl-1H-1,3-benzodiazol-2-yl)methyl]-2,3-dihydro-1H-isoindole-1,3-dione, Intermediate 21 (600 mg, 1.77 mmol) and iodomethane (330 μl, 5.30 mmol) in MeCN (6 ml) was heated at 75° C. in a sealed tube for 1.5 h then allowed to cool to RT. Iodomethane (165 μl, 2.65 mmol) was added then the reaction was heated at 80° C. for 5 h. The reaction was allowed to cool to RT then filtered to afford a solid which was washed with MeCN and dried under vacuum to afford the product as a yellow solid (644 mg, 73%).

$^1$H NMR (500 MHz, DMSO-d$_6$) δ 8.40 (d, J=1.8 Hz, 1H), 8.13 (d, J=8.9 Hz, 1H), 7.91 (m, 4H), 7.79 (dd, J=8.9, 1.9 Hz, 1H), 5.40 (s, 2H), 4.74 (q, J=7.2 Hz, 2H), 4.14 (s, 3H), 1.43 (t, J=7.2 Hz, 3H).

LC/MS (System A): m/z (ESI$^+$)=354 [M($^{35}$Cl)$^+$], 356 [M($^{37}$Cl)$^+$], R$_t$=0.90 min, UV purity=97%.

Synthesis of 2-(aminomethyl)-6-chloro-1-ethyl-3-methyl-1H-1,3-benzodiazol-3-ium iodide: Intermediate 23

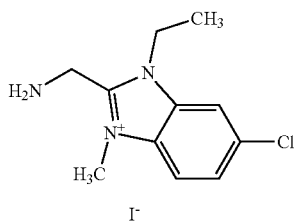

Hydrazine hydrate (446 μl, 9.17 mmol) was added to a suspension of 6-chloro-2-[(1,3-dioxo-2,3-dihydro-1H-isoindol-2-yl)methyl]-1-ethyl-3-methyl-1H-1,3-benzodiazol-3-ium iodide, Intermediate 22 (640 mg, 1.33 mmol) in MeOH (8 ml) in a pressure tube. The tube was sealed and heated at 75° C. for 3 h then allowed to cool to RT. The resulting suspension was filtered and the solid was washed with MeOH (10 ml). The filtrate was evaporated to dryness to afford an orange solid, which was suspended in CH$_2$Cl$_2$ (10 ml) then filtered and washed through with CH$_2$Cl$_2$. The solid thus obtained was suspended in CH$_2$Cl$_2$ (10 ml). A few drops of MeOH were added and the suspension was sonicated. The resulting suspension was filtered then the solid was dried under vacuum to afford the product as an off-white solid (360 mg, 77%).

$^1$H NMR (500 MHz, DMSO-d) δ 8.31 (d, J=1.9 Hz, 1H), 8.06 (d, J=8.9 Hz, 1H), 7.73 (dd, J=8.8, 1.9 Hz, 1H), 4.60 (q, J=7.2 Hz, 2H), 4.25 (s, 2H), 4.06 (s, 3H), 1.41 (t, J=7.2 Hz, 3H).

LC/MS (System A): m/z (ESI$^+$)=224 [M($^{35}$Cl)$^+$], 226 [M($^{37}$Cl)$^+$], R$_t$=0.16 min, ELS purity=100%.

Synthesis of tert-butyl N-[(1-ethyl-6-fluoro-1H-1,3-benzodiazol-2-yl)methyl]carbamate: Intermediate 24

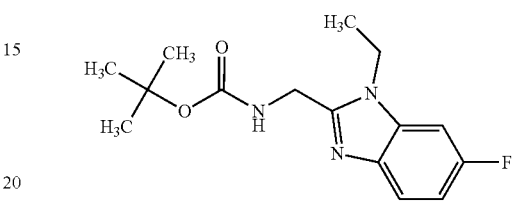

A solution of 2-{[(tert-butoxy)carbonyl]amino}acetic acid (1.70 g, 9.73 mmol), HATU (4.07 g, 10.7 mmol) and DIPEA (3.39 ml, 19.5 mmol) in anhydrous DMF (20 ml) was stirred at RT for 20 min. A solution of 1-N-ethyl-5-fluorobenzene-1,2-diamine (1.05 g, 9.73 mmol) in anhydrous THF (10 ml) was added and the resulting mixture was stirred at RT for 16 h. The reaction mixture was poured onto saturated aq. NaHCO$_3$ solution (80 ml). EtOAc (100 ml) and water (50 ml) were added then the phases were separated. The aqueous phase was extracted with EtOAc (2×50 ml) then the combined organic phases were washed with water (4×50 ml) and brine (50 ml), then dried over Na$_2$SO$_4$, filtered and evaporated to afford the intermediate as a black oil (4 g). The intermediate was dissolved in acetic acid (30 ml) then heated at 60° C. for 4 h. The reaction mixture was allowed to cool to RT then stirred at RT for 16 h. The resulting mixture was evaporated then the resulting residue was partitioned between EtOAc (150 ml) and water (100 ml). The aqueous phase was extracted with EtOAc (50 ml) then the combined organic phases were washed with water (4×50 ml) and brine (50 ml), then dried over Na$_2$SO$_4$, filtered and evaporated to a black solid (4 g). The solid was dissolved in the minimum of CH$_2$Cl$_2$/MeOH then evaporated onto silica (9 g). The crude material was purified by flash column chromatography on a silica column (120 g). The column was eluted with CH$_2$Cl$_2$:MeOH, increasing the gradient linearly from 100:0 to 95:5 over 10 column volumes. The desired fractions were combined and evaporated to a black solid (2.9 g). The solid thus obtained was dissolved in EtOAc (100 ml) and extracted with saturated aqueous sodium bicarbonate solution (3×50 ml) and water (50 ml) then dried over Na$_2$SO$_4$, filtered and evaporated to a black solid (2.5 g). The solid was dissolved in the minimum of CH$_2$Cl$_2$/MeOH then evaporated onto silica (10 g). The material was further purified by flash column chromatography on a silica column (120 g). The column was eluted with EtOAc:heptane, increasing the gradient linearly from 0:100 to 100:0 over 10 column volumes. The desired fractions were combined and evaporated to afford the product as a pink solid (1.78 g, 62%).

¹H NMR (500 MHz, DMSO-d₆) δ 7.56 (dd, J=8.8, 4.9 Hz, 1H), 7.50-7.41 (m, 2H), 7.01 (m, 1H), 4.42 (d, J=5.9 Hz, 2H), 4.24 (q, J=7.2 Hz, 2H), 1.45-1.20 (m, 12H).

LC/MS (System A): m/z (ESI⁺)=294 [MH⁺], R$_t$=0.92 min, UV purity=100%.

Synthesis of 2-({[(tert-butoxy)carbonyl]amino}methyl)-1-ethyl-6-fluoro-3-methyl-1H-1,3-benzodiazol-3-ium iodide: Intermediate 25

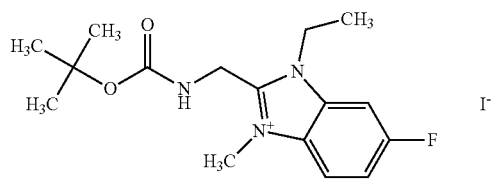 [SMILES: CCn1c(CNC(=O)OC(C)(C)C)[n+](C)c2ccc(F)cc21 ; [I-]]

Iodomethane (497 μl, 7.98 mmol) was added to a suspension of tert-butyl N-[(1-ethyl-6-fluoro-1H-1,3-benzodiazol-2-yl)methyl]carbamate, Intermediate 24 (0.78 g, 2.66 mmol) in anhydrous MeCN (12 ml) in a pressure tube. The tube was sealed then heated at 75° C. for 4 h. The reaction mixture was allowed to cool to RT then concentrated in vacuo to afford the product as a pale yellow solid (1.16 g, 99%).

¹H NMR (500 MHz, DMSO-d₆) δ 8.14-8.04 (m, 2H), 7.94 (t, J=5.2 Hz, 1H), 7.68-7.56 (m, 1H), 4.73 (d, J=5.4 Hz, 2H), 4.58 (q, J=7.2 Hz, 2H), 4.08 (s, 3H), 1.38 (m, 12H).

LC/MS (System A): m/z (ESI⁺)=308 [M⁺], R$_t$=0.87 min, UV purity=99%.

Synthesis of 2-(aminomethyl)-1-ethyl-6-fluoro-3-methyl-1H-1,3-benzodiazol-3-ium hydrochloride iodide: Intermediate 26

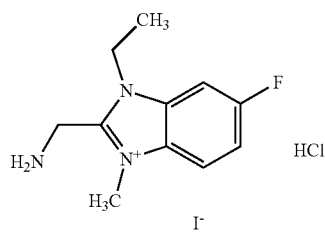

HCl solution in dioxane (4.0 M, 3.3 ml, 13.2 mmol) was added to a solution of 2-({[(tert-butoxy)carbonyl]amino}methyl)-1-ethyl-6-fluoro-3-methyl-1H-1,3-benzodiazol-3-ium iodide, Intermediate 25 (1.16 g, 2.66 mmol) in MeCN (5 ml). The reaction was stirred at RT for 0.5 h then concentrated in vacuo. The solid was azeotroped with MeCN (10 ml) then dried under vacuum to yield the product as a yellow/green solid (870 mg, 88%).

¹H NMR (500 MHz, DMSO-d₆) δ 9.21 (s, 3H), 8.25-8.14 (m, 2H), 7.69 (td, J=9.3, 2.4 Hz, 1H), 4.76 (s, 2H), 4.70 (q, J=7.2 Hz, 2H), 4.19 (s, 3H), 1.42 (t, J=7.2 Hz, 3H).

LC/MS (System A): m/z (ESI⁺)=208 [M⁺], R$_t$=0.14 min, ELS purity=100%.

Synthesis of tert-butyl N-{[1-ethyl-6-(trifluoromethyl)-1H-1,3-benzodiazol-2-yl]methyl}carbamate: Intermediate 27

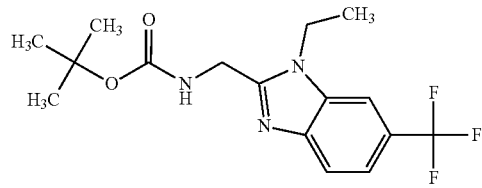 [SMILES: CCn1c(CNC(=O)OC(C)(C)C)nc2ccc(C(F)(F)F)cc21]

Intermediate 27 was synthesised according to literature procedures (WO 2009019506 A1).

Synthesis of 2-({[(tert-butoxy)carbonyl]amino}methyl)-1-ethyl-3-methyl-6-(trifluoromethyl)-1H-1,3-benzodiazol-3-ium iodide: Intermediate 28

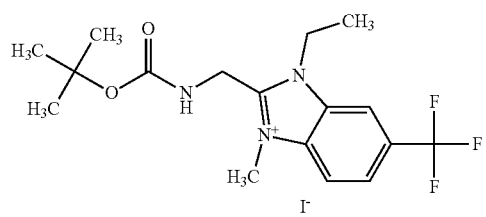 [SMILES: CCn1c(CNC(=O)OC(C)(C)C)[n+](C)c2ccc(C(F)(F)F)cc21 ; [I-]]

Iodomethane (381 μl, 6.12 mmol) was added to a suspension of tert-butyl N-{[1-ethyl-6-(trifluoromethyl)-1H-1,3-benzodiazol-2-yl]methyl}carbamate, Intermediate 27 (700 mg, 2.04 mmol) in anhydrous MeCN (10 ml) in a pressure tube. The tube was sealed and heated at 75° C. for 8 h then allowed to cool to RT. The reaction mixture was concentrated in vacuo to afford the product as a pale yellow solid (1.01 g, >99%).

1H NMR (500 MHz, DMSO-d6) δ 8.64 (s, 1H), 8.29 (d, J=8.7 Hz, 1H), 8.08 (d, J=8.7 Hz, 1H), 7.98 (t, J=5.2 Hz, 1H), 4.80 (s, 2H), 4.73 (q, J=7.2 Hz, 2H), 4.14 (s, 3H), 1.40 (m, 12H).

LC/MS (System A): m/z (ESI⁺)=358 [M⁺], R$_t$=0.91 min, UV purity=98%.

Synthesis of 2-(aminomethyl)-1-ethyl-3-methyl-6-(trifluoromethyl)-1H-1,3-benzodiazol-3-ium hydrochloride iodide: Intermediate 29

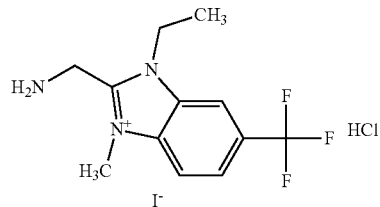 [SMILES: CCn1c(CN)[n+](C)c2ccc(C(F)(F)F)cc21 ; Cl ; [I-]]

HCl solution in dioxane (4.0 M, 2.8 ml, 11 mmol) was added to a solution of 2-({[(tert-butoxy)carbonyl]amino}methyl)-1-ethyl-3-methyl-6-(trifluoromethyl)-1H-1, 3-benzodiazol-3-ium iodide, Intermediate 28 (1.07 g, 2.21 mmol) in MeCN (5 ml). The reaction was stirred at RT for 16 h then concentrated in vacuo to yield the product as an off-white solid (875 mg, 94%).

$^1$H NMR (500 MHz, DMSO-$d_6$) δ 9.14 (s, 3H), 8.74 (s, 1H), 8.38 (d, J=8.8 Hz, 1H), 8.14 (dd, J=8.8, 1.3 Hz, 1H), 4.84 (m, 4H), 4.24 (s, 3H), 1.45 (t, J=7.2 Hz, 3H).

LC/MS (System A): m/z (ESI$^+$)=258 [M$^+$], R$_t$=0.17 min, ELS purity=100%.

Synthesis of
N-ethyl-2-nitro-5-(trifluoromethoxy)aniline:
Intermediate 30

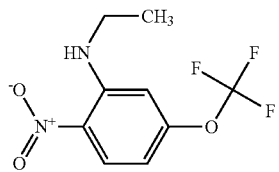

Two identical reactions were carried out in parallel as follows then combined for work-up. Ethylamine solution in THF (2.0 M, 4.1 ml, 8.2 mmol) was added to a suspension of 2-chloro-1-nitro-4-(trifluoromethoxy)benzene (1.00 g, 4.14 mmol) and K$_2$CO$_3$ (0.86 g, 6.21 mmol) in THF (12 ml) in a pressure tube. The tube was sealed then heated at 50° C. for 16 h then allowed to cool to RT. Additional ethylamine solution in THF (2.0 M, 2.1 ml, 4.2 mmol) was added then the reaction was heated at 50° C. for 24 h. The combined reactions were filtered then the solid thus obtained was rinsed with EtOAc (100 ml). The combined filtrates were extracted with saturated aq. NaHCO$_3$ solution (2×100 ml), water (50 ml) and brine (50 ml) then dried over Na$_2$SO$_4$, then filtered and evaporated to an orange oil. The crude material was purified by flash column chromatography on C18 (120 g). The column was eluted with MeCN:H$_2$O using the following gradient (% MeCN, column volumes): 10%, 2 CV; 10-100%, 20 CVs; 100%, 2 CV. The desired fractions were combined and concentrated in vacuo to remove most of the MeCN. The residual aqueous mixture was extracted with EtOAc (100 ml). The organic phase was separated, then dried over Na$_2$SO$_4$ and evaporated to afford the product as a bright orange oil (1.42 g, 69%).

$^1$H NMR (500 MHz, CDCl$_3$) δ 8.23 (d, J=9.4 Hz, 1H), 8.04 (s, 1H), 6.61 (d, J=2.0 Hz, 1H), 6.48 (ddd, J=9.4, 2.4, 1.2 Hz, 1H), 3.33 (qd, J=7.2, 5.1 Hz, 2H), 1.39 (t, J=7.2 Hz, 3H).

LC/MS (System A): m/z (ESI$^+$)=251 [MH$^+$], R$_t$=1.32 min, UV purity=100%.

Synthesis of tert-butyl N-{[1-ethyl-6-(trifluoromethoxy)-1H-1,3-benzodiazol-2-yl]methyl} carbamate: Intermediate 31

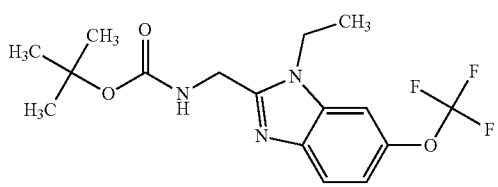 [SMILES: CCn1c(CNC(=O)OC(C)(C)C)nc2ccc(OC(F)(F)F)cc21]

A suspension of palladium on carbon (10 wt. %, 0.3 g) and N-ethyl-2-nitro-5-(trifluoromethoxy)aniline, Intermediate 30 (1.42 g, 5.68 mmol) solution in EtOH (40 ml) was stirred under a hydrogen atmosphere (1 atm) at RT for 16 h. The reaction mixture was filtered through glass fibre filter paper and washed through with EtOAc. The filtrate was concentrated to near dryness in vacuo and then diluted with anhydrous THF (10 ml). The resulting solution was added to a pre-mixed solution of 2-{[(tert-butoxy)carbonyl]amino}acetic acid (994 mg, 5.68 mmol), HATU (2.37 g, 6.24 mmol) and DIPEA (1.98 ml, 11.4 mmol) in anhydrous DMF (20 ml). The reaction mixture was stirred at RT for 68 h then poured onto saturated aqueous NaHCO$_3$ (80 ml). EtOAc (50 ml) and water (50 ml) were added and the phases were separated. The aqueous phase was extracted with EtOAc (2×50 ml) then the combined organic phases were washed with water (4×50 ml) and brine (50 ml) then dried over Na$_2$SO$_4$, filtered and evaporated to a black oil. The oil thus obtained was dissolved in acetic acid (10 ml) and the resulting solution was heated at 70° C. for 1.5 h. The reaction solution was concentrated in vacuo then the residue was partitioned between EtOAc (50 ml) and saturated aq. NaHCO$_3$ solution (50 ml). The organic phase was washed with saturated aq. NaHCO$_3$ solution (4×50 ml), water (50 ml) and brine (10 ml) then dried over Na$_2$SO$_4$, filtered and evaporated to a brown solid (1.95 g). The crude material was dissolved in CH$_2$Cl$_2$/MeOH then evaporated onto silica (10 g) and purified by flash column chromatography on a silica column (120 g).

The column was eluted with EtOAc:heptane, increasing the gradient linearly from 0:100 to 100:0 over 10 column volumes. The desired fractions were combined and evaporated to yield the product as a pink solid (1.04 g, 47%).

$^1$H NMR (500 MHz, DMSO-$d_6$) δ 7.70-7.61 (m, 2H), 7.49 (d, J=5.1 Hz, 1H), 7.19-7.10 (m, 1H), 4.44 (d, J=5.9 Hz, 2H), 4.29 (q, J=7.1 Hz, 2H), 1.45-1.23 (m, 12H).

LC/MS (System A): m/z (ESI$^+$)=360 [MH$^+$], R$_t$=1.11 min, UV purity=92%.

Synthesis of 2-({[(tert-butoxy)carbonyl]amino}methyl)-1-ethyl-3-methyl-6-(trifluoromethoxy)-1H-1,3-benzodiazol-3-ium iodide: Intermediate 32

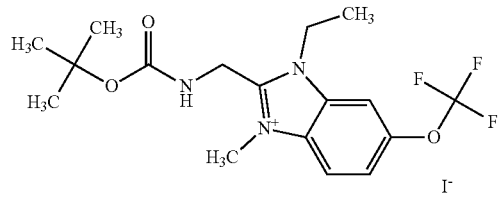 [SMILES: CCn1c(CNC(=O)OC(C)(C)C)[n+](C)c2ccc(OC(F)(F)F)cc21 ; [I-]]

Iodomethane (208 μl, 3.34 mmol) was added to a suspension of tert-butyl N-{[1-ethyl-6-(trifluoromethoxy)-1H-1,3-benzodiazol-2-yl]methyl} carbamate, Intermediate 31 (400 mg, 1.11 mmol) in anhydrous MeCN (5 ml) in a pressure tube. The tube was sealed then heated at 75° C. for 5 h then allowed to cool to RT. The reaction mixture was concentrated in vacuo to yield the product as a dark green solid (567 mg, 95%).

$^1$H NMR (500 MHz, DMSO-d$_6$) δ 8.30 (s, 1H), 8.18 (d, J=9.1 Hz, 1H), 7.95 (t, J=5.2 Hz, 1H), 7.76 (d, J=9.1 Hz, 1H), 4.75 (d, J=5.4 Hz, 2H), 4.64 (q, J=7.1 Hz, 2H), 4.10 (s, 3H), 1.38 (m, 12H).

LC/MS (System A): m/z (ESI$^+$)=374 [M$^+$], R$_t$=0.96 min, UV purity=93%.

Synthesis of 2-(aminomethyl)-1-ethyl-3-methyl-6-(trifluoromethoxy)-1H-1,3-benzodiazol-3-ium hydrochloride iodide: Intermediate 33

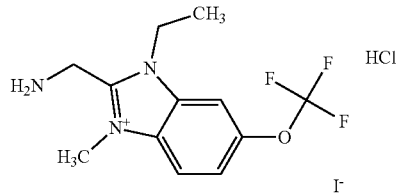 [SMILES: CCn1c(CN)[n+](C)c2ccc(OC(F)(F)F)cc21 ; Cl ; [I-]]

HCl solution in dioxane (4.0 M, 1.4 ml, 5.6 mmol) was added to a solution of 2-({[(tert-butoxy)carbonyl]amino}methyl)-1-ethyl-3-methyl-6-(trifluoromethoxy)-1H-1,3-benzodiazol-3-ium iodide, Intermediate 32 (570 mg, 1.14 mmol) in MeCN (5 ml). The reaction was left to stir at RT for 16 h then concentrated in vacuo. The solid was azeotroped with MeCN (10 ml) then dried under vacuum to yield the product as a brown solid (480 mg, 84%).

$^1$H NMR (500 MHz, DMSO-d$_6$) δ 9.11 (s, 3H), 8.40 (d, J=1.6 Hz, 1H), 8.28 (d, J=9.1 Hz, 1H), 7.83 (dd, J=9.1, 1.2 Hz, 1H), 4.80 (s, 2H), 4.75 (q, J=7.2 Hz, 2H), 4.21 (s, 3H), 1.42 (t, J=7.2 Hz, 3H).

LC/MS (System A): m/z (ESI$^+$)=274 [M$^+$], R$_t$=0.37 min, ELS purity=87%.

Synthesis of methyl 2-({[(tert-butoxy)carbonyl]amino}methyl)-1-ethyl-1H-1,3-benzodiazole-6-carboxylate: Intermediate 34

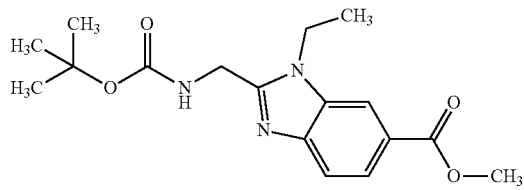 [SMILES: CCn1c(CNC(=O)OC(C)(C)C)nc2ccc(C(=O)OC)cc21]

A mixture of 2-{[(tert-butoxy)carbonyl]amino}acetic acid (8.57 g, 48.9 mmol), HATU (20.5 g, 53.8 mmol) and DIPEA (17.0 ml, 97.8 mmol) in DMF (200 ml) was stirred at RT for 1 h. Methyl 4-amino-3-(ethylamino)benzoate (8.57 g, 48.9 mmol) was added portionwise then rinsed into the reaction with anhydrous THF (20 ml). The reaction mixture was stirred at RT for 18 h. A solution of 2-{[(tert-butoxy)carbonyl]amino}acetic acid (0.857 g, 4.89 mmol), HATU (1.86 g, 4.89 mmol) and DIPEA (1.70 ml, 9.78 mmol) in DMF (3 ml) was stirred at RT for 15 min then added to the main reaction. The resulting solution was stirred at RT for 3 h. A solution of 2-{[(tert-butoxy)carbonyl]amino}acetic acid (0.857 g, 4.89 mmol), HATU (1.86 g, 4.89 mmol) and DIPEA (1.70 ml, 9.78 mmol) in DMF (3 ml) and stirred at RT for 15 min then added to the main reaction. The resulting solution was stirred at RT for 64 h. The reaction mixture was poured onto saturated aqueous NaHCO$_3$ solution (200 ml). EtOAc (150 ml) and water (100 ml) were added then the phases were separated. The aqueous phase was extracted with EtOAc (2×150 ml), then the combined organic phases were washed with water (4×100 ml) and brine (50 ml) then dried over Na$_2$SO$_4$, filtered and evaporated to afford the crude intermediate as a black oil (18 g). The oil thus obtained was dissolved in acetic acid (80 ml) and stirred at 70° C. for 1 h. The reaction was allowed to cool to RT then evaporated to afford a brown solid. The solid was suspended in EtOAc (200 ml) then filtered and was washed with EtOAc, then dried under vacuum to afford a pale pink solid (6.5 g). The solid thus obtained was suspended in EtOAc (200 ml). The resulting suspension was heated at 50° C. for 15 min then allowed to cool to RT. The solid was collected by filtration to afford the product as a white solid (2.43 g). The filtrate was again filtered and the solid was collected by filtration, washed with EtOAc:heptane then dried under vacuum to afford a second batch of the product as a white solid (1.34 g). The filtrate was transferred to a separating funnel then extracted with saturated aqueous NaHCO$_3$ solution (3×100 ml), water (100 ml) and brine (50 ml) then dried over Na$_2$SO$_4$, filtered and evaporated to a yellow solid which was suspended in the minimum volume of EtOAc:heptane (1:4) and filtered then dried under vacuum to afford a third batch of the product as a white solid (1.77 g). The filtrate from the first filtration was transferred to a separating funnel then extracted with saturated aqueous NaHCO$_3$ solution (3×100 ml), water (100 ml) and brine (50 ml) then dried over Na$_2$SO$_4$, filtered and evaporated to a dark brown solid. The solid was suspended in EtOAc (50 ml) then filtered. The solid was dried under vacuum to afford a fourth batch of the product as a white solid (3.4 g). The filtrate was evaporated to afford a dark solid (8 g). The solid thus obtained was dissolved in CH$_2$Cl$_2$/MeOH then evaporated onto silica (16 g). The crude material was purified by flash column chromatography on a silica column (100 g). The column was eluted with EtOAc:heptane, increasing the gradient linearly from 0:100 to 100:0 over 10 column volumes. The desired fractions were combined and evaporated to a brown solid. The solid thus obtained was suspended in EtOAc:heptane (1:4, 20 ml) then filtered. The solid was washed with EtOAc:heptane then dried under vacuum to afford a fifth batch of the product as a white solid (1.45 g). The filtrate was concentrated in vacuo then the residue was suspended in EtOAc, filtered and dried under vacuum to afford a sixth batch of the product as an off-white solid (0.32 g). The 6 batches of solid were combined as an EtOAc suspension then evaporated and dried under vacuum to yield the product as an off-white solid (10.71 g, 66%).

$^1$H NMR (500 MHz, DMSO-d$_6$) δ 8.16 (d, J=1.1 Hz, 1H), 7.82 (dd, J=8.4, 1.6 Hz, 1H), 7.66 (d, J=8.4 Hz, 1H), 7.52 (d, J=5.3 Hz, 1H), 4.47 (d, J=5.8 Hz, 2H), 4.35 (q, J=7.2 Hz, 2H), 3.88 (s, 3H), 1.46-1.22 (m, 12H).

LC/MS (System A): m/z (ESI$^+$)=334 [MH$^-$], R$_t$=0.98 min, UV purity=100%.

Synthesis of 2-({[(tert-butoxy)carbonyl]amino}methyl)-1,3-diethyl-6-(methoxycarbonyl)-1H-1,3-benzodiazol-3-ium iodide: Intermediate 35

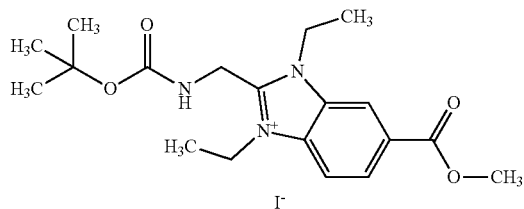 [SMILES: CCn1c(CNC(=O)OC(C)(C)C)[n+](CC)c2ccc(C(=O)OC)cc21 ; [I-]]

Iodoethane (969 µl, 12.1 mmol) was added to a suspension of methyl 2-({[(tert-butoxy)carbonyl]amino}methyl)-1-ethyl-1H-1,3-benzodiazole-6-carboxylate, Intermediate 34 (1.34 g, 4.02 mmol) in anhydrous MeCN (15 ml) in a pressure tube. The tube was sealed then heated at 80° C. for 21 h then allowed to cool to RT. Iodoethane (323 µl, 4.02 mmol) was added then the reaction was heated at 80° C. for 5 h then allowed to cool to RT. Iodoethane (646 µl, 8.04 mmol) was added then the reaction was heated at 80° C. for 16 h. The reaction was allowed to cool to RT then evaporated to afford the product as a pink foam (1.97 g, >99%).

$^1$H NMR (500 MHz, DMSO-$d_6$) δ 8.65 (s, 1H), 8.28-8.18 (m, 2H), 8.00 (t, J=5.2 Hz, 1H), 4.82 (d, J=5.3 Hz, 2H), 4.72 (q, J=7.2 Hz, 2H), 4.64 (q, J=7.2 Hz, 2H), 3.96 (s, 3H), 1.50-1.31 (m, 15H).

LC/MS (System A): m/z (ESI$^+$)=362 [M$^+$], R$_t$=0.92 min, UV purity=100%.

Synthesis of 2-(aminomethyl)-1,3-diethyl-6-(methoxycarbonyl)-1H-1,3-benzodiazol-3-ium hydrochloride iodide: Intermediate 36

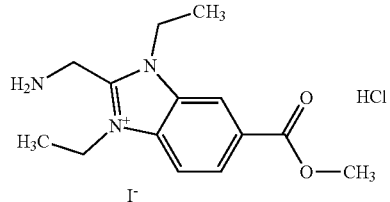 [SMILES: CCn1c(CN)[n+](CC)c2ccc(C(=O)OC)cc21 ; Cl ; [I-]]

HCl solution in dioxane (4.0 M, 5.1 ml, 20.4 mmol) was added to a solution of 2-({[(tert-butoxy)carbonyl]amino}methyl)-1,3-diethyl-6-(methoxycarbonyl)-1H-1,3-benzodiazol-3-ium iodide, Intermediate 35 (1.98 g, 4.05 mmol) in MeCN (10 ml). The reaction was stirred at RT for 1.5 h then concentrated in vacuo to afford the product as a yellow solid (1.60 g, 93%).

$^1$H NMR (500 MHz, DMSO-$d_6$) δ 9.13 (s, 3H), 8.72 (s, 1H), 8.34-8.23 (m, 2H), 4.87-4.65 (m, 6H), 3.96 (s, 3H), 1.47 (m, 6H).

LC/MS (System A): m/z (ESI$^+$)=262 [M$^+$], R$_t$=0.16 min, ELS purity=100%.

Synthesis of methyl 2-(aminomethyl)-1-ethyl-1H-1,3-benzodiazole-6-carboxylate dihydrochloride: Intermediate 37

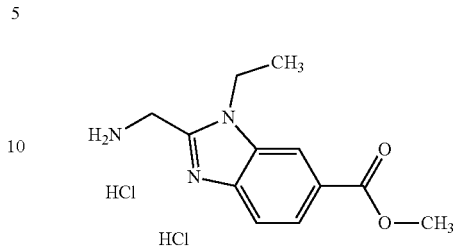

HCl solution in dioxane (4.0 M, 5.4 ml, 21.6 mmol) was added to a solution of methyl 2-({[(tert-butoxy)carbonyl]amino}methyl)-1-ethyl-1H-1,3-benzodiazole-6-carboxylate, Intermediate 34 (1.45 g, 4.35 mmol) in MeCN (10 ml). The reaction was left to stir at RT for 45 min then filtered. The solid was washed with MeCN then dried under vacuum to afford the product as a white solid (1.29 g, 97%).

$^1$H NMR (500 MHz, DMSO-$d_6$) δ 8.75 (s, 3H), 8.30-8.21 (m, 1H), 7.89 (dd, J=8.5, 1.6 Hz, 1H), 7.77 (d, J=8.5 Hz, 1H), 4.50 (d, J=5.6 Hz, 2H), 4.39 (q, J=7.2 Hz, 2H), 3.89 (s, 3H), 1.34 (t, J=7.2 Hz, 3H).

LC/MS (System A): m/z (ESI$^+$)=234 [MH$^+$], R$_t$=0.67 min, UV purity=100%.

Synthesis of methyl 2-({[(benzyloxy)carbonyl]amino}methyl)-1-ethyl-1H-1,3-benzodiazole-6-carboxylate: Intermediate 38

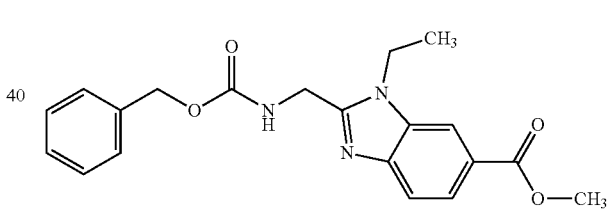

Triethylamine (2.04 ml, 14.6 mmol) was added to a suspension of methyl 2-(aminomethyl)-1-ethyl-1H-1,3-benzodiazole-6-carboxylate dihydrochloride Intermediate 37 (1.29 g, 4.21 mmol) in CH$_2$Cl$_2$ (22 ml). A solution of benzyl 2,5-dioxopyrrolidin-1-yl carbonate (1.15 g, 4.63 mmol) CH$_2$Cl$_2$ (10 ml) was added dropwise then the reaction mixture was stirred at RT for 15 min. The reaction mixture was extracted with water (20 ml), saturated aqueous NaHCO$_3$ solution (2×10 ml), water (20 ml) and brine (10 ml), then dried over Na$_2$SO$_4$, filtered and evaporated to afford the product as a white solid (1.65 g, 92%)

$^1$H NMR (500 MHz, DMSO-$d_6$) δ 8.17 (s, 1H), 7.99 (t, J=5.8 Hz, 1H), 7.83 (dd, J=8.4, 1.5 Hz, 1H), 7.68 (d, J=8.4 Hz, 1H), 7.49-7.28 (m, 5H), 5.07 (s, 2H), 4.56 (d, J=5.9 Hz, 2H), 4.36 (q, J=7.1 Hz, 2H), 3.89 (s, 3H), 1.30 (t, J=7.1 Hz, 3H).

LC/MS (System A): m/z (ESI$^+$)=368 [MH$^+$], R$_t$=1.02 min, UV purity=86%.

Synthesis of 2-({[(benzyloxy)carbonyl]amino}methyl)-1-ethyl-1H-1,3-benzodiazole-6-carboxylic acid: Intermediate 39

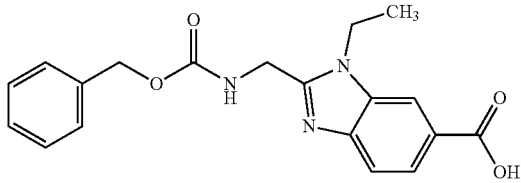 [SMILES: CCn1c(CNC(=O)OCc2ccccc2)nc2ccc(C(=O)O)cc21]

Aqueous LiOH solution (2.0 M, 2.4 ml, 4.8 mmol) was added to a suspension of methyl 2-({[(benzyloxy)carbonyl]amino}methyl)-1-ethyl-1H-1,3-benzodiazole-6-carboxylate, Intermediate 38 (1.33 g, 3.62 mmol) in MeOH (20 ml). The reaction mixture was stirred at 50° C. for 17 h then allowed to cool to RT. The reaction mixture was filtered then the filtrate was concentrated in vacuo to remove most of the MeOH. Three quarters of the resulting aqueous solution was purified by flash column chromatography on C18 (60 g). The column was eluted with MeCN:H$_2$O+0.1% formic acid using the following gradient (% MeCN, column volumes): 5%, 5 CV; 5-100%, 20 CV; 100%, 2 CV. The fractions were analysed by LCMS then the purest fractions were combined and filtered to afford the product as a white solid (92 mg). The filtrate was concentrated in vacuo to afford a second batch of product as an off-white solid (48 mg). Product-containing fractions of lesser purity were combined and evaporated to afford an off-white solid, which was suspended in EtOAc then filtered and dried under vacuum to afford a third batch of product as an off-white solid (96 mg). EtOAc (10 ml) was added to the remaining aqueous reaction mixture. The phases were separated then the aqueous phase was extracted further with EtOAc (10 ml). The aqueous phase was neutralised by dropwise addition of aqueous HCl solution (2 M). The solid was collected by filtration then dried under vacuum to afford a fourth batch of product as a white solid (134 mg). The filtrate was acidified further to pH 4 by addition of aqueous HCl solution (2 M) then extracted with EtOAc (4×20 ml). The combined organics were dried over Na$_2$SO$_4$, filtered and evaporated to afford a fifth batch of product as an off-white solid (100 mg). The five batches of product were combined as a suspension in EtOAc then evaporated to afford the product as an off-white solid (470 mg, 37%).

$^1$H NMR (500 MHz, DMSO-d$_6$) δ 12.77 (s, 1H), 8.13 (s, 1H), 7.97 (t, J=5.8 Hz, 1H), 7.80 (dd, J=8.4, 1.4 Hz, 1H), 7.64 (d, J=8.4 Hz, 1H), 7.34 (m, 5H), 5.06 (m, 2H), 4.54 (d, J=5.9 Hz, 2H), 4.34 (q, J=6.9 Hz, 2H), 1.29 (t, J=7.1 Hz, 3H).

LC/MS (System A): m/z (ESI$^+$)=354 [MH$^+$], R$_t$=0.87 min, UV purity=100%.

Synthesis of tert-butyl 2-({[(benzyloxy)carbonyl]amino}methyl)-1-ethyl-1H-1,3-benzodiazole-6-carboxylate: Intermediate 40

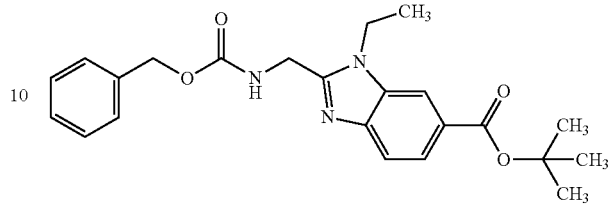

1,1-Di-tert-butoxy-N,N-dimethylmethanamine (1.03 ml, 4.30 mmol) was added to a suspension of 2-({[(benzyloxy)carbonyl]amino}methyl)-1-ethyl-1H-1,3-benzodiazole-6-carboxylic acid, Intermediate 39 (380 mg, 1.08 mmol) in toluene (10 ml). The reaction was heated at 80° C. for 2 h then allowed to cool to RT. 1,1-Di-tert-butoxy-N,N-dimethylmethanamine (1.03 ml, 4.30 mmol) was added then the reaction was heated at 80° C. for 3 h then allowed to cool to RT. 1,1-Di-tert-butoxy-N,N-dimethylmethanamine (1.03 ml, 4.30 mmol) was added then the reaction was heated at 110° C. for 1 h then allowed to cool to RT. The reaction mixture was diluted with EtOAc (20 ml) then washed with water (2×20 ml), saturated aq. NaHCO$_3$ solution (2×20 ml) and brine (10 ml), then dried over Na$_2$SO$_4$, filtered and evaporated to afford an orange solid (510 mg). The crude material was purified by flash column chromatography on a silica column (25 g). The column was eluted with EtOAc:heptane, increasing the gradient linearly from 0:100 to 50:50 over 10 column volumes. The desired fractions were combined and evaporated to yield the product as a white solid (320 mg, 72%).

$^1$H NMR (500 MHz, DMSO-d$_6$) δ 8.07 (s, 1H), 7.98 (t, J=5.8 Hz, 1H), 7.77 (dd, J=8.4, 1.3 Hz, 1H), 7.64 (d, J=8.4 Hz, 1H), 7.41-7.12 (m, 5H), 5.07 (s, 2H), 4.55 (d, J=5.9 Hz, 2H), 4.38-4.24 (m, 2H), 1.58 (s, 9H), 1.29 (t, J=7.1 Hz, 3H).

LC/MS (System A): m/z (ESI$^+$)=410 [MH$^+$], R$_t$=1.17 min, UV purity=99%.

Synthesis of 2-({[(benzyloxy)carbonyl]amino}methyl)-6-[(tert-butoxy)carbonyl]-1,3-diethyl-1H-1,3-benzodiazol-3-ium iodide: Intermediate 41

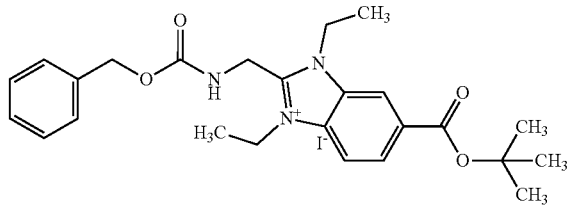 [SMILES: CCn1c(CNC(=O)OCc2ccccc2)[n+](CC)c2ccc(C(=O)OC(C)(C)C)cc21 ; [I-]]

Iodoethane (251 μl, 3.13 mmol) was added to a suspension of tert-butyl 2-({[(benzyloxy)carbonyl]amino}methyl)-1-ethyl-1H-1,3-benzodiazole-6-carboxylate, Intermediate 40 (320 mg, 0.78 mmol) in anhydrous MeCN (4 ml). The reaction mixture was heated at 120° C. for 2 h under microwave irradiation. Iodoethane (63 μl, 0.78 mmol) was added then the reaction mixture was heated at 120° C. for 2 h under microwave irradiation. The reaction was evaporated to afford the product as an orange foam (420 mg, 90%).

¹H NMR (500 MHz, DMSO-d₆) δ 8.54 (s, 1H), 8.46-8.35 (m, 1H), 8.18 (s, 2H), 7.41-7.29 (m, 5H), 5.06 (s, 2H), 4.94-4.85 (m, 2H), 4.78-4.58 (m, 4H), 1.61 (s, 9H), 1.47-1.36 (m, 6H).

LC/MS (System A): m/z (ESI⁺)=438 [M⁻], R$_t$=0.99 min, UV purity=95%.

Synthesis of 2-(aminomethyl)-6-carboxy-1,3-diethyl-1H-1,3-benzodiazol-3-ium hydrobromide bromide: Intermediate 42

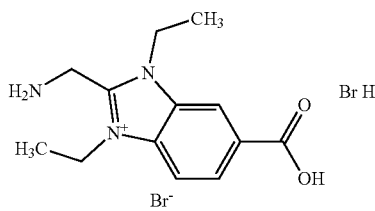

HBr solution in AcOH (33 wt %, 0.9 ml) was added to a solution of 2-({[(benzyloxy)carbonyl]amino}methyl)-6-[(tert-butoxy)carbonyl]-1,3-diethyl-1H-1,3-benzodiazol-3-ium iodide, Intermediate 41 (220 mg, 0.39 mmol) in AcOH (0.5 ml). The reaction was stirred at RT for 40 min. The reaction was concentrated in vacuo then azeotroped with MeCN (×4). The residue was suspended in the minimum volume of MeCN. The solid was collected by filtration then dried under vacuum to afford the product as an off-white solid (144 mg, 90%).

¹H NMR (500 MHz, DMSO-d₆) δ 9.30-8.35 (m, 3H), 8.30-8.22 (m, 2H), 4.83 (s, 2H), 4.82-4.68 (m, 4H), 1.51-1.43 (m, 6H).

LC/MS (System A): m/z (ESI⁺)=248 [M⁺], R$_t$=0.15 min, ELS purity=100%.

Synthesis of 3-benzyl-2-({[(tert-butoxy)carbonyl]amino}methyl)-1-ethyl-6-(trifluoromethyl)-1H-1,3-benzodiazol-3-ium bromide: Intermediate 43

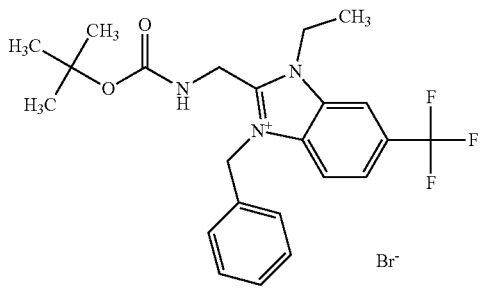 [SMILES: CCn1c(CNC(=O)OC(C)(C)C)[n+](Cc2ccccc2)c2ccc(C(F)(F)F)cc21 ; [Br-]]

Benzyl bromide (173 μl, 1.46 mmol) was added to a suspension of tert-butyl N-{[1-ethyl-6-(trifluoromethyl)-1H-1,3-benzodiazol-2-yl]methyl}carbamate, Intermediate 27 (250 mg, 0.73 mmol) in anhydrous MeCN (3 ml) in a pressure tube. The tube was sealed and heated at 80° C. for 16 h then concentrated in vacuo to afford an orange oil which solidified on standing. The resulting solid was suspended in MeCN (2 ml). The solid was collected by filtration then dried under vacuum to afford the product as a white solid (160 mg). The filtrate was concentrated in vacuo. The residue was suspended in the minimum volume of MeCN then filtered. The solid thus obtained was dried under vacuum to yield a second batch of product as an off-white solid (90 mg). The 2 batches of product were combined in MeCN then evaporated to afford the product as an off-white solid (250 mg, 64%).

¹H NMR (500 MHz, DMSO-d₆) δ 8.69 (s, 1H), 8.03-7.87 (m, 3H), 7.43-7.36 (m, 3H), 7.31-7.23 (m, 2H), 5.92 (s, 2H), 4.97-4.85 (m, 2H), 4.78 (q, J=7.1 Hz, 2H), 1.49 (t, J=7.1 Hz, 3H), 1.30 (s, 9H).

LC/MS (System A): m/z (ESI⁺)=434 [M⁺], R$_t$=1.05 min, UV purity=96%.

Synthesis of 2-(aminomethyl)-3-benzyl-1-ethyl-6-(trifluoromethyl)-1H-1,3-benzodiazol-3-iumhydrochloride bromide: Intermediate 44

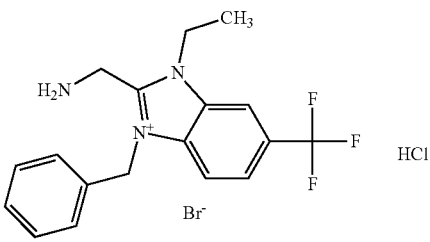 [SMILES: CCn1c(CN)[n+](Cc2ccccc2)c2ccc(C(F)(F)F)cc21 ; [Br-] ; Cl]

HCl solution in dioxane (4.0 M, 0.61 ml, 2.4 mmol) was added to a solution of 3-benzyl-2-({[(tert-butoxy)carbonyl]amino}methyl)-1-ethyl-6-(trifluoromethyl)-1H-1,3-benzodiazol-3-ium bromide, Intermediate 43 (250 mg, 0.49 mmol) in MeCN (2.5 ml). The reaction was stirred at RT for 18 h then concentrated in vacuo. The residue was azeotroped with MeCN then dried under vacuum to afford the product as a pale yellow solid (209 mg, 95%).

¹H NMR (500 MHz, DMSO-d₆) δ 9.18 (s, 3H), 8.77 (s, 1H), 8.10-7.99 (m, 2H), 7.51-7.46 (m, 2H), 7.44-7.34 (m, 3H), 6.05 (s, 2H), 4.94-4.79 (m, 4H), 1.53 (t, J=7.2 Hz, 3H).

LC/MS (System A): m/z (ESI⁺)=334 [M⁺], R$_t$=0.86 min, UV purity=100%.

Synthesis of 2-[(6-bromo-1-ethyl-1H-1,3-benzodiazol-2-yl)methyl]-2,3-dihydro-1H-isoindole-1,3-dione: Intermediate 45

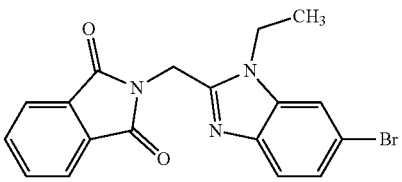 [SMILES: CCn1c(CN2C(=O)c3ccccc3C2=O)nc2ccc(Br)cc21]

A mixture of N-phthaloylglycine (13.1 g, 63.8 mmol), TBTU (21.5 g, 67.0 mmol) and NEt₃ (14.1 ml, 79.1 mmol) in anhydrous DMF (150 ml) was stirred at RT for 45 min. A solution of 5-bromo-1-N-ethylbenzene-1,2-diamine (13.1 g, 60.9 mmol) in anhydrous THF (50 ml) was added and the resulting mixture was stirred at RT for 18 h. The reaction mixture was added onto saturated aq. NaHCO₃ solution (400 ml). The resulting precipitate was collected by filtration then washed with water and dried under vacuum to afford the intermediate as a light grey solid. The solid thus obtained was added portionwise to acetic acid (150 ml). The resulting suspension was heated at 100° C. for 2.5 h then allowed to cool to RT. The reaction mixture was concentrated in vacuo then the residue was partitioned between EtOAc (300 ml) and water (300 ml). The resulting precipitate was collected by filtration and washed with EtOAc (200 ml) and water (200 ml) then dried under vacuum to afford the product as a pink solid (17.9 g, 76%).

$^1$H NMR (500 MHz, DMSO-d$_6$) δ 7.96 (dd, J=5.6, 3.0 Hz, 2H), 7.93-7.88 (m, 3H), 7.44 (d, J=8.5 Hz, 1H), 7.27 (dd, J=8.5, 1.9 Hz, 1H), 5.12 (s, 2H), 4.39 (q, J=7.2 Hz, 2H), 1.37 (t, J=7.2 Hz, 3H).

LC/MS (System A): m/z (ESI$^+$)=384 [M($^{79}$Br)H$^+$], 386 [M($^{81}$Br)H$^+$], R$_t$=1.12 min, UV purity=100%.

Synthesis of tert-butyl 4-(4-{2-[(1,3-dioxo-2,3-di-hydro-1H-isoindol-2-yl)methyl]-1-ethyl-1H-1,3-benzodiazol-6-yl}-1H-pyrazol-1-yl)piperidine-1-carboxylate: Intermediate 46

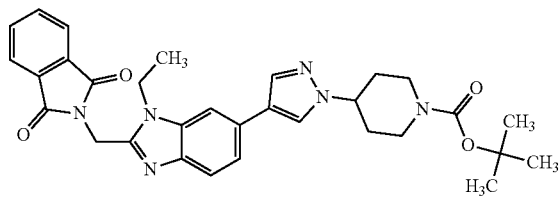 [SMILES: CCn1c(CN2C(=O)c3ccccc3C2=O)nc2ccc(-c3cnn(C4CCN(C(=O)OC(C)(C)C)CC4)c3)cc21]

tert-Butyl 4-[4-(tetramethyl-1,3,2-dioxaborolan-2-yl)-1H-pyrazol-1-yl]piperidine-1-carboxylate (540 mg, 1.43 mmol) was added to a solution of 2-[(6-bromo-1-ethyl-1H-1,3-benzodiazol-2-yl)methyl]-2,3-dihydro-1H-isoindole-1,3-dione, Intermediate 45 (500 mg, 1.30 mmol) in dioxane (10 ml) and water (0.5 ml) in a pressure tube. Cs$_2$CO$_3$ (848 mg, 2.60 mmol) was added then the resulting suspension was de-gassed by bubbling a stream of nitrogen through the reaction mixture for 10 min. XPhos-Pd-G2 (61 mg, 0.078 mmol) was added then the nitrogen bubbling was continued for a further 5 min. The tube was sealed then heated at 100° C. for 16 h. The reaction mixture was concentrated in vacuo then partitioned between EtOAc (100 ml) and water (100 ml). The phases were separated then the organic phase was washed with water (50 ml) and brine (2×50 ml), then dried over MgSO$_4$, filtered and evaporated. The crude material was purified by flash column chromatography on a silica column (50 g). The column was eluted with EtOAc:heptane, increasing the gradient linearly from 0:100 to 100:0 over 10 column volumes. The desired fractions were combined and evaporated to yield the product as a light yellow foam (226 mg, 31%).

$^1$H NMR (500 MHz, DMSO-d$_6$) δ 8.28 (s, 1H), 7.98-7.94 (m, 2H), 7.94-7.89 (m, 3H), 7.81-7.76 (m, 1H), 7.43 (d, J=8.4 Hz, 1H), 7.38 (dd, J=8.4, 1.5 Hz, 1H), 5.11 (s, 2H), 4.43-4.34 (m, 3H), 4.04 (dd, J=15.8, 8.8 Hz, 2H), 2.93 (s, 2H), 2.09-2.02 (m, 2H), 1.81 (qd, J=12.4, 4.3 Hz, 2H), 1.43 (s, 9H), 1.42-1.39 (m, 3H).

LC/MS (System A): m/z (ESI$^+$)=555 [MH$^+$], R$_t$=1.13 min, UV purity=100%.

Synthesis of 6-(1-{1-[(tert-butoxy)carbonyl]piperi-din-4-yl}-1H-pyrazol-4-yl)-2-[(1,3-dioxo-2,3-di-hydro-1H-isoindol-2-yl)methyl]-1,3-diethyl-1H-1,3-benzodiazol-3-ium iodide: Intermediate 47

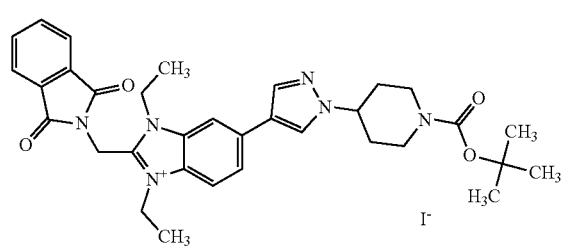 [SMILES: CCn1c(CN2C(=O)c3ccccc3C2=O)[n+](CC)c2ccc(-c3cnn(C4CCN(C(=O)OC(C)(C)C)CC4)c3)cc21 ; [I-]]

Iodoethane (159 μl, 1.98 mmol) was added to a solution of tert-butyl 4-(4-{2-[(1,3-dioxo-2,3-dihydro-1H-isoindol-2-yl)methyl]-1-ethyl-1H-1,3-benzodiazol-6-yl}-1H-pyrazol-1-yl)piperidine-1-carboxylate, Intermediate 46 (220 mg, 0.397 mmol) in anhydrous MeCN (5 ml). The reaction mixture was heated under microwave irradiation for 2 h at 120° C. Iodoethane (130 μl, 1.62 mmol) was added then the reaction mixture was heated under microwave irradiation for 1 h at 120° C. The reaction mixture was concentrated in vacuo then azeotroped with diethyl ether. The residue was dried under vacuum to afford the product as a light yellow solid (280 mg, 80%).

$^1$H NMR (500 MHz, DMSO-d$_6$) δ 8.50 (s, 1H), 8.29 (s, 1H), 8.12 (s, 1H), 8.10 (d, J=8.8 Hz, 1H), 7.98-7.94 (m, 3H), 7.94-7.89 (m, 2H), 5.42 (s, 2H), 4.74-4.65 (m, 4H), 4.48-4.35 (m, 1H), 4.06 (d, 2H), 2.95 (br. s, 2H), 2.08 (d, J=6.7 Hz, 2H), 1.81 (qd, J=12.7, 4.7 Hz, 2H), 1.49-1.40 (m, 15H).

LC/MS (System A): m/z (ESI$^+$)=583 [M$^+$], R$_t$=1.13 min, UV purity=81%.

Synthesis of 2-(aminomethyl)-6-(1-{1-[(tert-butoxy)carbonyl]piperidin-4-yl}-1H-pyrazol-4-yl)-1,3-di-ethyl-1H-1,3-benzodiazol-3-ium iodide: Intermediate 48

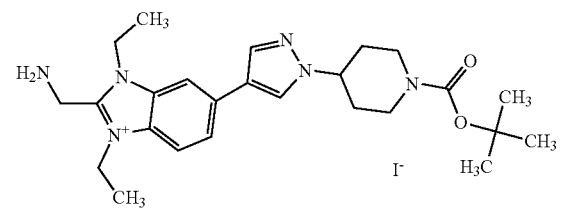 [SMILES: CCn1c(CN)[n+](CC)c2ccc(-c3cnn(C4CCN(C(=O)OC(C)(C)C)CC4)c3)cc21 ; [I-]]

Hydrazine hydrate (96 µl, 2.0 mmol) was added to a solution of 6-(1-{1-[(tert-butoxy)carbonyl]piperidin-4-yl}-1H-pyrazol-4-yl)-2-[(1,3-dioxo-2,3-dihydro-1H-isoindol-2-yl)methyl]-1,3-diethyl-1H-1,3-benzodiazol-3-ium iodide, Intermediate 47 (280 mg, 0.39 mmol) in methanol (5 ml) in a pressure tube. The tube was sealed then heated at 75° C. for 1 h. The reaction mixture was allowed to cool to RT then concentrated in vacuo. The residue was suspended in CH$_2$Cl$_2$ (9:1, 20 ml) then filtered. The solid thus obtained was washed further CH$_2$Cl$_2$ (20 ml). The filtrates were combined and evaporated to dryness to afford the product as a light yellow solid (225 mg, 82%).

$^1$H NMR (500 MHz, DMSO-d$_6$) δ 8.48 (s, 1H), 8.23 (s, 1H), 8.10 (s, 1H), 8.03 (d, J=8.7 Hz, 1H), 7.90 (dd, J=8.7, 1.3 Hz, 1H), 4.62-4.56 (m, 4H), 4.44-4.36 (m, 1H), 4.28 (s, 2H), 4.07 (d, J=10.4 Hz, 2H), 2.94 (br. s, 2H), 2.08 (d, J=10.4 Hz, 2H), 1.82 (tt, J=12.2, 6.2 Hz, 2H), 1.50-1.40 (m, 15H).

LC/MS (System A): m/z (ESI$^+$)=453 [M$^+$], R$_t$=0.91 min, UV purity=83%.

Synthesis of 6-(2-{[(tert-butoxy)carbonyl]amino}ethoxy)-1,3-diethyl-2-[({[(9H-fluoren-9-yl)methoxy]carbonyl}amino)methyl]-1H-1,3-benzodiazol-3-ium iodide Intermediate 49

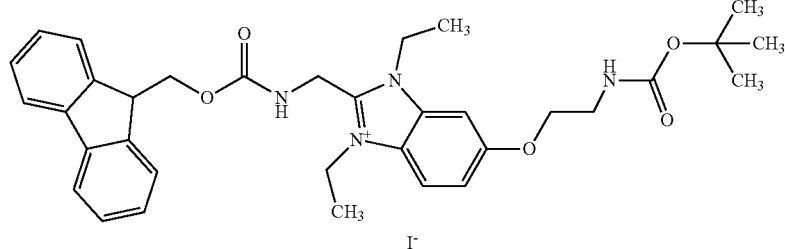 [SMILES: CCn1c(CNC(=O)OCC2c3ccccc3-c3ccccc32)[n+](CC)c2ccc(OCCNC(=O)OC(C)(C)C)cc21 ; [I-]]

Intermediate 49 was synthesised by according to literature procedures (US 2015/0018313 A1).

Synthesis of 2-(aminomethyl)-6-(2-{[(tert-butoxy)carbonyl]amino}ethoxy)-1,3-diethyl-1H-1,3-benzodiazol-3-ium iodide: Intermediate 50

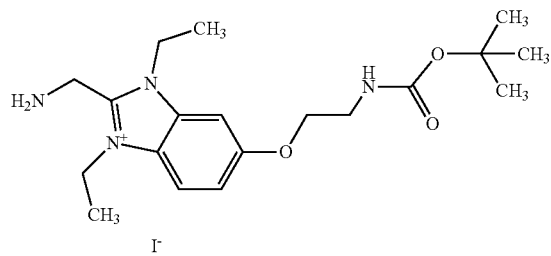 [SMILES: CCn1c(CN)[n+](CC)c2ccc(OCCNC(=O)OC(C)(C)C)cc21 ; [I-]]

Morpholine (3.46 ml, 40.0 mmol) was added to a solution of 6-(2-{[(tert-butoxy)carbonyl]amino}ethoxy)-1,3-diethyl-2-[({[(9H-fluoren-9-yl)methoxy]carbonyl}amino)methyl]-1H-1,3-benzodiazol-3-ium iodide, Intermediate 49 (95%, 3.00 g, 4.00 mmol) in THF (50 ml). The reaction mixture was stirred at RT for 25 min then diluted with diethyl ether (150 ml). The resulting mixture was agitated then the supernatant was decanted off. The residual gum was washed further with ether (2×60 ml) then dried under vacuum. The residue was dissolved in THF then concentrated in vacuo afford the product as a pale orange solid (1.99 g, 83%).

$^1$H NMR (500 MHz, DMSO-d$_6$) δ 7.95 (d, J=9.1 Hz, 1H), 7.65-7.61 (m, 1H), 7.25 (dd, J=9.1, 2.3 Hz, 1H), 7.11-7.05 (m, 1H), 4.61-4.53 (m, 4H), 4.25 (s, 2H), 4.11 (t, J=5.9 Hz, 2H), 3.36 (q, J=5.9 Hz, 2H), 1.45-1.41 (m, 6H), 1.39 (s, 9H).

LC/MS (System A): m/z (ESI$^+$)=363 [M$^+$], R$_t$=0.76 min, UV purity=82%.

B. Synthesis of Example Compounds

Example 1—Synthesis of 2-{[(3-amino-6-bromopyrazin-2-yl)formamido]methyl}-1-ethyl-6-methoxy-3-methyl-1H-1,3-benzodiazol-3-ium iodide

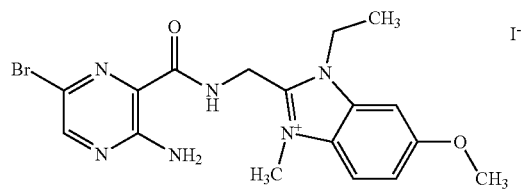

DIPEA (500 µl, 2.86 mmol) was added to a solution of lithium 3-amino-6-bromopyrazine-2-carboxylate, Intermediate 1 (160 mg, 0.714 mmol), 2-(aminomethyl)-1-ethyl-6-methoxy-3-methyl-1H-1,3-benzodiazol-3-ium iodide, Intermediate 13 (248 mg, 0.714 mmol) and HBTU (352 mg, 0.929 mmol) in anhydrous DMF (8 ml). The resulting mixture was stirred at ambient temperature for 1.5 h. The reaction mixture was diluted with water (40 ml), stirred for 0.5 h then left to stand at RT overnight. The resulting brown/orange precipitate was filtered, washed with water (20 ml), dissolved in the minimum of water/MeCN and then lyophilised. The resulting solid was suspended in TBME (8 ml), sonicated, collected by filtration and dried under vacuum. The resulting solid was dissolved in EtOAc (40 ml) then washed with water (30 ml) then brine (30 ml). The organic phase was dried over MgSO$_4$, filtered and concentrated under reduced pressure to afford a glassy oil that gave a solid upon scratching. The resulting solid was dissolved in the minimum of water/MeCN then lyophilised to yield the product as a yellow solid (275 mg, 70%).

$^1$H NMR (500 MHz, DMSO-d$_6$) δ 9.53 (t, J=5.3 Hz, 1H), 8.41 (s, 1H), 7.93 (d, J=9.1 Hz, 1H), 7.66 (s, 2H), 7.57 (d, J=2.3 Hz, 1H), 7.29 (dd, J=9.1, 2.3 Hz, 1H), 5.00 (d, J=5.4 Hz, 2H), 4.62 (q, J=7.2 Hz, 2H), 4.09 (s, 3H), 3.91 (s, 3H), 1.38 (t, J=7.2 Hz, 3H). LC/MS (System C): m/z (ESI$^+$)=419 [M($^{79}$Br)$^+$], 421 [M($^{81}$Br)$^+$]), R$_t$=1.90 min, UV purity=100%.

Example 2—Synthesis of 2-{[(3-amino-6-bromopyrazin-2-yl)formamido]methyl}-1,3-diethyl-6-methoxy-1H-1,3-benzodiazol-3-ium formate

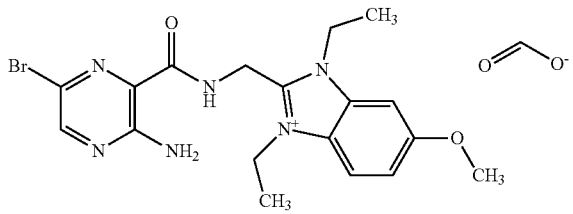

A solution of 5-bromo-3-(1H-imidazole-1-carbonyl)pyrazin-2-amine, Intermediate 2 (80 mg, 0.30 mmol) and 2-(aminomethyl)-1,3-diethyl-6-methoxy-1H-1,3-benzodiazol-3-ium iodide, Intermediate 15 (108 mg, 0.30 mmol) in DMF (0.7 ml) was stirred at RT for 16 h. The reaction mixture was transferred onto a C18 Samplet® and dried under vacuum. The crude material was purified by flash column chromatography on C18 (12 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and lyophilised to yield the product as a pale yellow solid (54 mg, 37%).

$^1$H NMR (500 MHz, DMSO-d$_6$) δ 9.62 (s, 1H), 8.43 (s, 1H), 8.41 (s, 1H), 7.96 (d, J=9.1 Hz, 1H), 7.66 (s, 2H), 7.59 (d, J=2.3 Hz, 1H), 7.28 (dd, J=9.1, 2.3 Hz, 1H), 5.04 (d, J=5.3 Hz, 2H), 4.66-4.58 (m, 4H), 3.91 (s, 3H), 1.43-1.36 (m, 6H).

LC/MS (System C): m/z (ESI$^+$)=433 [M($^{79}$Br)$^+$], 435 [M($^{81}$Br)$^+$]), R$_t$=1.91 min, UV purity=98%.

Example 3—Synthesis of 2-{[(3-amino-6-bromopyrazin-2-yl)formamido]methyl}-1-ethyl-3-(2-hydroxyethyl)-6-methoxy-1H-1,3-benzodiazol-3-ium formate

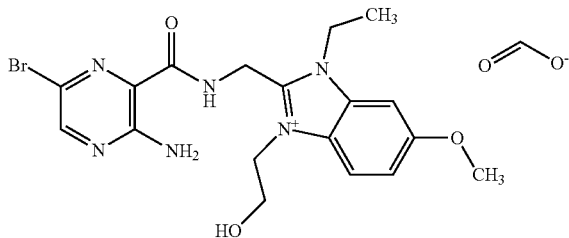

A mixture of 2-(aminomethyl)-1-ethyl-3-(2-hydroxyethyl)-6-methoxy-1H-1,3-benzodiazol-3-ium chloride hydrochloride, Intermediate 18 (80%, 125 mg, 0.31 mmol) and 5-bromo-3-(1H-imidazole-1-carbonyl)pyrazin-2-amine, Intermediate 2 (83 mg, 0.31 mmol) in DMF (2 ml) was stirred at RT for 0.5 h. The reaction mixture was concentrated in vacuo to afford a red oil. The crude material was purified by flash column chromatography on C18 (12 g). The column was eluted with MeCN:H$_2$O+0.1% formic acid using the following gradient (% MeCN, column volumes): 10%, 2 CV; 10-30%, 15 CV; 30-100%, 3 CV; 100%, 3 CV. The desired fractions were combined and evaporated. The material thus obtained was further purified by flash column chromatography on C18 (12 g). The column was eluted with MeCN:H$_2$O+0.1% formic acid using the following gradient (% MeCN, column volumes): 10%, 2 CV; 10-46%, 18 CV. The desired fractions were combined and evaporated to yield the product as a pale orange solid (11 mg, 7%).

$^1$H NMR (500 MHz, DMSO-d$_6$) δ 9.58 (t, J=5.2 Hz, 1H), 8.44 (s, 1H), 8.41 (s, 1H), 7.98 (d, J=9.1 Hz, 1H), 7.68 (s, 2H), 7.57 (d, J=2.2 Hz, 1H), 7.28 (dd, J=9.1, 2.3 Hz, 1H), 5.07 (d, J=5.2 Hz, 2H), 4.76 (t, J=4.8 Hz, 2H), 4.63 (q, J=7.1 Hz, 2H), 3.92 (s, 3H), 3.79 (t, J=4.9 Hz, 2H), 1.39 (t, J=7.2 Hz, 3H).

LC/MS (System C): m/z (ESI$^+$)=449 [M($^{79}$Br)$^+$], 451 [M($^{81}$Br)$^+$]), R$_t$=1.73 min, UV purity=97%.

Example 4—Synthesis of 2-{[(3-amino-6-bromopyrazin-2-yl)formamido]methyl}-1-ethyl-3-{2-[2-(2-hydroxyethoxy)ethoxy]ethyl}-6-methoxy-1H-1,3-benzodiazol-3-ium formate

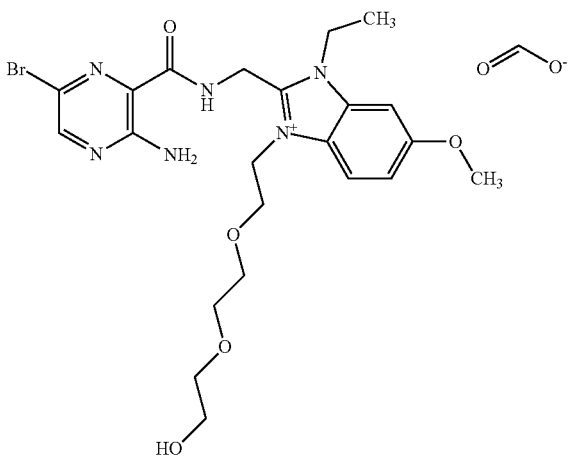

DIPEA (156 μl, 0.893 mmol) was added to a solution of lithium 3-amino-6-bromopyrazine-2-carboxylate, Intermediate 1 (50 mg, 0.22 mmol), 2-(aminomethyl)-1-ethyl-3-{2-[2-(2-hydroxyethoxy)ethoxy]ethyl}-6-methoxy-1H-1,3-benzodiazol-3-ium iodide, Intermediate 20 (104 mg, 0.22 mmol) and HBTU (110 mg, 0.29 mmol) in DMF (1 ml). The resulting mixture was stirred at ambient temperature for 2.5 h. The reaction was concentrated under a flow of nitrogen to afford the crude product as an oil. The crude material was purified by flash column chromatography on C18 (12 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and lyophilised to yield the product as a brown solid (25 mg). The material thus obtained was further purified by flash column chromatography on C18 (12 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and lyophilised to yield the product as a light brown solid (16 mg, 12%).

$^1$H NMR (500 MHz, DMSO-d$_6$) δ 9.48 (t, J=5.4 Hz, 1H), 8.41 (s, 1H), 7.97 (d, J=9.2 Hz, 1H), 7.67 (s, 2H), 7.57 (d, J=2.3 Hz, 1H), 7.29 (dd, J=9.2, 2.3 Hz, 1H), 5.05 (d, J=5.5 Hz, 2H), 4.85 (t, J=4.9 Hz, 2H), 4.63 (q, J=7.1 Hz, 2H), 4.51 (t, J=5.4 Hz, 1H), 3.91 (s, 3H), 3.81 (t, J=4.9 Hz, 2H), 3.51-3.45 (m, 2H), 3.44-3.35 (m, 4H), 3.30-3.28 (m, 2H), 1.38 (t, J=7.2 Hz, 3H).

LC/MS (System C): m/z (ESI$^+$)=537 [M($^{79}$Br)$^+$], 539 [M($^{81}$Br)$^+$]), R$_t$=1.89 min, UV purity=97%.

Example 5—Synthesis of 2-{[(3-amino-6-chloropyrazin-2-yl)formamido]methyl}-1-ethyl-6-methoxy-3-methyl-1H-1,3-benzodiazol-3-ium iodide

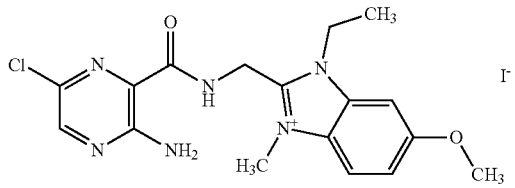 [SMILES: CCn1c(CNC(=O)c2nc(Cl)cnc2N)[n+](C)c2ccc(OC)cc21 ; [I-]]

DIPEA (200 μl, 1.15 mmol) was added to a solution of 3-amino-6-chloropyrazine-2-carboxylic acid (50 mg, 0.29 mmol), 2-(aminomethyl)-1-ethyl-6-methoxy-3-methyl-1H-1,3-benzodiazol-3-ium iodide, Intermediate 13 (100 mg, 0.29 mmol) and HBTU (142 mg, 0.37 mmol) in anhydrous DMF (1 ml). The resulting mixture was stirred at ambient temperature for 18 h. The reaction mixture was concentrated under a flow of nitrogen to afford the crude product as an oil. The crude material was purified by flash column chromatography on C18 (12 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and lyophilised to yield the product as an off-white solid (84 mg, 58%).

$^1$H NMR (250 MHz, DMSO-d$_6$) δ 9.57 (t, J=5.3 Hz, 1H), 8.38 (s, 1H), 7.93 (d, J=9.1 Hz, 1H), 7.66 (s, 2H), 7.57 (d, J=2.2 Hz, 1H), 7.29 (dd, J=9.1, 2.3 Hz, 1H), 4.99 (d, J=5.3 Hz, 2H), 4.62 (q, J=7.0 Hz, 2H), 4.09 (s, 3H), 3.91 (s, 3H), 1.38 (t, J=7.1 Hz, 3H).

LC/MS (System C): m/z (ESI$^+$)=375 [M($^{35}$Cl)$^+$], 377 [M($^{37}$Cl)$^+$]), R$_t$=1.83 min, UV purity=100%.

Example 6—Synthesis of 2-{[(3-amino-6-iodopyrazin-2-yl)formamido]methyl}-1-ethyl-6-methoxy-3-methyl-1H-1,3-benzodiazol-3-ium iodide

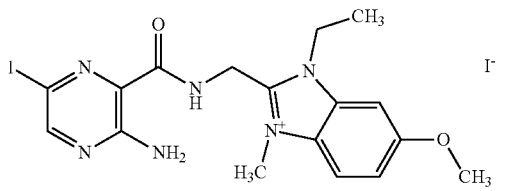

DIPEA (129 μl, 0.74 mmol) was added to a solution of lithium 3-amino-6-iodopyrazine-2-carboxylate, Intermediate 3 (50 mg, 0.19 mmol), 2-(aminomethyl)-1-ethyl-6-methoxy-3-methyl-1H-1,3-benzodiazol-3-ium iodide, Intermediate 13 (64 mg, 0.19 mmol) and HBTU (91 mg, 0.24 mmol) in anhydrous DMF (1 ml). The resulting mixture was stirred at ambient temperature for 2 h. Water (7 ml) was added and the resulting mixture was stirred at RT for 1 h. The reaction suspension was filtered and the solid was washed with water then dried under vacuum. The solid was suspended in TBME (5 ml) with sonication then the resulting suspension was filtered and the solid thus obtained was dried under vacuum. The solid was dissolved in EtOAc (30 ml) then extracted with water (30 ml) and brine (30 ml). The organic phase was dried over MgSO$_4$, then filtered and concentrated in vacuo. The residue thus obtained was dried under vacuum to yield the product as a yellow solid (59 mg, 52%).

$^1$H NMR (500 MHz, DMSO-d$_6$) δ 9.47 (t, J=5.4 Hz, 1H), 8.47 (s, 1H), 7.93 (d, J=9.1 Hz, 1H), 7.63-7.52 (m, 3H), 7.29 (dd, J=9.1, 2.3 Hz, 1H), 5.00 (d, J=5.4 Hz, 2H), 4.61 (q, J=7.1 Hz, 2H), 4.08 (s, 3H), 3.91 (s, 3H), 1.38 (t, J=7.2 Hz, 3H).

LC/MS (System C): m/z (ESI$^+$)=467 [M$^+$]), R$_t$=2.00 min, UV purity=96%.

Example 7—Synthesis of 2-{[(3-amino-6-methylpyrazin-2-yl)formamido]methyl}-1-ethyl-6-methoxy-3-methyl-1H-1,3-benzodiazol-3-ium iodide

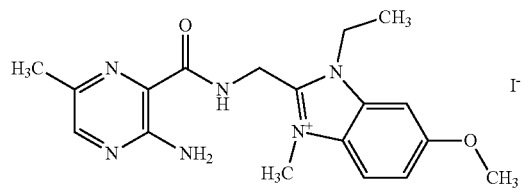

HBTU (155 mg, 0.41 mmol) was added to a solution of lithium 3-amino-6-methylpyrazine-2-carboxylate, Intermediate 5 (50 mg, 0.31 mmol) and 2-(aminomethyl)-1-ethyl-6-methoxy-3-methyl-1H-1,3-benzodiazol-3-ium iodide, Intermediate 13 (109 mg, 0.31 mmol) in anhydrous DMF (1 ml). DIPEA (218 μl, 1.26 mmol) was added then the resulting mixture was stirred at ambient temperature for 3 h. The reaction was concentrated under a flow of nitrogen to afford the crude product as an oil. The crude material was purified by flash column chromatography on C18 (12 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and lyophilised to yield the product as an off-white solid (67 mg, 41%).

$^1$H NMR (500 MHz, DMSO-d$_6$) δ9.54 (t, J=5.4 Hz, 1H), 8.18 (s, 1H), 7.92 (d, J=9.1 Hz, 1H), 7.56 (d, J=2.3 Hz, 1H), 7.29 (dd, J=9.1, 2.3 Hz, 1H), 7.23 (s, 2H), 5.00 (d, J=5.4 Hz, 2H), 4.62 (q, J=7.2 Hz, 2H), 4.10 (s, 3H), 3.91 (s, 3H), 2.37 (s, 3H), 1.37 (t, J=7.2 Hz, 3H).

LC/MS (System C): m/z (ESI$^+$)=355 [M$^+$]), R$_t$=1.64 min, UV purity=93%.

Example 8—Synthesis of 2-{[(3-amino-6-ethylpyrazin-2-yl)formamido]methyl}-1-ethyl-6-methoxy-3-methyl-1H-1,3-benzodiazol-3-ium iodide

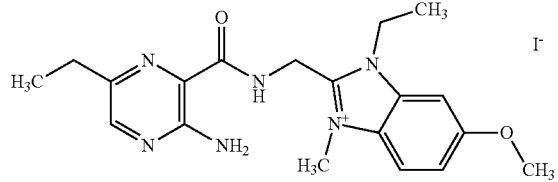 [SMILES: CCc1cnc(N)c(C(=O)NCc2n(CC)c3cc(OC)ccc3[n+]2C)n1 ; [I-]]

HBTU (142 mg, 0.38 mmol) was added to a solution of lithium 3-amino-6-ethylpyrazine-2-carboxylate, Intermediate 7 (50 mg, 0.29 mmol) and 2-(aminomethyl)-1-ethyl-6-methoxy-3-methyl-1H-1,3-benzodiazol-3-ium iodide, Intermediate 13 (100 mg, 0.29 mmol) in anhydrous DMF (1 ml). DIPEA (200 μl, 1.16 mmol) was added then the resulting mixture was stirred at ambient temperature for 5 h. The reaction mixture was concentrated under a flow of nitrogen to afford the crude product as an oil. The crude material was purified by flash column chromatography on C18 (12 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and lyophilised to yield the product as an off-white solid (28 mg, 19%).

$^1$H NMR (500 MHz, DMSO-d$_6$) δ 9.51 (t, J=5.4 Hz, 1H), 8.20 (s, 1H), 7.93 (d, J=9.1 Hz, 1H), 7.56 (d, J=2.3 Hz, 1H), 7.29 (dd, J=9.1, 2.3 Hz, 1H), 7.24 (s, 2H), 5.02 (d, J=5.5 Hz, 2H), 4.63 (q, J=7.1 Hz, 2H), 4.11 (s, 3H), 3.91 (s, 3H), 2.67 (q, J=7.6 Hz, 2H), 1.37 (t, J=7.2 Hz, 3H), 1.23 (t, J=7.6 Hz, 3H).

LC/MS (System C): m/z (ESI$^+$)=369 [M$^+$]), R$_t$=1.89 min, UV purity=98%.

Example 9—Synthesis of 2-({[3-amino-6-(methylsulfanyl)pyrazin-2-yl]formamido}methyl)-1-ethyl-6-methoxy-3-methyl-1H-1,3-benzodiazol-3-ium iodide

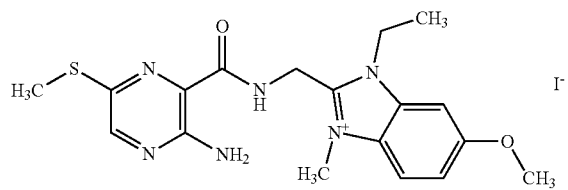

HBTU (106 mg, 0.28 mmol) was added to a solution of 3-amino-6-(methylsulfanyl)pyrazine-2-carboxylic acid, Intermediate 8 (40 mg, 0.22 mmol) and 2-(aminomethyl)-1-ethyl-6-methoxy-3-methyl-1H-1,3-benzodiazol-3-ium iodide, Intermediate 13 (75 mg, 0.22 mmol) in anhydrous DMF (1 ml). DIPEA (151 μl, 0.86 mmol) was added then the resulting mixture was stirred at ambient temperature for 1.5 h. The reaction mixture was concentrated under a flow of nitrogen to afford the crude product as an oil. The crude material was purified by flash column chromatography on C18 (12 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and lyophilised to yield the product as an off-white solid (31 mg, 27%).

$^1$H NMR (500 MHz, DMSO-d$_6$) δ 9.40 (t, J=5.4 Hz, 1H), 8.27 (s, 1H), 7.93 (d, J=9.1 Hz, 1H), 7.57 (d, J=2.3 Hz, 1H), 7.32 (s, 2H), 7.29 (dd, J=9.1, 2.3 Hz, 1H), 5.02 (d, J=5.4 Hz, 2H), 4.64 (q, J=7.1 Hz, 2H), 4.12 (s, 3H), 3.91 (s, 3H), 2.58 (s, 3H), 1.38 (t, J=7.2 Hz, 3H).

LC/MS (System C): m/z (ESI$^+$)=387 [M$^+$]), R$_t$=1.93 min, UV purity=98%.

Example 10—System C Synthesis of 2-{[(3-aminopyrazin-2-yl)formamido]methyl}-1-ethyl-6-methoxy-3-methyl-1H-1,3-benzodiazol-3-ium iodide

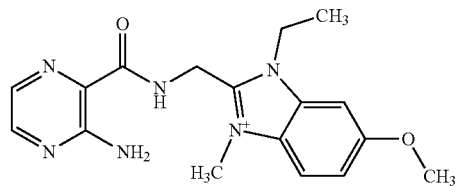

DIPEA (200 μl, 1.15 mmol) was added to a solution of 3-aminopyrazine-2-carboxylic acid (40 mg, 0.29 mmol), 2-(aminomethyl)-1-ethyl-6-methoxy-3-methyl-1H-1,3-benzodiazol-3-ium iodide, Intermediate 13 (100 mg, 0.29 mmol) and HBTU (142 mg, 0.37 mmol) in anhydrous DMF (1 ml). The resulting mixture was stirred at ambient temperature for 2.5 h. The reaction mixture was concentrated under a flow of nitrogen to afford the crude product as an oil. The crude material was purified by flash column chromatography on C18 (12 g). The column was eluted with MeCN:H$_2$O+0.1% formic acid using the following gradient (% MeCN, column volumes): 10%, 2 CV; 10-100%, 20 CV; 100%, 2 CV. The desired fractions were combined and lyophilised to yield the product as a white solid (95 mg, 69%).

$^1$H NMR (500 MHz, DMSO-d$_6$) δ 9.75 (t, J=5.4 Hz, 1H), 8.27 (d, J=2.3 Hz, 1H), 7.92 (d, J=9.1 Hz, 1H), 7.87 (d, J=2.3 Hz, 1H), 7.56 (d, J=2.3 Hz, 1H), 7.47 (s, 2H), 7.29 (dd, J=9.1, 2.3 Hz, 1H), 4.99 (d, J=5.4 Hz, 2H), 4.63 (q, J=7.2 Hz, 2H), 4.10 (s, 3H), 3.91 (s, 3H), 1.37 (t, J=7.2 Hz, 3H).

LC/MS (System C): m/z (ESI$^+$)=341 [M$^+$]), R$_t$=1.46 min, UV purity=98%.

Example 11—Synthesis of 2-{[(3-amino-6-bromopyrazin-2-yl)formamido]methyl}-6-chloro-1-ethyl-3-methyl-1H-1,3-benzodiazol-3-ium formic acid formate

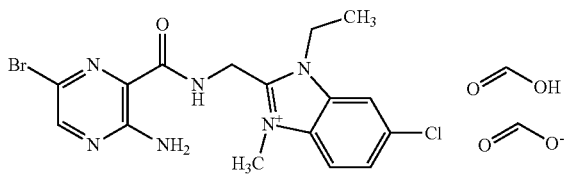

A suspension of lithium 3-amino-6-bromopyrazine-2-carboxylate, Intermediate 1 (70 mg, 0.31 mmol), 2-(aminomethyl)-6-chloro-1-ethyl-3-methyl-1H-1,3-benzodiazol-3-ium iodide, Intermediate 23 (0.11 g, 0.31 mmol), EDC.HCl (0.12 g, 0.63 mmol) and HOAt (0.04 g, 0.31 mmol) in anhydrous DMF (2 ml) was stirred at RT for 16 h. The reaction was evaporated then the crude material was purified by flash column chromatography on C18 (12 g). The column was eluted with MeCN:H$_2$O+0.1% formic acid using the following gradient (% MeCN, column volumes): 5%, 5 CV; 5-100%, 20 CV; 100%, 2 CV. The desired fractions were combined and evaporated to yield the product as an orange solid (70 mg, 43%).

$^1$H NMR (500 MHz, DMSO-d$_6$) δ 9.56 (t, J=5.3 Hz, 1H), 8.41 (s, 1H), 8.36 (s, 2H), 8.34 (d, J=1.8 Hz, 1H), 8.10-8.07

(m, 1H), 7.78-7.75 (m, 1H), 7.65 (s, 2H), 5.03 (d, J=5.3 Hz, 2H), 4.65 (q, J=7.2 Hz, 2H), 4.12 (s, 3H), 1.38 (t, J=7.2 Hz, 3H).

LC/MS (System C): m/z (ESI$^+$)=423 [M($^{79}$Br$^{35}$Cl)$^+$], 425 [M($^{79}$Br$^{37}$Cl+$^{81}$Br$^{35}$Cl)$^+$]), 427 [M($^{81}$Br $^{37}$Cl)$^+$] R$_t$=1.93 min, UV purity=99%.

Example 12—Synthesis of 2-{[(3-amino-6-bromopyrazin-2-yl)formamido]methyl}-1-ethyl-6-fluoro-3-methyl-1H-1,3-benzodiazol-3-ium formate

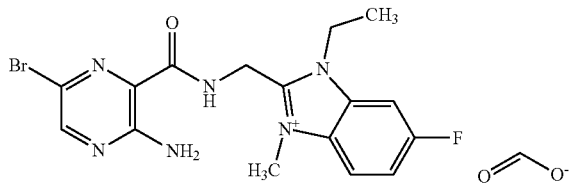

A solution of 2-(aminomethyl)-1-ethyl-6-fluoro-3-methyl-1H-1,3-benzodiazol-3-ium hydrochloride iodide, Intermediate 26 (83 mg, 0.22 mmol) and DIPEA (39 µl, 0.22 mmol) in anhydrous DMF (1 ml) were added to a solution of lithium 3-amino-6-bromopyrazine-2-carboxylate, Intermediate 1 (50 mg, 0.22 mmol), EDC.HCl (86 mg, 0.45 mmol) and HOAt (30 mg, 0.22 mmol) in DMF (1 ml). The reaction was stirred at RT for 64 h then concentrated in vacuo. The crude material was purified by flash column chromatography on C18 (12 g). The column was eluted with MeCN:H$_2$O+0.1% formic acid using the following gradient (% MeCN, column volumes): 5%, 5 CV; 5-100%, 20 CV; 100%, 2 CV. The desired fractions were combined and evaporated to an orange solid (28 mg). The solid thus obtained was further purified by flash column chromatography on C18 (12 g). The column was eluted with MeCN:H$_2$O+0.1% formic acid using the following gradient (% MeCN, column volumes): 5%, 5 CV; 5-100%, 20 CV; 100%, 2 CV. The desired fractions were combined and evaporated to yield the product as an orange solid (20 mg, 20%).

$^1$H NMR (500 MHz, DMSO-d$_6$) δ 9.56 (t, J=5.3 Hz, 1H), 8.46-8.40 (m, 2H), 8.15-8.06 (m, 2H), 7.70-7.56 (m, 3H), 5.02 (d, J=5.3 Hz, 2H), 4.63 (q, J=7.2 Hz, 2H), 4.12 (s, 3H), 1.38 (t, J=7.2 Hz, 3H).

LC/MS (System C): m/z (ESI$^+$)=407 [M($^{79}$Br)$^+$], 409 [M($^{81}$Br)$^+$] R$_t$=1.71 min, UV purity=99%.

Example 13—Synthesis of 2-{[(3-amino-6-bromopyrazin-2-yl)formamido]methyl}-1-ethyl-3-methyl-6-(trifluoromethyl)-1H-1,3-benzodiazol-3-ium iodide

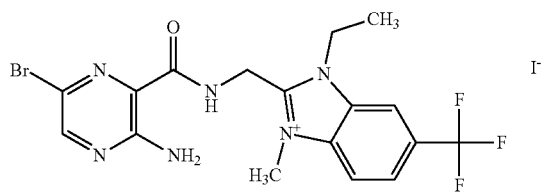 [SMILES: CCn1c(CNC(=O)c2nc(Br)cnc2N)[n+](C)c2ccc(C(F)(F)F)cc21 ; [I-]]

A solution of lithium 3-amino-6-bromopyrazine-2-carboxylate, Intermediate 1 (90 mg, 0.40 mmol), HBTU (168 mg, 0.442 mmol), and DIPEA (140 µl, 0.804 mmol) in anhydrous DMF (0.5 ml) was stirred at RT for 15 min. A solution of 2-(aminomethyl)-1-ethyl-3-methyl-6-(trifluoromethyl)-1H-1,3-benzodiazol-3-ium hydrochloride iodide, Intermediate 29 (169 mg, 0.402 mmol) and DIPEA (140 µl, 0.804 mmol) in DMF (1.5 ml) was added then the reaction was stirred at RT for 16 h. The reaction was evaporated then the crude material was purified by flash column chromatography on C18 (12 g). The column was eluted with MeCN:H$_2$O+0.1% formic acid using the following gradient (% MeCN, column volumes): 0%, 2 CV; 0-40%, 16 CV; 40-100%, 4 CVs; 100%, 2 CV. The desired fractions were combined and evaporated then the residue was further purified by flash column chromatography on C18 (12 g). The column was eluted with MeCN:H$_2$O+0.1% formic acid using the following gradient (% MeCN, column volumes): 10%, 2 CV; 10-50%, 25 CV; 50-100%, 5 CV; 100%, 2 CV. The desired fractions were combined and concentrated in vacuo to remove most of the MeCN. The resulting suspension was filtered then the solid was dried under vacuum to afford the product as a yellow solid (38 mg, 16%).

$^1$H NMR (500 MHz, DMSO-d$_6$) δ 9.54 (t, J=5.3 Hz, 1H), 8.64 (s, 1H), 8.41 (s, 1H), 8.28 (d, J=8.8 Hz, 1H), 8.07 (dd, J=8.8, 1.2 Hz, 1H), 7.64 (s, 2H), 5.07 (d, J=5.3 Hz, 2H), 4.76 (q, J=7.1 Hz, 2H), 4.16 (s, 3H), 1.40 (t, J=7.2 Hz, 3H).

LC/MS (System C): m/z (ESI$^+$)=457 [M($^{79}$Br)$^+$], 459 [M($^{81}$Br)$^+$] R$_t$=2.11 min, UV purity=100%.

Example 14—Synthesis of 2-{[(3-amino-6-bromopyrazin-2-yl)formamido]methyl}-1-ethyl-3-methyl-6-(trifluoromethoxy)-1H-1,3-benzodiazol-3-ium formate

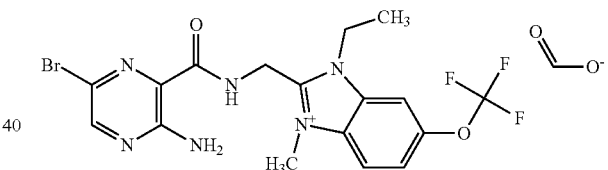

A solution of lithium 3-amino-6-bromopyrazine-2-carboxylate, Intermediate 1 (90 mg, 0.40 mmol), HBTU (168 mg, 0.44 mmol), and DIPEA (140 µl, 0.804 mmol) in DMF (0.5 ml) was stirred at RT for 15 min. A solution of 2-(aminomethyl)-1-ethyl-3-methyl-6-(trifluoromethoxy)-1H-1,3-benzodiazol-3-ium hydrochloride iodide, Intermediate 33 (176 mg, 0.402 mmol) and DIPEA (0.14 ml, 0.804 mmol) in DMF (1.5 ml) was added then the reaction was stirred at RT for 16 h. The reaction mixture was concentrated in vacuo then the crude material was purified by flash column chromatography on C18 (12 g). The column was eluted with MeCN:H$_2$O+0.1% formic acid using the following gradient (% MeCN, column volumes): 0%, 2 CV; 0-40%, 16 CV; 40-100%, 4 CVs; 100%, 2 CV. The desired fractions were combined and evaporated then the residue was further purified by flash column chromatography on C18 (12 g). The column was eluted with MeCN:H$_2$O+0.1% formic acid using the following gradient (% MeCN, column volumes): 10%, 2 CV; 10-50%, 25 CV; 50-100%, 5 CV; 100%, 2 CV. The desired fractions were combined and concentrated in vacuo. The material thus obtained was further purified by preparative HPLC using the following method: Solvent A: Water+0.1% formic acid; Solvent B: MeCN +0.1% formic acid; Column: Waters Sunfire 30 mm×100 mm, 5 micron; Flowrate=40 ml/min; Gradient (time, Solvent B): 0 min, 5%; 1.9 min, 5%; 2 min, 30%; 16 min, 40%; 16.1 min, 95%; 19 min, 95%; 19.1 min, 5%; 20 min, 5%. The desired fractions were combined and concentrated in vacuo to afford the product as an orange solid (40 mg, 19%).

$^1$H NMR (500 MHz, DMSO-d$_6$) δ 9.57 (t, J=5.3 Hz, 1H), 8.40 (d, J=11.4 Hz, 2H), 8.31 (s, 1H), 8.19 (d, J=9.1 Hz, 1H), 7.79-7.72 (m, 1H), 7.65 (s, 2H), 5.04 (d, J=5.2 Hz, 2H), 4.69 (q, J=7.2 Hz, 2H), 4.14 (s, 3H), 1.38 (t, J=7.2 Hz, 3H).

LC/MS (System C): m/z (ESI$^+$)=473 [M($^{79}$Br)$^+$], 475 [M($^{81}$Br)$^+$] R$_t$=2.17 min, UV purity=100%.

Example 15—Synthesis of 2-{[(3-amino-6-bromopyrazin-2-yl)formamido]methyl}-1,3-diethyl-6-(methoxycarbonyl)-1H-1,3-benzodiazol-3-ium iodide

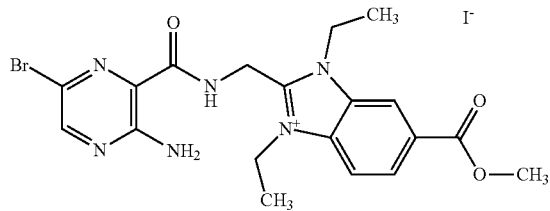 [SMILES: CCn1c(CNC(=O)c2nc(Br)cnc2N)[n+](CC)c2ccc(C(=O)OC)cc21 ; [I-]]

A solution of lithium 3-amino-6-bromopyrazine-2-carboxylate. Intermediate 1 (850 mg, 3.80 mmol), HBTU (1.58 g, 4.18 mmol), and DIPEA (1.32 ml, 7.59 mmol) in anhydrous DMF (3 ml) was stirred at RT for 15 min. A solution of 2-(aminomethyl)-1,3-diethyl-6-(methoxycarbonyl)-1H-1,3-benzodiazol-3-ium hydrochloride iodide, Intermediate 36 (1.62 g, 3.8 mmol) and DIPEA (1.32 ml, 7.59 mmol) in DMF (3 ml) was added then the reaction was stirred at RT for 64 h. The reaction mixture was concentrated in vacuo then the crude material was purified by flash column chromatography on C18 (120 g). The column was eluted with MeCN:H$_2$O using the following gradient (% MeCN, column volumes): 5%, 2 CV; 5-100%, 20 CV; 100%, 2 CV. The cleanest fraction was evaporated to afford the product as a dark brown solid (80 mg). More high purity fractions were combined and evaporated to afford a second batch of product as a dark brown solid (340 mg). The remaining product-containing fractions were combined and evaporated then the material thus obtained was further purified by flash column chromatography on C18 (120 g). The column was eluted with MeCN:H$_2$O using the following gradient (% MeCN, column volumes): 5%, 2 CV; 5-100%, 20 CV; 100%, 2 CV. The desired fractions were combined and concentrated in vacuo to remove most of the MeCN. The resulting aqueous suspension was filtered then the solid was dried under vacuum to afford a third batch of the product as an orange solid (44 mg). The filtrate was concentrated in vacuo to afford a fourth batch of product as a brown gum (113 mg). More product containing fractions from the second column were combined and evaporated to afford a fifth batch of the product as a brown solid (28 mg). The five batches were combined in MeCN then evaporated to afford the product as a brown solid (605 mg, 27%)

$^1$H NMR (500 MHz, DMSO-d$_6$) δ 9.58 (t, J=5.3 Hz, 1H), 8.64 (s, 1H), 8.41 (s, 1H), 8.27-8.17 (m, 2H), 7.65 (s, 2H), 5.10 (d, J=5.4 Hz, 2H), 4.77 (q, J=7.1 Hz, 2H), 4.69 (q, J=7.2 Hz, 2H), 3.95 (s, 3H), 1.44-1.39 (m, 6H).

LC/MS (System C): m/z (ESI$^+$)=461 [M($^{79}$Br)$^+$], 463 [M($^{81}$Br)$^+$] R$_t$=1.96 min, UV purity=99%.

Example 16—Synthesis of 2-{[(3-amino-6-bromopyrazin-2-yl)formamido]methyl}-6-carboxy-1,3-diethyl-1H-1,3-benzodiazol-3-ium bromide

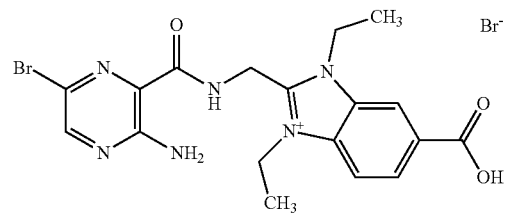 [SMILES: CCn1c(CNC(=O)c2nc(Br)cnc2N)[n+](CC)c2ccc(C(=O)O)cc21 ; [Br-]]

A solution of 5-bromo-3-(1H-imidazole-1-carbonyl)pyrazin-2-amine, Intermediate 2 (40 mg, 0.15 mmol) and 2-(aminomethyl)-6-carboxy-1,3-diethyl-1H-1,3-benzodiazol-3-ium hydrobromide bromide, Intermediate 42 (61 mg, 0.15 mmol) in DMF (1 ml) was stirred at RT for 17 h. The reaction was filtered then the solid collected was washed with MeCN and dried under vacuum to afford the product as an off-white solid (31 mg, 37%).

$^1$H NMR (500 MHz, DMSO-d$_6$) δ 13.58 (s, 1H), 9.60 (t, J=5.3 Hz, 1H), 8.62 (s, 1H), 8.42 (s, 1H), 8.26-8.16 (m, 2H), 7.67 (s, 2H), 5.10 (d, J=5.3 Hz, 2H), 4.80-4.65 (m, 4H), 1.44-1.39 (m, 6H).

LC/MS (System C): m/z (ESI$^+$)=447 [M($^{79}$Br)$^+$], 449 [M($^{81}$Br)$^+$] R$_t$=1.29 min, UV purity=94%.

Example 17—Synthesis of 2-{[(3-amino-6-bromopyrazin-2-yl)formamido]methyl}-1,3-diethyl-6-{[(3R)-2-oxooxolan-3-yl]carbamoyl}-1H-1,3-benzodiazol-3-ium formate

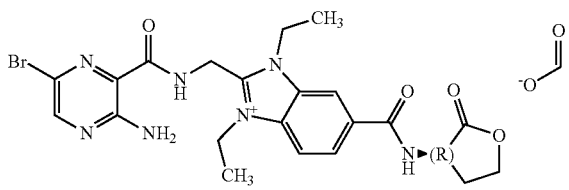

A solution of 2-{[(3-amino-6-bromopyrazin-2-yl)formamido]methyl}-6-carboxy-1,3-diethyl-1H-1,3-benzodiazol-3-ium bromide, Example 16 (60 mg, 0.11 mmol), HBTU (47 mg, 0.13 mmol), and 4-methylmorpholine (29 μl, 0.23 mmol) in anhydrous DMF (0.5 ml) was stirred at RT for 5 min. (3R)-3-Aminooxolan-2-one hydrochloride (16 mg, 0.11 mmol) was added then the reaction was stirred at RT for 4 h. The reaction mixture was concentrated in vacuo then the crude material was purified by flash column chromatography on C18 (12 g). The column was eluted with MeCN:H$_2$O+ 0.1% formic acid using the following gradient (% MeCN, column volumes): 5%, 2 CV; 5-100%, 20 CV; 100%, 2 CV. The desired fractions were combined and lyophilised to afford the product as an off-white solid (22 mg, 32%).

$^1$H NMR (500 MHz, DMSO-d$_6$) δ 9.60 (t, J=5.3 Hz, 1H), 9.39 (d, J=7.9 Hz, 1H), 8.55 (s, 1H), 8.42 (s, 1H), 8.37 (s, 1H), 8.23-8.14 (m, 2H), 7.66 (s, 2H), 5.10 (d, J=5.3 Hz, 2H), 4.89-4.79 (m, 1H), 4.75-4.65 (m, 4H), 4.49-4.40 (m, 1H), 4.35-4.26 (m, 1H), 2.54-2.39 (m, 2H+DMSO-$d_6$), 1.48-1.40 (m, 6H).

LC/MS (System C): m/z (ESI$^+$)=530 [M($^{79}$Br)$^+$], 532 [M($^{81}$Br)$^+$] $R_t$=1.62 min, UV purity=97%.

Example 18—Synthesis of 2-{[(3-amino-6-bromopyrazin-2-yl)formamido]methyl}-1,3-diethyl-6-{[(3S)-2-oxooxolan-3-yl]carbamoyl}-1H-1,3-benzodiazol-3-ium formate

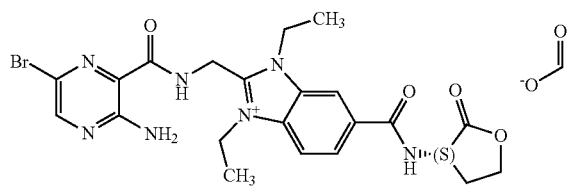

A solution of 2-{[(3-amino-6-bromopyrazin-2-yl)formamido]methyl}-6-carboxy-1,3-diethyl-1H-1,3-benzodiazol-3-ium bromide, Example 16 (70 mg, 0.13 mmol), HBTU (55 mg, 0.13 mmol), and 4-methylmorpholine (34 μl, 0.27 mmol) in anhydrous DMF (0.5 ml) was stirred at RT for 5 min. (3S)-3-Aminooxolan-2-one hydrochloride (18 mg, 0.13 mmol) was added then the reaction was stirred at RT for 16 h. The reaction mixture was concentrated in vacuo then the crude material was purified by flash column chromatography on C18 (12 g). The column was eluted with MeCN:H$_2$O+0.1% formic acid using the following gradient (% MeCN, column volumes): 5%, 2 CV; 5-100%, 20 CV; 100%, 2 CV. The desired fractions were combined and lyophilised to afford the product as an off-white solid (17 mg, 21%).

$^1$H NMR (500 MHz, DMSO-$d_6$) δ 9.60 (t, J=5.2 Hz, 1H), 9.37 (d, J=7.8 Hz, 1H), 8.55 (s, 1H), 8.42 (s, 1H), 8.35 (s, 1H), 8.23-8.14 (m, 2H), 7.66 (s, 2H), 5.10 (d, J=5.3 Hz, 2H), 4.90-4.80 (m, 1H), 4.75-4.65 (m, 4H), 4.50-4.42 (m, 1H), 4.36-4.27 (m, 1H), 2.55-2.38 (m, 2H+DMSO-$d_6$), 1.48-1.40 (m, 6H).

LC/MS (System C): m/z (ESI$^+$)=530 [M($^{79}$Br)$^+$], 532 [M($^{81}$Br)$^+$] $R_t$=1.61 min, UV purity=93%.

Example 19—Synthesis of 2-{[(3-Amino-6-bromopyrazin-2-yl)formamido]methyl}-3-benzyl-1-ethyl-6-(trifluoromethyl)-1H-1,3-benzodiazol-3-ium formate

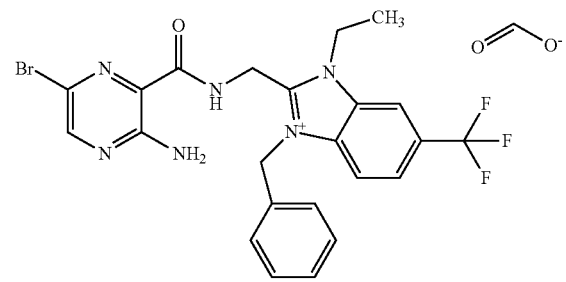

A solution of 5-bromo-3-(1H-imidazole-1-carbonyl)pyrazin-2-amine, Intermediate 2 (55 mg, 0.21 mmol) and 2-(aminomethyl)-3-benzyl-1-ethyl-6-(trifluoromethyl)-1H-1,3-benzodiazol-3-ium hydrochloride bromide, Intermediate 44 (102 mg, 0.226 mmol) in DMF (1 ml) was stirred at RT for 64 h then concentrated in vacuo. The crude material was purified by flash column chromatography on C18 (12 g). The column was eluted with MeCN:H$_2$O+0.1% formic acid using the following gradient (% MeCN, column volumes): 5%, 2 CV; 5-100%, 20 CV; 100%, 2 CV. The desired fractions were combined and evaporated to afford the product as a white solid (68 mg, 57%).

$^1$H NMR (500 MHz, DMSO-$d_6$) δ 9.35 (t, J=5.2 Hz, 1H), 8.74 (s, 1H), 8.44 (s, 1H), 8.31 (s, 1H), 8.11-7.97 (m, 2H), 7.51 (s, 2H), 7.16 (t, J=7.7 Hz, 2H), 7.05 (dd, J=12.7, 7.3 Hz, 3H), 5.94 (s, 2H), 5.19 (d, J=5.2 Hz, 2H), 4.87 (q, J=7.2 Hz, 2H), 1.50 (t, J=7.2 Hz, 3H).

LC/MS (System C): m/z (ESI$^+$)=533 [M($^{79}$Br)$^+$], 535 [M($^{81}$Br)$^+$] $R_t$=2.55 min, UV purity=100%.

Example 20—Synthesis of 2-{[(3-amino-6-bromopyrazin-2-yl)formamido]methyl}-6-(1-{1-[(tert-butoxy)carbonyl]piperidin-4-yl}-1H-pyrazol-4-yl)-1,3-diethyl-1H-1,3-benzodiazol-3-ium iodide

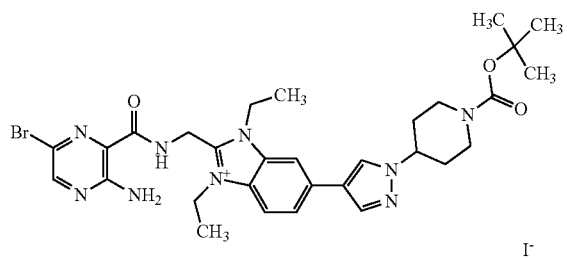 [SMILES: CCn1c(CNC(=O)c2nc(Br)cnc2N)[n+](CC)c2ccc(-c3cnn(C4CCN(C(=O)OC(C)(C)C)CC4)c3)cc21 ; [I-]]

5-bromo-3-(1H-imidazole-1-carbonyl)pyrazin-2-amine, Intermediate 2 (112 mg, 0.42 mmol) was added to a solution of 2-(aminomethyl)-6-(1-{1-[(tert-butoxy)carbonyl]piperidin-4-yl}-1H-pyrazol-4-yl)-1,3-diethyl-1H-1,3-benzodiazol-3-ium iodide, Intermediate 48 (220 mg, 0.38 mmol) in anhydrous DMF (5 ml). The resulting solution was stirred at ambient temperature for 3 h. The reaction mixture was concentrated in vacuo to a brown oil. The crude material was purified by flash column chromatography on C18 (30 g). The column was eluted with MeCN:H$_2$O+0.1% formic acid using the following gradient (% MeCN, column volumes): 5%, 2 CV; 5-100%, 20 CV; 100%, 2 CV. The desired fractions were combined and evaporated to afford the product as a light yellow solid (146 mg, 49%).

$^1$H NMR (500 MHz, DMSO-$d_6$) δ 9.58 (t, J=5.3 Hz, 1H), 8.49 (s, 1H), 8.42 (s, 1H), 8.24 (s, 1H), 8.11 (s, 1H), 8.05 (d, J=8.8 Hz, 1H), 7.93 (d, J=8.9 Hz, 1H), 7.67 (s, 2H), 5.06 (d, J=5.3 Hz, 2H), 4.70-4.62 (m, 4H), 4.40 (t, J=11.5 Hz, 1H), 4.06 (br. s, 2H), 2.95 (br. s, 2H), 2.08 (d, J=8.9 Hz, 2H), 1.86-1.77 (m, 2H), 1.48-1.38 (m, 15H).

LC/MS (System C): m/z (ESI$^+$)=652 [M($^{79}$Br)$^+$+], 654 [M($^{81}$Br)$^+$] R$_t$=2.84 min, UV purity=100%.

Example 21—Synthesis of 2-{[(3-amino-6-bromopyrazin-2-yl)formamido]methyl}-1,3-diethyl-6-[1-(piperidin-4-yl)-1H-pyrazol-4-yl]-1H-1,3-benzodiazol-3-ium hydrochloride iodide

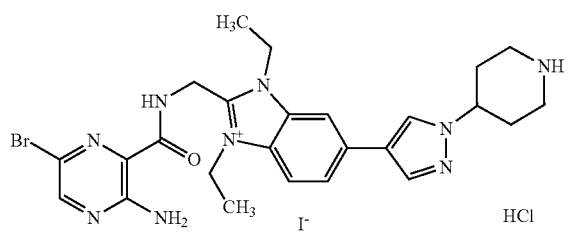 [SMILES: CCn1c(CNC(=O)c2nc(Br)cnc2N)[n+](CC)c2ccc(-c3cnn(C4CCNCC4)c3)cc21 ; Cl ; [I-]]

HCl solution in dioxane (4.0 M, 100 µl, 0.4 mmol) was added to a solution of 2-{[(3-amino-6-bromopyrazin-2-yl)formamido]methyl}-6-(1-{1-[(tert-butoxy)carbonyl]piperidin-4-yl}-1H-pyrazol-4-yl)-1,3-diethyl-1H-1,3-benzodiazol-3-ium iodide, Example 20 (128 mg, 0.164 mmol) in anhydrous MeCN (3 ml). The resulting solution was stirred at ambient temperature for 17 h. The RM was concentrated in vacuo then, azeotroped with MeCN and dried under vacuum to afford the product as a yellow solid (115 mg, 97%).

$^1$H NMR (500 MHz, DMSO-d$_6$) δ 9.59 (t, J=5.3 Hz, 1H), 9.03 (s, 1H), 8.91 (s, 1H), 8.47 (s, 1H), 8.42 (s, 1H), 8.29 (s, 1H), 8.17 (s, 1H), 8.06 (d, J=8.7 Hz, 1H), 7.96 (d, J=8.9 Hz, 1H), 7.66 (s, 2H), 5.07 (d, J=5.2 Hz, 2H), 4.70-4.62 (m, 4H), 4.54-451 (m, 1H), 3.41 (d, J=12.1 Hz, 2H), 3.16-3.06 (m, 2H), 2.29-2.14 (m, 4H), 1.47-1.39 (m, 6H).

LC/MS (System C): m/z (ESI$^+$)=552 [M($^{79}$Br)$^+$], 554 [M($^{81}$Br)$^+$+] R$_t$=1.40 min, UV purity=99%.

Example 22—Synthesis of 2-{[(3-amino-6-bromopyrazin-2-yl)formamido]methyl}-6-[1-(1-carbamimidoylpiperidin-4-yl)-1H-pyrazol-4-yl]-1,3-diethyl-1H-1,3-benzodiazol-3-ium formic acid formate

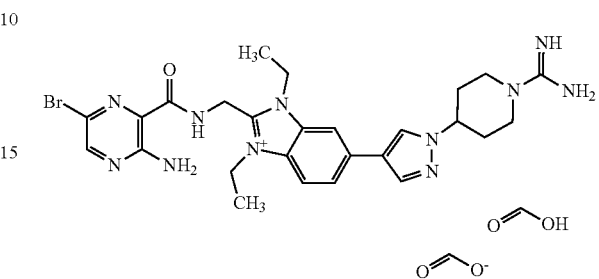

1H-1,2,4-Triazole-1-carboximidamide hydrochloride (21 mg, 0.14 mmol) was added to a solution of 2-{[(3-amino-6-bromopyrazin-2-yl)formamido]methyl}-1,3-diethyl-6-[1-(piperidin-4-yl)-1H-pyrazol-4-yl]-1H-1,3-benzodiazol-3-ium hydrochloride iodide, Example 21 (50 mg, 0.070 mmol) in anhydrous DMF (2 ml). DIPEA (30 µl, 0.17 mmol) was added then the reaction mixture was stirred at RT for 88 h. The reaction mixture was concentrated in vacuo then purified by preparative HPLC. The desired fractions were combined and lyophilised to afford the product as a light yellow solid (21 mg, 44%).

$^1$H NMR (500 MHz, DMSO-d$_6$) δ 9.60 (d, J=5.4 Hz, 1H), 8.50 (s, 1H), 8.48 (s, 2H), 8.42 (s, 1H), 8.26 (s, 1H), 8.12 (s, 1H), 8.05 (d, J=8.7 Hz, 1H), 7.93 (dd, J=8.7, 1.3 Hz, 1H), 7.67 (s, 2H), 5.06 (d, J=4.9 Hz, 2H), 4.69-4.61 (m, 4H), 4.58-4.49 (m, 1H), 3.97 (d, J=13.6 Hz, 2H), 3.21 (t, J=12.3 Hz, 2H), 2.14 (d, J=10.7 Hz, 2H), 1.98-1.87 (m, 2H), 1.47-1.39 (m, 6H).

LC/MS (System C): m/z (ESI$^+$)=297 [M($^{79}$Br)$^+$+H$^+$], 298 [M($^{81}$Br)$^+$+H$^+$] R$_t$=1.51 min, UV purity=100%.

Example 23—Synthesis of 2-{[(3-amino-6-bromopyrazin-2-yl)formamido]methyl}-1,3-diethyl-6-(1-{1-[(2S,3R,4R,5R)-2,3,4,5,6-pentahydroxyhexyl]piperidin-4-yl}-1H-pyrazol-4-yl)-1H-1,3-benzodiazol-3-ium formic acid chloride

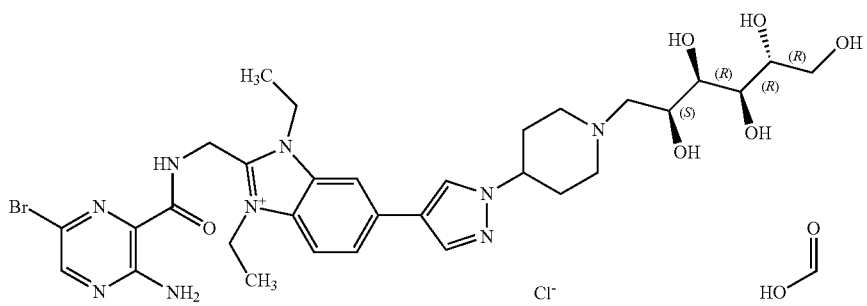

AcOH (7 μl, 0.1 mmol) was added to a solution of 2-{[(3-amino-6-bromopyrazin-2-yl)formamido]methyl}-1,3-diethyl-6-[1-(piperidin-4-yl)-1H-pyrazol-4-yl]-1H-1,3-benzodiazol-3-ium hydrochloride iodide, Example 21 (60 mg, 0.083 mmol) and 4,6-O-benzylidene-D-glucopyranose (62 mg, 0.22 mmol) in anhydrous methanol (1.5 ml). The resulting solution was stirred at RT for 0.5 h then sodium cyanoborohydride (22 mg, 0.34 mmol) was added. The RM was stirred at RT for 4 h. More sodium cyanoborohydride (22 mg, 0.34 mmol) and 4,6-O-benzylidene-D-glucopyranose (62 mg, 0.22 mmol) were added then the reaction was stirred at RT for 16 h. The reaction was added dropwise to saturated aq. NaHCO$_3$ solution (15 ml) then diluted with CH$_2$Cl$_2$ (25 ml). CH$_2$Cl$_2$:MeOH (2:1, 10 ml) was added then the phases were separated. The organic phase was dried over Na$_2$SO$_4$ and concentrated in vacuo to afford the intermediate as a light yellow solid (54 mg). A portion of the material thus obtained (50 mg, 0.057 mmol) was dissolved in aq. HCl solution (2 M, 4 ml). The reaction was stirred at RT for 3.5 h then concentrated in vacuo. The crude material was purified by flash column chromatography on C18 (12 g). The column was eluted with MeCN:H$_2$O+0.1% formic acid using the following gradient (% MeCN, column volumes): 5%, 2 CV; 5-100%, 20 CV; 100%, 2 CV. The desired fractions were combined and lyophilised to afford the product as a white solid (7 mg, 15%).

$^1$H NMR (500 MHz, CD$_3$OD) δ 8.52 (s, 1H), 8.30 (s, 2H), 8.15 (s, 1H), 8.04 (s, 1H), 7.94 (s, 2H), 5.09 (s, 2H), 4.81-4.71 (m, 4H), 4.55 (s, 1H), 4.31-4.25 (m, 1H), 3.98 (q, J=4.9 Hz, 1H), 3.80 (dd, J=11.6, 3.8 Hz, 2H), 3.76-3.61 (m, 3H), 3.22 (d, J=10.6 Hz, 1H), 2.77-2.64 (m, 2H), 2.54-2.35 (m, 2H), 2.20-2.14 (m, 4H), 1.60-1.52 (m, 6H).

LC/MS (System C): m/z (ESI$^+$)=716 [M($^{79}$Br)$^+$], 718 [M($^{81}$Br)$^+$] R$_t$=1.35 min, UV purity=100%.

Example 24—Synthesis of 2-{[(3-amino-6-bromopyrazin-2-yl)formamido]methyl}-6-(2-{[(tert-butoxy)carbonyl]amino}ethoxy)-1,3-diethyl-1H-1,3-benzodiazol-3-ium formate

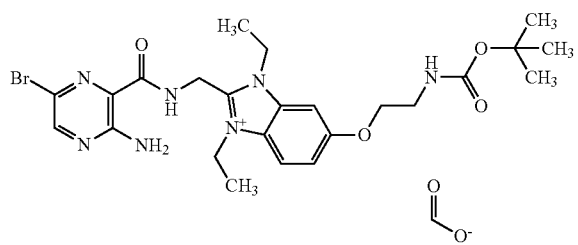

A mixture of 5-bromo-3-(1H-imidazole-1-carbonyl)pyrazin-2-amine, Intermediate 2 (98%, 300 mg, 1.10 mmol) and 2-(aminomethyl)-6-(2-{[(tert-butoxy)carbonyl]amino}ethoxy)-1,3-diethyl-1H-1,3-benzodiazol-3-ium iodide, Intermediate 50 (90%, 598 mg, 1.10 mmol) in DMF (8 ml) was stirred at RT for 2.5 h. The reaction mixture was concentrated in vacuo then the crude material was purified by flash column chromatography on C18 (60 g). The column was eluted with MeCN:H$_2$O+0.1% formic acid using the following gradient (% MeCN, column volumes): 10%, 2 CV; 10-34%, 12 CV; 34-100%, 6 CV; 100%, 2 CV.

The desired fractions were combined and concentrated in vacuo to afford the product as an orange gum (407 mg, 61%).

$^1$H NMR (500 MHz, DMSO-d$_6$) δ 9.57 (t, J=5.3 Hz, 1H), 8.41 (s, 1H), 8.30 (s, 1H), 7.96 (d, J=9.1 Hz, 1H), 7.71-7.59 (m, 3H), 7.27 (dd, J=9.1, 2.1 Hz, 1H), 7.08 (t, J=5.1 Hz, 1H), 5.03 (d, J=5.3 Hz, 2H), 4.66-4.58 (m, 4H), 4.11 (t, J=5.8 Hz, 2H), 1.42-1.36 (m, 15H).

LC/MS (System C): m/z (ESI$^+$)=562 [M($^{79}$Br)$^+$], 564 [M($^{81}$Br)$^+$] R$_t$=2.53 min, UV purity=100%.

Example 25—Synthesis of 2-{[(3-Amino-6-bromopyrazin-2-yl)formamido]methyl}-6-(2-aminoethoxy)-1,3-diethyl-1H-1,3-benzodiazol-3-ium hydrochloride chloride

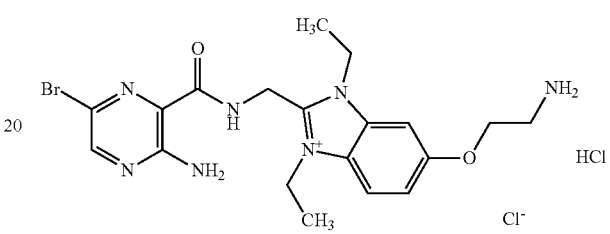

HCl in dioxane (4.0 M, 1.5 ml, 6.0 mmol) was added to a suspension of 2-{[(3-amino-6-bromopyrazin-2-yl)formamido]methyl}-6-(2-{[(tert-butoxy)carbonyl]amino}ethoxy)-1,3-diethyl-1H-1,3-benzodiazol-3-ium formate, Example 24 (407 mg, 0.67 mmol) in MeCN (10 ml). The reaction mixture was stirred at RT for 1 h then concentrated in vacuo. The residue was suspended in MeCN (5 ml). The resulting suspension was filtered then the solid collected was washed with MeCN and dried under vacuum. The filtered material was dried further under high vacuum to afford the product as an orange foam (169 mg, 47%).

$^1$H NMR (500 MHz, DMSO-d$_6$) δ 9.63-9.56 (m, 1H), 8.57-8.38 (m, 4H), 8.00 (d, J=8.9 Hz, 1H), 7.74 (s, 1H), 7.71-7.60 (m, 2H), 7.32 (d, J=8.5 Hz, 1H), 5.05 (d, J=4.5 Hz, 2H), 4.69-4.60 (m, 4H), 4.43-4.35 (m, 2H), 3.25 (s, 2H), 1.42-1.36 (m, 6H).

LC/MS (System C): m/z (ESI$^+$)=462 [M($^{79}$Br)$^+$], 464 [M($^{81}$Br)$^+$] R$_t$=1.09 min, UV purity=99%.

Example 26—Synthesis of 2-{[(3-amino-6-cyanopyrazin-2-yl)formamido]methyl}-1,3-diethyl-6-methoxy-1H-1,3-benzodiazol-3-ium formate

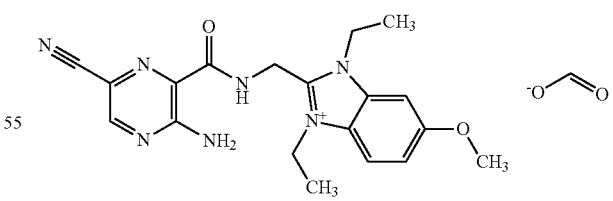

DIPEA (191 μL, 1.10 mmol) was added to a solution of 3-amino-6-cyanopyrazine-2-carboxylic acid, Intermediate 10 (45 mg, 0.27 mmol), 2-(aminomethyl)-1,3-diethyl-6-methoxy-1H-1,3-benzodiazol-3-ium iodide, Intermediate 15 (104 mg, 0.288 mmol) and HBTU (135 mg, 0.356 mmol) in anhydrous DMF (2 ml) was. The resulting mixture was stirred at RT for 1.5 h then water (15 ml) was added. The resulting suspension was stirred at RT for 0.5 h then the precipitate was collected by filtration. The solid was washed with water then dried under vacuum. The crude material thus obtained was purified by preparative HPLC. The desired fractions were combined and lyophilised to afford the product as an off-white solid (8 mg, 7%).

1H NMR (500 MHz, DMSO-$d_6$) δ 9.79 (t, J=5.3 Hz, 1H), 8.72 (s, 1H), 8.43 (s, 1H), 8.34 (s, 1H), 7.97 (d, J=9.1 Hz, 1H), 7.59 (d, J=2.3 Hz, 1H), 7.29 (dd, J=9.1, 2.3 Hz, 1H), 5.04 (d, J=5.3 Hz, 2H), 4.66-4.59 (m, 4H), 3.92 (s, 3H), 1.45-1.36 (m, 6H).

LC/MS (System C): m/z (ESI$^+$)=380 [M$^+$]), $R_t$=1.80 min, UV purity=95%.

C. Biological Examples

Example 27—Short Circuit Current Assay to Determine ENaC Blocker Potency in Human Bronchial Epithelial Cells Cell Culture Human bronchial epithelial cells (HBECs) (Lonza, UK) were cultured using a modification of the method described by Coote et al, (2008). Cells were seeded into plastic T-75 flasks and grown in Bronchial Epithelial Cell Growth Medium (BEGM) (Lonza, UK) supplemented with bovine pituitary extract (52 ng/mL), hydrocortisone (0.5 µg/mL), human recombinant Epidermal Growth Factor (0.5 ng/mL), epinephrine (0.5 ng/mL), transferrin (10 ng/mL), insulin (5 ng/mL), retinoic acid (0.1 ng/mL), triiodothyronine (6.5 ng/mL), gentamycin (50 µg/mL) and amphotericin-B (50 ng/mL). Medium was changed every 48 hours until cells were 90% confluent. Cells were then passaged and seeded ($8.25 \times 10^5$ cells/insert) onto polycarbonate Snapwell™ inserts (Costar, UK) in differentiation media containing 50% DMEM in BGEM with the same supplements as above but without triiodothyronine and a final retinoic acid concentration of 50 nM (all-trans retinoic acid; Sigma-Aldrich, UK). Cells were maintained submerged for the first 7 days in culture after which time they were exposed to an apical air interface for the remainder of the culture period. From the first day of establishment of an ALI, HBEC were fed with a DMEM:HAMS F-12 (1:1) media containing 2% Ultroser G (Pall BioSepra, France) with gentamycin (50 µg/mL) and amphotericin B (50 ng/mL). Cells were used for short-circuit current assay between days 14-21 after the establishment of the ALI. At all stages of culture, cells were maintained at 37'C in 5% $CO_2$ in an air incubator.

Short-Circuit Current (ISC) Measurements

Snapwell inserts were mounted in Costar Vertical Diffusion Chambers (Costar, UK) and were bathed with continuously gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$ and 10 glucose. The solution osmolarity was always between 280-300 mOsm/kg $H_2O$ for all physiological salt solutions used. Cells were voltage clamped to 0 mV (model EVC4000, WPI). Transepithelial resistance (RT) was measured by applying a 2 mV pulse at 30 s intervals and calculating RT by Ohm's law. Data were recorded using a PowerLab workstation (ADInstruments, UK).

ENaC blocker compounds were added to the apical chamber from a 1000-fold stock solution (prepared in DMSO) to achieve a cumulative concentration response in terms of the inhibition of the basal ISC. At the completion of the concentration response, a supra-maximal concentration of amiloride (10 µM) was added. The concentration of test compound that induced a 50% inhibition of the total amiloride-sensitive ISC ($IC_{50}$) was calculated using Graph-Pad Prism v6.05.

Example 28—Microsomal Stability

Microsomes (rat and human) were obtained from Bioreclamation. Test compound stock solutions in DMSO (10 mM) were diluted with DMSO to 2 mM. Further dilution was completed to achieve a 100 µM stock (final concentrations; 91.5% Acetonitrile: 8.5% DMSO). Final test compound concentration in incubation was 1 µM (<0.1% DMSO). The following probe substrates were used: verapamil, propranolol, metoprolol and phenacetin (rat) at a final incubation concentration of 1 µM. Assay buffer—Solution 1: 17.4 g potassium phosphate dibasic anhydrous (K2HPO4, 0.1 M) dissolved in 1 L deionised water. Solution 2: 13.6 g potassium phosphate monobasic anhydrous (KH2PO4, 0.1 M) dissolved in 1 L deionised water. Potassium phosphate solutions 1 and 2 were combined to form a pH 7.42 solution at 37° C. pH 7.4 with 2 mM magnesium chloride. NADPH (10 mM)—diluted in deionised water. Frozen microsomes were thawed at 37° C. Microsomes were diluted in assay buffer to achieve a final protein concentration of 0.5 mg/mL and 1 mM NADPH. The following procedure was completed on a Perkin Elmer Janus robotic platform in 96 well format: The microsomal incubation plate was transferred to a heater shaker at 300 rpm and solution heated to 37° C. for 10 min pre-warm. A no co-factor control at 0 and 45 min and one replicates of each test compound was included in every assay. Microsomes were incubated at 37° C., on a shaker set at 300 rpm throughout the assay. At each timepoint (0, 5, 15, 30, 45 min) 50 µL of sample was removed from the 96-well and added to 200 µL of quench solution (acetonitrile containing 0.1% formic acid and imipramine/labetalol, 200 nM). Samples were diluted 1:1 with water using the Janus Robot and analysed by LC-MS/MS.

Example 29—Hepatic Stability

Cryopreserved hepatocytes (rat and human) were obtained from Bioreclamation. Test compound stock solutions in DMSO (10 mM) were diluted with DMSO to 4 mM. Further dilution was completed to achieve a 100 µM stock (5 µL of 4 mM in 195 µL of 50:50 DMSO:hepatocyte buffer). Final test compound concentration in incubation was 1 µM. The following probe substrates were used: testosterone and carbamazepine at a final incubation concentration of 1 µM. Hepatocyte buffer was prepared (Williams E media containing phenol red and Glutamax™, 15 mM HEPES, warmed to 37° C., pH7.4 with NaOH). Cells were removed from liquid nitrogen, thawed in a waterbath, decanted into 50 mL of pre-warmed Cryopreserved Hepatocyte Recovery Media (LifeTechnologies) and centrifuged. Supernatant fraction was removed, cells were re-suspended in hepatocyte buffer and counted by trypan blue exclusion. Cell viability of >80% was required for all assays. Cells were re-suspended to $1 \times 10^6$/mL and 198 µL cell suspension added to each 96-well. 2 µL of 100 µM compound stock solution was added to relevant wells to initiate the incubation. A no cell control and two replicates of each test compound was included in every assay. Cells were incubated at 37° C., on a shaker set at 300 rpm. At each timepoint (0, 15, 30, 45, 60, 90 min) 20 µL of sample was removed from the 96-well and added to 80 µL of quench solution (acetonitrile containing 0.1% formic acid and imipramine/labetalol, 200 nM). Samples were diluted 1:1 with water using the Janus Robot and analysed by LC-MS/MS. The results of Examples 28 to 30 are presented in Table 2.

TABLE 2

| Example No. | Averages. ENaC Ic50 µm Avg | Averages. Mic Half Life Human (mins) | Averages. Mic Half Life Rat (mins) | Averages. Hep Half Life Human (mins) | Averages. Hep Half Life Rat (mins) |
|---|---|---|---|---|---|
| 1  | 5     | 12   | 3    | 44   | 6   |
| 2  | 0.001 | 58   | 3    | 90   | 5   |
| 3  | 0.001 | 89   | 4    | 240  | 13  |
| 4  | 0.004 | 86   | 8    | 240  | 16  |
| 5  | 0.002 | 12   | 4    | 68   | 5   |
| 7  | 0.004 | 22   | 7    | 129  | 16  |
| 8  | 0.224 | 23.  | 3    |      |     |
| 9  | 0.074 | 5    | 3    |      |     |
| 11 | 0.002 | 138  | 4    | 240  | 6   |
| 12 | 0.019 | 111  | 4    |      |     |
| 13 | 0.004 | 138  | 5    | 240  | 14  |
| 14 | 0.003 | 138  | 11   | 205  | 28  |
| 15 | 0.002 | 138  | 11   | 154  | 14  |
| 16 | 0.014 |      |      |      |     |
| 17 | 0.003 | 135  | 29   | 101  | 32  |
| 18 | 0.004 | >138 | 61   | 137  | 46  |
| 19 | 0.004 |      |      | 240  | 17  |
| 20 | 0.001 | >138 | 61   | 70   | 20  |
| 21 | 0.001 | 92   | 77   | 66   | 25  |
| 22 | 0.002 | >138 | >138 | 67   | 90  |
| 23 | 0.002 | >138 | >138 | 72   | 124 |
| 24 | 0.002 | 59   | 37   | 73   | 42  |
| 25 | 0.002 | >138 | >138 | >240 | 59  |
| 26 | 0.008 | >138 | <3   | 232  | 23  |

REFERENCES

App E M, King M, Helfesrieder R, Köhler D and Matthys H. Acute and long-term amiloride inhalation in cystic fibrosis lung disease. A rational approach to cystic fibrosis therapy. Am Rev Respir Dis., 1990, 141(3):605-12.

Botero-Velez M, Curtis J J and Warnock D G. Brief report: Liddle's syndrome revisited—a disorder of sodium reabsorption in the distal tubule. N Engl J Med., 1994, 330(3):178-81.

Boucher R C. Evidence for airway surface dehydration as the initiating event in C F airway disease. J Intern Med., 2007, 261(1):5-16.

Bowler I M, Kelman B, Worthington D, Littlewood J M, Watson A, Conway S P, Smye S W, James S L and Sheldon T A. Nebulised amiloride in respiratory exacerbations of cystic fibrosis: a randomised controlled trial. Arch Dis Child., 1995, 73(5):427-30.

Chang S S, Grunder S, Hanukoglu A, Rösler A, Mathew P M, Hanukoglu I, Schild L, Lu Y, Shimkets R A, Nelson-Williams C, Rossier B C and Lifton R P. Mutations in subunits of the epithelial sodium channel cause salt wasting with hyperkalaemic acidosis, pseudohypoaldosteronism type 1. Nat Genet., 1996, 12(3):248-53.

Fajac I, Hubert D, Guillemot D, Honoré I, Bienvenu T, Volter F, Dall'Ava-Santucci J and Dusser D J. Nasal airway ion transport is linked to the cystic fibrosis phenotype in adult patients. Thorax, 2004, 59(11):971-6.

Frateschi S, Charles R-P, Hummler E. The Epithelial Sodium Channel ENaC and its Regulators in the Epidermal Permeability Barrier Function. The Open Dermatology Journal, 2010, 4: 27-35.

Graham A, Hasani A, Alton E W, Martin G P, Marriott C, Hodson M E, Clarke S W and Geddes D M. No added benefit from nebulized amiloride in patients with cystic fibrosis. Eur Respir J., 1993, 6(9):1243-8.

Kellenberger S and Schild L. Epithelial sodium channel/degenerin family of ion channels: a variety of functions for a shared structure. Physiol Rev., 2002 82(3):735-67.

Kerem E, Bistritzer T, Hanukoglu A, Hofmann T, Zhou Z, Bennett W, MacLaughlin E, Barker P, Nash M, Quittell L, Boucher R and Knowles M R. Pulmonary epithelial sodium-channel dysfunction and excess airway liquid in pseudohypoaldosteronism. N Engl J Med., 1999, 341(3):156-62.

Knowles M R, Stutts M J, Spock A, Fischer N, Gatzy J T and Boucher R C. Abnormal ion permeation through cystic fibrosis respiratory epithelium. Science, 1983, 221(4615):1067-70.

Knowles M R, Church N L, Waltner W E, Yankaskas J R, Gilligan P, King M, Edwards L J, Helms R W and Boucher R C. A pilot study of aerosolized amiloride for the treatment of lung disease in cystic fibrosis. N Engl J Med., 1990, 322(17):1189-94.

Leal T, Fajac I, Wallace H L, Lebecque P, Lebacq J, Hubert D, Dall'Ava J, Dusser D, Ganesan A P, Knoop C, Cumps J, Wallemacq P and Southern K W. Airway ion transport impacts on disease presentation and severity in cystic fibrosis. Clin Biochem., 2008, 41(10-11):764-72.

Matsui H, Grubb B R, Tarran R, Randell S H, Gatzy J T, Davis C W and Boucher R C. Evidence for periciliary liquid layer depletion, not abnormal ion composition, in the pathogenesis of cystic fibrosis airways disease. Cell, 1998, 95(7):1005-15.

Middleton P G, Geddes D M and Alton E W. Effect of amiloride and saline on nasal mucociliary clearance and potential difference in cystic fibrosis and normal subjects. Thorax, 1993, 48(8):812-6.

Noone P G, Regnis J A, Liu X, Brouwer K L, Robinson M, Edwards L and Knowles M R. Airway deposition and clearance and systemic pharmacokinetics of amiloride following aerosolization with an ultrasonic nebulizer to normal airways. Chest, 1997, 112(5):1283-90.

Perazella M A. Drug-induced hyperkalemia: old culprits and new offenders. Am J Med., 2000, 109(4):307-14.

Pons G, Marchand M C, d'Athis P, Sauvage E, Foucard C, Chaumet-Riffaud P, Sautegeau A, Navarro J and Lenoir G. French multicenter randomized double-blind placebo-controlled trial on nebulized amiloride in cystic fibrosis patients. The Amiloride-AFLM Collaborative Study Group. Pediatr Pulmonol., 2000, 30(1):25-31.

Thelin W R, Johnson M R, Hirsh A J, Kublin C L, Zoukhri D. Effect of Topically Applied Epithelial Sodium Channel Inhibitors on Tear Production in Normal Mice and in Mice with Induced Aqueous Tear Deficiency. J Ocul Pharmacol. Ther. 2012, 28(4): 433-438.

The invention claimed is:
1. A compound of formula (I), or a tautomer or enantiomer thereof:

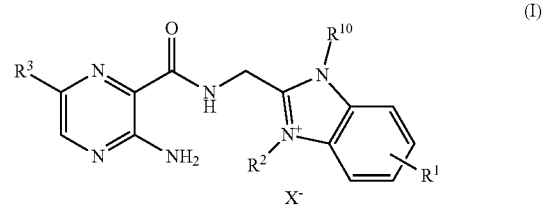

wherein:

X⁻ is an anion;

R¹ is:

(i) H, halo; or (ii) $C_{1-6}$ alkyl, $C_{2-6}$ alkenyl, $C_{2-6}$ alkynyl, —O($C_{1-6}$ alkyl), —O($C_{2-6}$ alkenyl) or —O($C_{2-6}$ alkynyl) any of which is optionally substituted by one or more halo substituents; or (iii) —L¹R¹¹, —O—L¹R¹¹, —OR⁵, —SO₂R⁵, —C(O)OR⁵, —C(O)NR⁵R⁶ or —C(=NR⁷)NR⁵R⁶;

L¹ is $C_{1-6}$ alkylene, $C_{2-6}$ alkenylene or $C_{2-6}$ alkynylene;

R₁₁ is H, —NR⁷R⁸, —NR⁷—C(=NR⁹)N(R⁸)₂, —NR⁷—C(O)O—R⁸, —NR⁷—C(O)—($C_{1-3}$ alkylene)—N⁺(R⁸)₃, or —N⁺(R⁸)₃;

each R⁷, R⁸ and R⁹ is independently selected from H or $C_{1-4}$ alkyl;

each R⁵ and R⁶ is independently H, $C_{1-6}$ alkyl, $C_{2-6}$ alkenyl, $C_{2-6}$ alkynyl, cycloalkyl containing 3 to 8 ring carbon atoms, or heterocyclyl containing 3 to 8 ring atoms, any of which is optionally substituted by one or more substituents selected from halo, OR⁷, C(O)OR⁷, —NR⁷R⁸, C(O)NR⁷R⁸ or, in the case of cycloalkyl or heterocyclyl groups, oxo; or (iv) —L²—R¹² wherein L² is:

a bond;

—$Z_{12}$—, -aryl-, -heteroaryl-, -carbocyclyl-, -heterocyclyl-,

—Z₆-carbocyclyl-, —Z₆-heterocyclyl-, —Z₆-aryl-, —Z₆-heteroaryl-;

-carbocyclyl-Z₆—, -heterocyclyl-Z₆—, -aryl-Z₆—, -heteroaryl-Z₆—;

—Z₆—NR⁷—Z₆—;

—O$Z_{12}$—, —O-aryl-, —O-heteroaryl-, —O-carbocyclyl-, —O-heterocyclyl-,

—OZ₆-carbocyclyl-, —OZ₆-heterocyclyl-, —OZ₆-aryl-, —OZ₆-heteroaryl-;

—O-carbocyclyl-Z₆—, —O-heterocyclyl-Z₆—, —O-aryl-Z₆—, —O-heteroaryl-Z₆—;

—OZ₆—NR⁷—Z₆—,

—C(O)$Z_{12}$—, —C(O)-carbocyclyl-, —C(O)-heterocyclyl-, —C(O)-carbocyclyl-Z₆—, —C(O)-heterocyclyl-Z₆—, —C(O)—Z₆-carbocyclyl-, C(O)—Z₆-heterocyclyl-, —C(O)—Z₆-carbocyclyl-Z₆—, C(O)—Z₆-heterocyclyl-Z₆—, —C(O)NR⁷—, —C(O)NR⁷—$Z_{12}$—, —C(O)NR⁷-carbocyclyl-, C(O)NR⁷-heterocyclyl-, C(O)NR7-aryl-, C(O)NR⁷-heteroaryl-, —C(O)NR⁷-carbocyclyl-Z₆—, —C(O)NH-heterocyclyl-Z₆—, —C(O)NR⁷—Z₆-carbocyclyl-, —C(O)NR⁷—Z₆-heterocyclyl-, —C(O)NR⁷—Z₆-carbocyclyl-Z₆—, —C(O)NR⁷—Z₆-heterocyclyl-Z₆—;

—Z₆—C(O)NR⁷—Z₆—, —Z₆—C(O)NR⁷-aryl-, —Z₆—C(O)NR⁷-heteroaryl-, —Z₆—C(O)NR⁷-carbocyclyl-, —Z₆—C(O)NR⁷-heterocyclyl-, —Z₆—C(O)NR⁷-aryl-Z₆—, —Z₆—C(O)NR⁷-heteroaryl-Z₆—, —Z₆—C(O)NR⁷-carbocyclyl-Z₆— or —Z₆—C(O)NR⁷-heterocyclyl-Z₆—;

—C(O)$Z_{12}$—, —C(O)-carbocyclyl-, —C(O)-heterocyclyl-, —C(O)-carbocyclyl-Z₆—, —C(O)-heterocyclyl-Z₆—, —C(O)—Z₆-carbocyclyl-, C(O)—Z₆-heterocyclyl-, —C(O)—Z₆-carbocyclyl-Z₆—, C(O)—Z₆-heterocyclyl-Z₆—, —C(=N)NR⁷—$Z_{12}$—, —C(=N)NR⁷-carbocyclyl-, C(=N)NR⁷-heterocyclyl-, —C(=N)NR⁷-carbocyclyl-Z₆—, —C(=N)NH-heterocyclyl-Z₆—, —C(=N)NR⁷—Z₆-carbocyclyl-, —C(=N)NR⁷—Z₆-heterocyclyl-, —C(=N)NR⁷—Z₆-carbocyclyl-Z₆—, or —C(=N)NR⁷—Z₆-heterocyclyl-Z₆—;

wherein $Z_{12}$ is $C_{1-12}$ alkylene, $C_{2-12}$ alkenylene or $C_{2-12}$ alkynylene;

Z₆ is $C_{1-6}$ alkylene, $C_{2-6}$ alkenylene or $C_{2-6}$ alkynylene, and alkylene, alkenylene and alkynylene groups are optionally substituted with one or more substituents selected from NR⁸R⁹, C(O)NR⁸R⁹, OH or halo, wherein R⁷, R⁸ and R⁹ are as defined above; and R¹² is —NR¹⁴R¹⁵ or —G—R¹⁴;

each of R¹⁴ and R¹⁵ is independently $C_{1-8}$ alkyl optionally substituted with one or more OH groups; and G is a 5- to 10-membered heterocyclic ring optionally substituted with one or more OH groups and containing at least one nitrogen atom which is connected by a covalent bond to the group R¹⁴; or (v) —L³—R¹³, wherein L³ is selected from the group consisting of one and two cyclic groups directly linked to one another wherein each cyclic group is selected from aryl, heteroaryl, carbocyclyl and heterocyclyl, wherein cycloalkyl and heterocyclyl groups may have one or more oxo substituents; and R¹³ is H, —OR⁵ —SO₂R⁵, —C(O)OR⁵, —C(O)NR⁵R⁶ or —C(=NR⁷)NR⁵R⁶; wherein R⁵, R⁶ and R⁷ are as defined above;

wherein, in (iv) and (v):

heteroaryl is an aromatic ring system having from 5 to 14 ring atoms, at least one of which is a heteroatom selected from N, O, or S, and containing up to three rings;

carbocyclyl is a non-aromatic hydrocarbon ring system containing from 3 to 10 ring carbon atoms and optionally one or more double bonds; and heterocyclyl is a non-aromatic ring system containing 3 to 10 ring atoms including at least one heteroatom selected from N, O, or S;

R² is $C_{1-10}$ alkyl, wherein one or more —CH₂— groups is optionally replaced by —O— and which is optionally substituted with one or more substituents selected from halo, aryl, heteroaryl, —OR⁷ and —NR⁷R⁸, wherein R⁷ and R⁸ are as defined above;

R³ is H, halo, cyano, $C_{1-3}$ alkyl, $C_{1-3}$ haloalkyl, or —S($C_{1-3}$ alkyl); and R¹⁰ is $C_{1-6}$ alkyl optionally substituted with one or more substituents selected from halo, —OR⁷ and —NR⁷R⁸, wherein R⁷ and R⁸ are as defined above;

provided that when R² is ethyl; R³ is chloro and R¹⁰ is ethyl:

R¹ is not C(O)NR⁵R⁶, wherein at least one of R⁵ and R⁶ is $C_{1-6}$ alkyl substituted with one or more substituents selected from OH and NR⁷R⁸, where R⁷ and R⁸ are each independently H or methyl; and R¹ is not L²R¹² where L² is C(O)heterocyclyl and R¹² is N(CH₃)₂.

2. A compound according to claim 1, which is a compound of formula (IC):

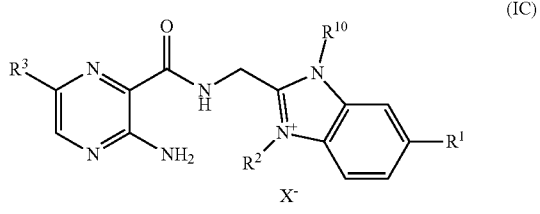

(IC)

or a compound of formula (ID):

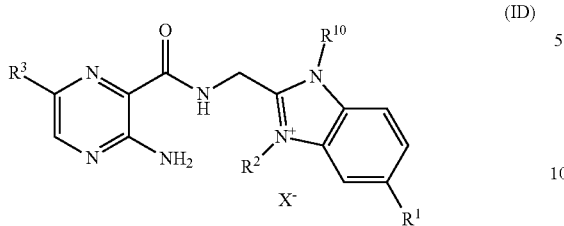

3. A compound according to claim 1 wherein R$^1$ is: H, halo; or C$_{1-6}$ alkyl, C$_{2-6}$ alkenyl, C$_{2-6}$ alkynyl, —O(C$_{1-6}$ alkyl), —O(C$_{2-6}$ alkenyl) or —O(C$_{2-6}$ alkynyl), any of which is optionally substituted by one or more halo substituents.

4. A compound according to claim 3, wherein R$^1$ is H, chloro, methyl, trifluoromethyl, methoxy or trifluoromethoxy.

5. A compound according to claim 1 wherein R$^1$ is —L$^1$R$^{11}$, —O—L$^1$R$^{11}$, —OR$^5$ —SO$_2$R$^5$, —C(O)OR$^5$, —C(O)NR$^5$R$^6$ or —C(=NR$^7$)NR$^5$R$^6$.

6. A compound according to claim 5 wherein L$^1$ is C$_{1-6}$ alkylene.

7. A compound according to claim 5 wherein R$^1$ is —L$^1$R$^{11}$ and L$^1$ is —(CH$_2$)$_n$— where n is 1 to 6; or wherein R$^1$ is —O—L$^1$—R$^{11}$, L$^1$ is —(CH$_2$)$_m$—, where m is 1 to 5.

8. A compound according to claim 5 wherein R$^{11}$ is H, —NR$^7$R$^8$, —NR$^7$—C(=NR$^9$)N(R$^8$)$_2$, —NR$^7$—C(O)O—R$^8$, —NR$^7$—C(O)—(C$_{1-3}$ alkylene)—N$^+$(R$^8$)$_3$ or —N$^+$(R$^8$)$_3$ where each R$^7$, R$^8$ and R$^9$ is selected from H and C$_{1-4}$ alkyl.

9. A compound according to claim 8 wherein R$^{11}$ is —NH$_2$, —NH—C(=NH)NH$_2$, —NH—C(O)O—C(CH$_3$)$_3$, —NH—C(O)—CH$_2$—N$^+$(CH$_3$)$_3$ and —N$^+$(CH$_3$)$_3$.

10. A compound according to claim 1, wherein

R$^1$ is —OR$^5$, —C(O)OR$^5$, —C(O)NR$^5$R$^6$ or —C(=NR$^7$)NR$^5$R$^6$, and R$^5$ and R$^6$ are selected from H and C$_{1-6}$ alkyl; or R$^1$ is —SO$_2$R$^5$ and R$^5$ is C$_{1-6}$ alkyl; or R$^1$ is —OR$^5$, —C(O)OR$^5$, —C(O)NR$^5$R$^6$ or —C(=NR$^7$)NR$^5$R$^6$ or —SO$_2$R$^5$; R$^6$ (when present) is H and R$^5$ is a 5- or 6-membered carbocyclic or heterocyclic group optionally substituted with an oxo.

11. A compound according to claim 10 wherein R$^1$ is —OCH$_3$, —OCF$_3$, —C(O)OCH$_3$, —C(O)OH, —NH—C(O)O—C(CH$_3$)$_3$, —C(=NH)NH$_2$, —SO$_2$—CH$_3$, —C(O)N(CH$_3$)$_2$ or:

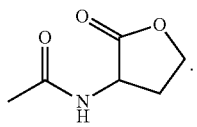

12. A compound according to claim 1 wherein R$^1$ is —L$^2$—R$^{12}$, wherein, in the linker group L$^2$, independently or in any combination:

R$^7$ (when present) is H;

heterocyclyl groups are piperidinyl groups;

the heteroaryl group is:

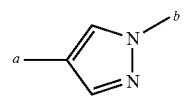

where a is the link to the remainder of the molecule and b is the link to R$^{12}$;

Z$_{12}$ and Z$_6$ groups are optionally substituted with —NH$_2$, —N(CH$_3$)$_2$, —C(O)NH$_2$, —C(O)N(CH$_3$)$_2$, OH and halo.

13. A compound according to claim 12 wherein L$^2$ is:
a bond;
—Z$_{12}$—, -aryl-, -heteroaryl-, -carbocyclyl-, -heterocyclyl-,
—Z$_6$-carbocyclyl-, —Z$_6$-heterocyclyl-, —Z$_6$-aryl-, —Z$_6$-heteroaryl-;
-carbocyclyl-Z$_6$—, -heterocyclyl-Z$_6$—, -aryl-Z$_6$—, -heteroaryl-Z$_6$—;
—Z$_6$—NR$^7$—Z$_6$—;
—OZ$_{12}$—, —O-aryl-, —O-heteroaryl-, —O-carbocyclyl-, —O-heterocyclyl-,
—OZ$_6$-carbocyclyl-, —OZ$_6$-heterocyclyl-, —OZ$_6$-aryl-, —OZ$_6$-heteroaryl-;
—O-carbocyclyl-Z$_6$—, —O-heterocyclyl-Z$_6$—, —O-aryl-Z$_6$—, —O-heteroaryl-Z$_6$—;
—OZ$_6$—NR$^7$—Z$_6$—,
—C(O)-heterocyclyl-, —C(O)-heterocyclyl-Z$_6$—,
—C(O)NR$^7$—, —C(O)NR$^7$—Z$_{12}$—, —C(O)NR$^7$—Z$_6$-heterocyclyl-, —C(O)NR$^7$-Z$_6$-carbocyclyl-Z$_6$—, —C(O)NR$^7$—Z$_6$-heterocyclyl-Z$_6$—;
—Z$_6$—C(O)NR$^7$—Z$_6$—, —Z$_6$—C(O)NR$^7$-aryl-, —Z$_6$—C(O)NR$^7$-heteroaryl-, —Z$_6$—C(O)NR$^7$——Z$_6$—C(O)NR$^7$-aryl-Z$_6$—, or —Z$_6$—C(O)NR$^7$-heteroaryl-Z$_6$—.

14. A compound according to claim 13, wherein L$^2$ is:
a bond,
—OCH$_2$CH$_2$—,
—CH$_2$CH$_2$CH$_2$—,

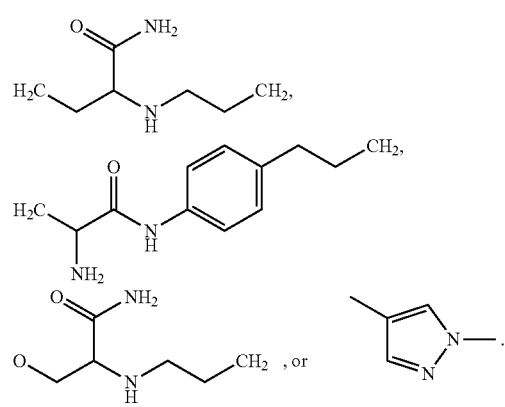

15. A compound according to claim 12 wherein R$^{12}$ is —NR$^{14}$R$^{15}$ or —G—R$^{14}$; wherein, independently or in combination:
G is piperidinyl of formula

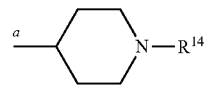

where the piperidinyl group is joined to $L^2$ at a; and
each of $R^{14}$ and $R^{15}$ is independently $C_{4-8}$ alkyl optionally substituted with one or more OH groups.

16. A compound according to claim 15 wherein $R^{14}$ and optionally $R^{15}$ is:
$C_4$ alkyl having three OH substituents; or
$C_5$ alkyl having four OH substituents; or
$C_6$ alkyl having five OH substituents; or
$C_7$ alkyl having six OH substituents; or
$C_8$ alkyl having seven OH substituents.

17. A compound according to claim 1 wherein $R^1$ is $—L^3—R^{13}$, wherein $L^3$ comprises a carbocyclic or heterocyclic group optionally linked to an aryl or heteroaryl group wherein both the carbocyclic or heterocyclic group and the aryl or heteroaryl group are 5- or 6-membered rings.

18. A compound according to claim 17 wherein $L^3$ is piperidine or piperazine and wherein the $R^{13}$ group is attached to the nitrogen at the 1-position and the piperidine or piperazine ring is linked via the 4-position to the remainder of the molecule or (when present) to the aryl group which comprises the remainder of the $L^3$ linker.

19. A compound according to claim 18 wherein $L^3$ is one of:

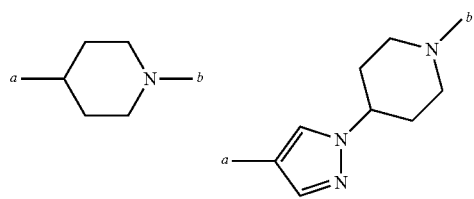

wherein a is the link to the remainder of the molecule and b is the link to $R^{13}$.

20. A compound according to any one of claims 17 to 19 wherein $R^{13}$ is H, $—OR^5$ $—SO_2R^5$, $—C(O)OR^5$, $—C(O)NR^5R^6$ or $—C(=NR^7)NR^5R^6$.

21. A compound according to claim 20 wherein $R^{13}$ is $—OCH_3$, $—OCF_3$, $—C(O)OCH_3$, $—C(O)OH$, $—NH—C(O)O—C(CH_3)_3$, $—C(=NH)NH_2$, $—SO_2—CH_3$, $—C(O)N(CH_3)_2$ or:

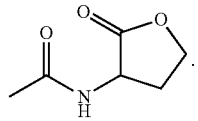

22. A compound according to claim 1 wherein $R^2$ is $—(CH_2)_sCH_3$ or $(CH_2CH_2O)_t—H$, wherein one or more $—CH_2—$ groups is optionally replaced by $—O—$ and which is optionally substituted with one or more substituents selected from halo, aryl, heteroaryl, $—OR^7$ and $—NR^7R^8$ and wherein s is 0-9, and t is 1-3.

23. A compound according to claim 1 wherein $R^3$ is halo, cyano or methyl, ethyl, methylthio or ethylthio, any of which is optionally substituted with one or more halo substituents.

24. A compound according to claim 1 wherein $R^{10}$ is H or $C_{1-6}$ alkyl optionally substituted with one or more substituents selected from halo, $—OR^6$ and $—NR^6R^7_7$.

25. A compound according to claim 1 selected from:

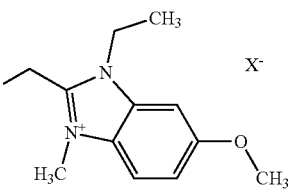

1

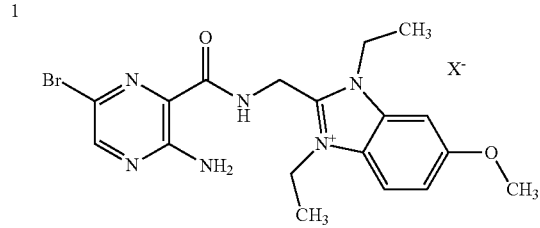

2

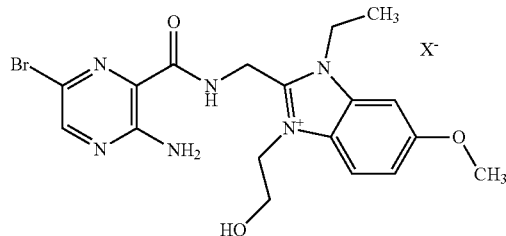

3

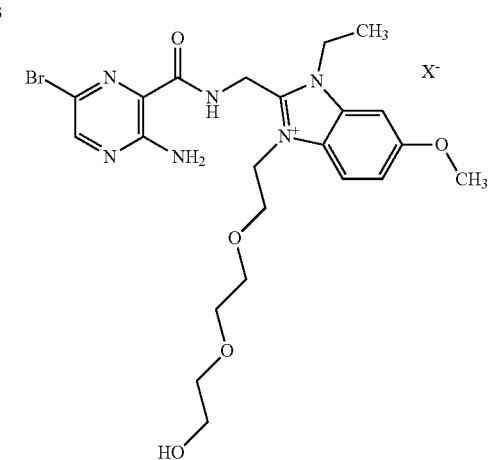

4

-continued
| | | |
|---|---|---|
| 5 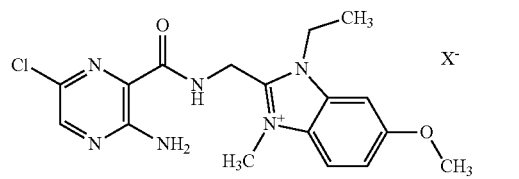 | 6 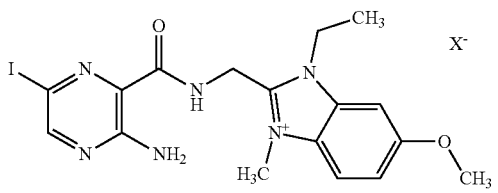 | |
| 7 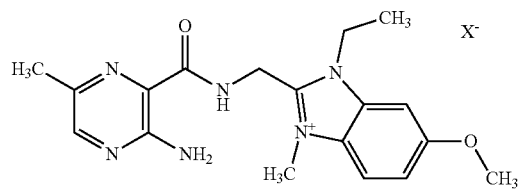 | 8 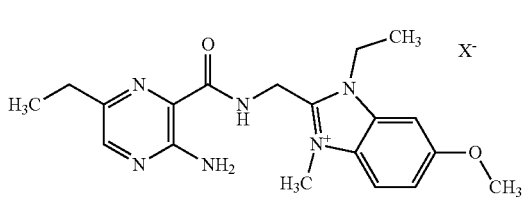 | |
| 9 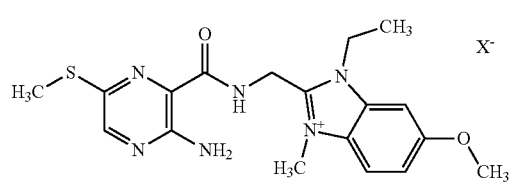 | 10 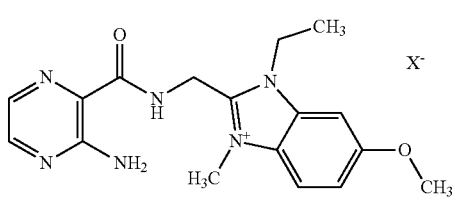 | |
| 11 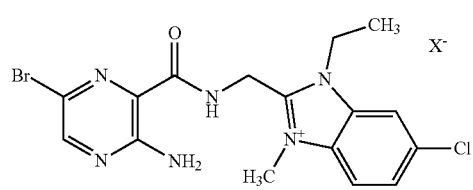 | 12 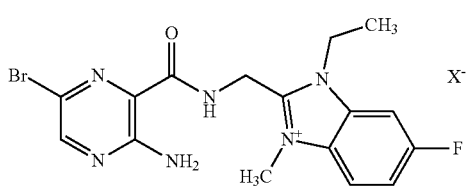 | |
| 13 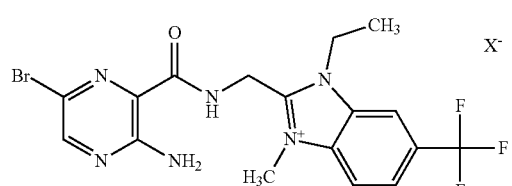 | 14 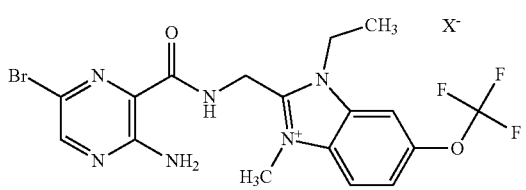 | |
| 15 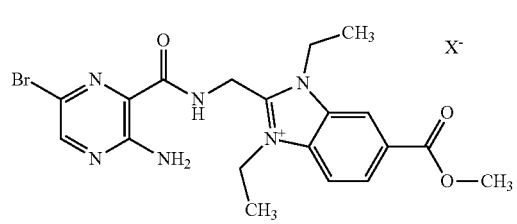 | 16 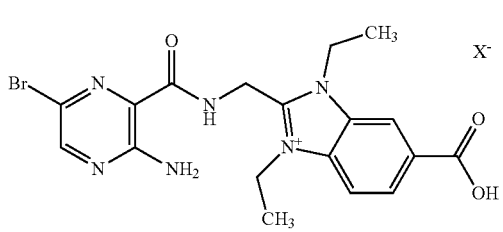 | |
| 17 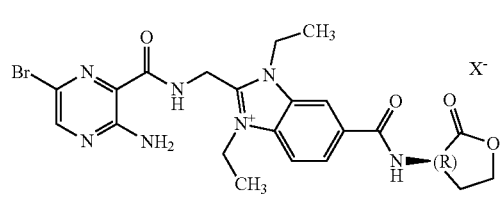 | 18 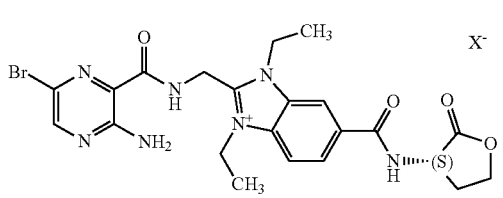 | |

-continued
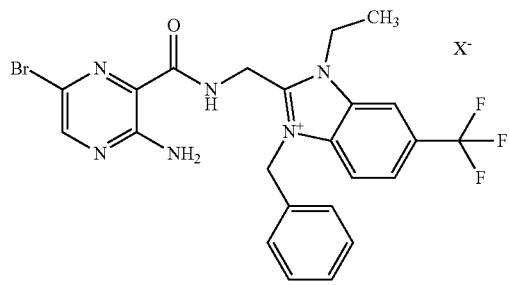
19
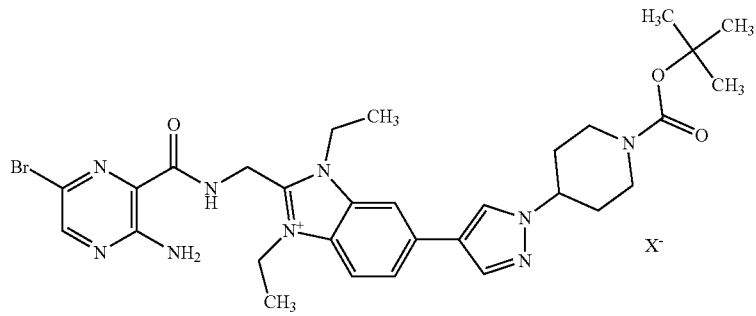
20
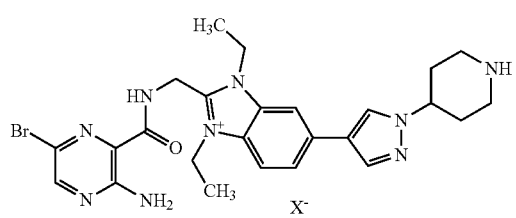
21
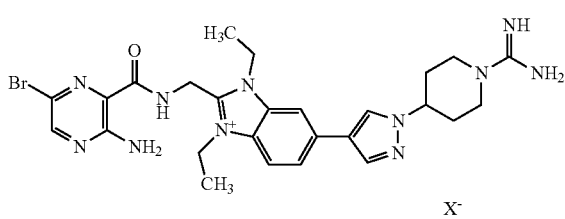
22
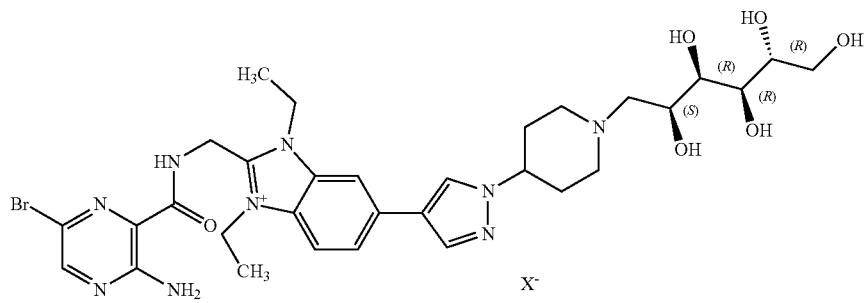
23
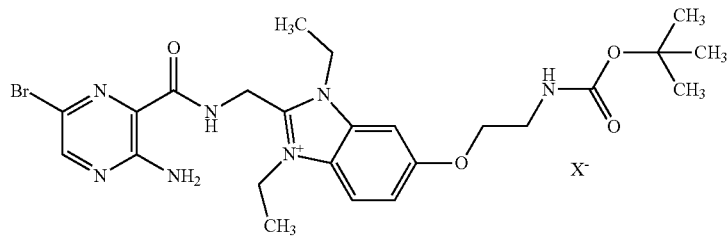
24
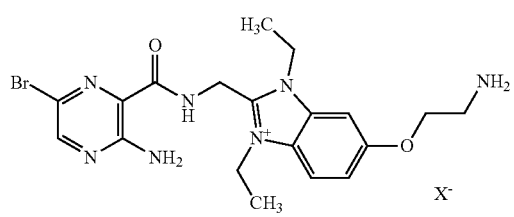
25
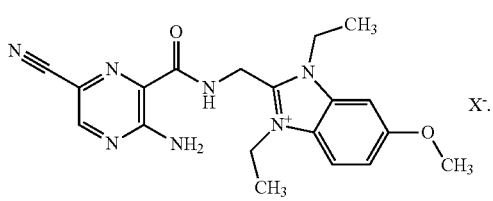
26

26. A process for the preparation of a compound according to claim 1, the process comprising reacting a compound of formula (II) or a salt thereof:

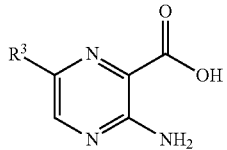
(II)

with a salt of formula (III):

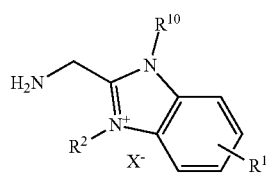
(III)

in the presence of a coupling reagent.

27. A method for the treatment of a patient, the method comprising administering to the patient a compound according to claim 1, wherein the patient has a respiratory disease or condition selected from the group consisting of cystic fibrosis, chronic obstructive pulmonary disease, chronic bronchitis, emphysema, bronchiectasis, and asthma.

28. A pharmaceutical composition comprising a compound according to claim 1 and a pharmaceutically acceptable excipient.

29. A pharmaceutical composition according to claim 28 formulated for oral, nasal, bronchial (inhaled) or topical administration.

30. A method for the treatment of a patient, the method comprising administering to the patient a compound according to claim 1, wherein the patient has a skin condition selected from the group consisting of psoriasis, atopic dermatitis, and ichthyosis.

31. A method for the treatment of a patient, the method comprising administering to the patient a compound according to claim 1, wherein the patient has dry eye disease.

32. A compound according to claim 25, wherein the anion $X^-$ is selected from the group consisting of halide, hydroxide, sulfate, nitrate, phosphate, formate, acetate, trifluoroacetate, fumarate, citrate, tartrate, oxalate, succinate, mandelate, methane sulfonate, and p-toluene sulfonate.

* * * * *